United States Patent [19]

Naka et al.

[11] Patent Number: 5,128,356
[45] Date of Patent: Jul. 7, 1992

[54] BENZIMIDAZOLE DERIVATIVES AND THEIR USE

[75] Inventors: Takehiko Naka, Kobe; Kohei Nishikawa, Kyoto, both of Japan

[73] Assignee: Takeda Chemical Industries, Ltd., Osaka, Japan

[21] Appl. No.: 599,894

[22] Filed: Oct. 19, 1990

[30] Foreign Application Priority Data

| Oct. 24, 1989 | [JP] | Japan | 1-277385 |
| Dec. 18, 1989 | [JP] | Japan | 1-328974 |
| Jan. 11, 1990 | [JP] | Japan | 2-005147 |
| Apr. 5, 1990 | [JP] | Japan | 2-091675 |
| Apr. 11, 1990 | [JP] | Japan | 2-097324 |
| Apr. 27, 1990 | [JP] | Japan | 2-113145 |

[51] Int. Cl.$^5$ ............... C07D 403/10; A61K 31/415
[52] U.S. Cl. ............................ 514/381; 548/253
[58] Field of Search ............ 548/113, 54, 325, 330, 548/253; 514/81, 381, 394

[56] References Cited

U.S. PATENT DOCUMENTS 4,880,804 11/1989 Carini et al. .................. 514/234.5

FOREIGN PATENT DOCUMENTS

| 0028833 | 5/1981 | European Pat. Off. |
| 0028834 | 5/1981 | European Pat. Off. |
| 0245637 | 11/1987 | European Pat. Off. |
| 0253310 | 1/1988 | European Pat. Off. |
| 0291969 | 11/1988 | European Pat. Off. |
| 0323841 | 7/1989 | European Pat. Off. |
| 392317 | 10/1990 | European Pat. Off. |
| 399732 | 11/1990 | European Pat. Off. |
| 400835 | 12/1990 | European Pat. Off. |
| 420237 | 4/1991 | European Pat. Off. |

*Primary Examiner*—Patricia L. Morris
*Assistant Examiner*—Lenora Miltenberger
*Attorney, Agent, or Firm*—Wegner, Cantor, Mueller & Player

[57] ABSTRACT

Novel imidazole derivatives of the formula (I):

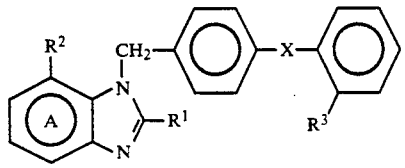

wherein $R^1$ is an optionally substituted alkyl group, $R^2$ and $R^3$ are independently a group capable of forming an anion or a group which can be changed thereinto, ring A is a benzene ring optionally having, besides the group shown by $R^2$, further substituents, and X shows linkage of phenylene group and phenyl group directly or through a spacer whose atomic length is not more than 2 and a salt thereof, show antagonistic actions to angiotensin II, thus being useful as therapeutics for cardiovascular diseases.

8 Claims, No Drawings

BENZIMIDAZOLE DERIVATIVES AND THEIR USE

BACKGROUND OF THE INVENTION

This invention relates to novel benzimidazole derivatives having excellent pharmacological activities and intermediates for synthesizing them.

More specifically, the present invention relates to compounds of the formula:

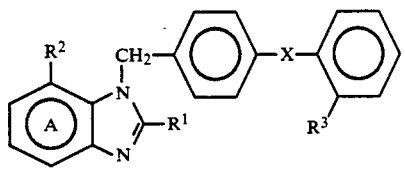

wherein $R^1$ stands for an optionally substituted alkyl group, $R^2$ and $R^3$ each stands for a group capable of forming an anion or a group which can be changed thereinto, ring A stands for benzene ring optionally having, besides the group shown by $R^2$, further substituents, and X shows linkage of phenylene group and phenyl group directly or through a spacer whose atomic chain is not more than 2 or salts thereof, which have strong angiotensine II antagonism and hypotensive activity and are useful as therapeutic agents of circulatory diseases such as hypertensive diseases, cardiac diseases, cerebral apoplexy, etc.

The renin-angiotensin system is involved in homeostasis to control systemic blood pressure, body fluid volume, and balance among the electrolytes, together with the aldosterone system. The relation between the renin-angiotensin system and hypertension has been clarified based on the fact that an inhibitor of an angiotensin II (AII) converting enzyme (ACE inhibitor) which produces angiotensin II having a potent vasoconstrictive action has been developed. Since angiotensin II elevates blood pressure via the angiotensin II receptors on the cellular membrane, the antagonists of angiotensin II, like ACE inhibitors, can be used for the treatment of hypertension. Many angiotensin II-related substances, such as saralasin and [Sar$^1$, Ala$^8$]AII, have been reported to have potent angiotensin II antagonism. However, the peptide antagonists have been reported to be of short duration of action after parenteral administration and to be ineffective in oral administration [M. A. Ondetti and D. W. Cushman, Annual Reports in Medicinal Chemistry, 13, 82–91(1978)].

On the other hand, for solving the problems observed with these peptide antagonists, non-peptide angiotensin II antagonists have been investigated. As one of the earliest studies in this field, imidazole derivatives having angiotensin II antagonism were disclosed in Japanese Patent Unexamined Publication Nos. 71073/1981, 71074/1981, 92270/1982, and 157768/1983, U.S. Pat. No. 4,355,040 and U.S. Pat. No. 4,340,598. Later, improved imidazole derivatives are disclosed in EP-0253310, EP-0291969, EP-0324377, Japanese Patent Unexamined Publication Nos. 23863/1988 and 117876/1989. And, pyrrole, pyrazole and triazole derivatives are disclosed in EP-0323841 and Japanese Patent Unexamined Publication No. 287071/1989 as angiotensin II antagonists.

The present inventors have considered that clinically useful compounds for therapy of circulatory diseases such as hypertension, cardiac diseases and cerebral apoplexy are required to have angiotensin II receptor antagonism and to show a strong angiotensin II antagonism and hypotensive action by oral administration thereof, and they have been intensively investigating the non-peptidic angiotensin II receptor antagonists on the basis of the above consideration.

Further, in U.S. Pat. No. 4,880,804, benzimidazole derivatives having angiotensin II receptor antagonism and effective for rats of renal hypertension by intravenous administration, for example, compounds (A) [represented by the following formula (A)] having hydroxymethyl, methoxy, formyl, chloro or carboxy group at the 5- or/and 6-positions, are disclosed. However, most of the compounds (A) are described as inactive when administered orally, while only 6-hydroxymethyl compounds and 6-chloro compounds are described as effective when administered orally (100 mg/kg or less). However, compounds showing only such an extent of potency as above are not satisfactory for putting them to practical use as medicinal products.

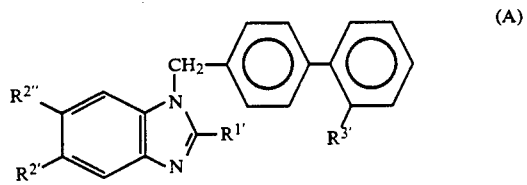

(A)

And, in the said U.S. patent, the compounds specifically embodied, including the above-mentioned compounds (A) are limited to benzimidazole having substituents at 5- or/and 6-positions on the benzene ring, and no disclosure of benzimidazole derivatives having substituents at 4- or 7-position is found.

DETAILED DESCRIPTION

The present inventors found that the specific compounds, i.e. 7-substituted benzimidazole derivatives, which are not described in U.S. Pat. No. 4,880,804, have a strong angiotensin II receptor antagonism, and also, when administered orally, show unexpectedly a strong AII antagonism and hypertensive action, which were not observed in the 5- or/and 6-position substituted derivatives. The present inventors have further developed their research work to accomplish the present invention.

More specifically, the present invention relates to compounds of the formula:

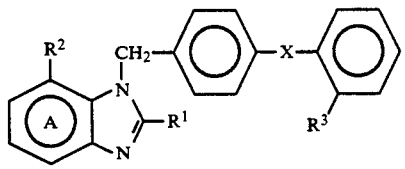

wherein $R^1$ is an optionally substituted alkyl group, $R^2$ and $R^3$ are independently a group capable of forming an anion or a group which can be changed thereinto, ring A is a benzene ring optionally having, besides the group shown by $R^2$, further substituents, and X shows linkage of the phenylene group and phenyl group directly or through a spacer whose atomic length is not more than 2 or salts thereof.

Referring to the above-mentioned general formula (I), the alkyl group shown by $R^1$ includes straight chain or branched lower alkyl groups having about 1 to 8 carbon atoms, such as methyl, ethyl, propyl, isopropyl, butyl, isobutyl, sec-butyl, t-butyl, pentyl, i-pentyl, hexyl, heptyl, octyl, etc. The alkyl groups may be substituted with a hydroxyl group, optionally substituted amino group, halogen, lower($C_{1-4}$) alkylthio group or a lower($C_{1-4}$) alkoxy group. Preferable groups shown by $R^1$ are lower($C_{2-5}$) alkyl groups optionally substituted with a hydroxyl group, amino group, halogen or a lower($C_{1-4}$) alkoxy group.

Examples of a group capable of forming an anion or a group which can be changed thereinto shown by $R^2$ include a group shown by the formula: $-(CH_2)_n-CO-D$ [wherein D stands for hydrogen, hydroxyl group, optionally substituted amino group, halogen or optionally substituted alkoxy group (e.g. lower($C_{1-6}$) alkoxy group whose alkyl portion may be substituted with a hydroxyl group, optionally substituted amino group, halogen, a group of the formula:

[wherein $R'''$ is hydrogen, a straight or branched lower ($C_{1-6}$) alkyl group (e.g. methyl, ethyl, n-propyl, isopropyl, n-butyl, isobutyl, sec-butyl, t-butyl, n-pentyl, isopentyl, neopentyl, etc.), or $C_{5-7}$ cycloalkyl group (e.g. cyclopentyl, cyclohexyl, cycloheptyl, etc.), and $R''''$ is a straight or branched lower ($C_{1-6}$) alkyl group (e.g. methyl, ethyl, n-propyl, isopropyl, n-butyl, isobutyl, sec-butyl, t-butyl, n-pentyl, isopentyl, neopentyl, etc.), $C_{5-7}$ cycloalkyl group (e.g. cyclopentyl, cyclohexyl, cycloheptyl, etc.), lower ($C_{1-3}$) alkyl (e.g. methyl, ethyl, n-propyl, isopropyl, etc.) or lower ($C_{2-3}$) alkenyl group (e.g. vinyl, propenyl, allyl, isopropenyl, etc.) substituted by $C_{5-7}$ cycloalkyl (e.g. cyclopentyl, cyclohexyl, cycloheptyl, etc.) or phenyl group, optionally substituted phenyl group (e.g. phenyl, etc.), a straight or branched lower ($C_{1-6}$) alkoxy group (e.g. methoxy, ethoxy, n-propoxy, isopropoxy, n-butoxy, isobutoxy, sec-butoxy, t-butoxy, n-pentyloxy, isopentyloxy, neopentyloxy, etc.), $C_{5-7}$ cycloalkyloxy group (e.g. cyclopentyloxy, cyclohexyloxy, cycloheptyloxy, etc.), lower ($C_{1-3}$) alkoxy group (e.g. methoxy, ethoxy, n-propoxy, isopropoxy, etc.) substituted by $C_{5-7}$ cycloalkyl (e.g. cyclopentyl, cyclohexyl, cycloheptyl, etc.) or phenyl group, optionally substituted phenoxy group (e.g. phenoxy, etc.), or optionally substituted benzyloxy group (e.g. benzyloxy, etc.)], lower ($C_{1-6}$) alkoxy group, lower ($C_{1-6}$) alkylthio group or optionally substituted dioxolenyl (e.g. 5-methyl-2-oxo-1,3-dioxolen-4-yl etc.), preferably lower($C_{1-6}$) alkoxy group whose alkyl portion may be substituted with hydroxyl group, optionally substituted amino group, halogen, lower($C_{2-6}$) alkanoyloxy, 1-lower($C_{1-6}$) alkoxy group, lower($C_{1-6}$) alkylthio or lower($C_{1-6}$) alkoxycarbonyloxy group), and n denotes 0 or 1], cyano, optionally protected (with e.g. alkyl or acyl group) tetrazolyl, phosphoric acid, sulfonic acid, phenolic hydroxyl group, optionally substituted alkoxy group, trifluoromethanesulfonic acid amide and lower($C_{1-3}$) alkyl group optionally substituted with hydroxyl group or optionally substituted amino group. Groups capable of forming anion or those which can be changed into such groups biologically, i.e. by being subjected to metabolism physiologically, or chemically (e.g. by oxidation, reduction or hydrolysis) are also within the meaning of $R^2$, and the compound (I), wherein $R^2$ stands for a group capable of forming an anion or a group which can be changed thereinto chemically, is useful also as an intermediate for synthesis.

Preferable groups shown by $R^2$ include those represented by the formula, $-(CH_2)_nCO-D$ [wherein D stands for hydrogen, hydroxyl group, amino, N-lower-($C_{1-4}$) alkylamino, N,N-di-lower($C_{1-4}$) alkylamino or lower($C_{1-6}$) alkoxy whose alkyl portion is optionally substituted with hydroxyl group, amino, halogen, lower($C_{2-6}$) alkanoyloxy, 1-lower($C_{1-6}$) alkoxy, lower($C_{1-6}$) alkylthio or lower($C_{1-6}$) alkoxycarbonyloxy, and n denotes 0 or 1] or tetrazolyl optionally protected with alkyl (e.g. lower($C_{1-4}$) alkyl, etc.) or acyl (e.g. lower($C_{2-5}$) alkanoyl or benzoyl. Further preferable groups are those represented by the formula, $-CO-D'$ [wherein $D'$ stands for hydroxyl group, amino, N-lower($C_{1-4}$) alkylamino, N,N-di-lower($C_{1-4}$) alkylamino or lower($C_{1-6}$) alkoxy whose alkyl portion is optionally substituted with a hydroxyl group, amino, halogen, lower($C_{2-6}$) alkanoyloxy, 1-lower($C_{1-6}$) alkoxy, lower($C_{1-6}$) alkylthio or lower($C_{1-6}$) alkoxycarbonyloxy] or tetrazolyl optionally protected with an alkyl or acyl group.

Examples of groups capable of forming an anion or groups which can be changed thereinto, shown by $R^3$, include carboxyl, tetrazolyl, trifluoromethanesulfonic acid amide ($-NHSO_2CF_3$), phosphoric acid, sulfonic acid, cyano, and lower($C_{1-4}$) alkoxycarbonyl, and these groups are optionally protected with optionally substituted a lower alkyl group or acyl group, so long as they are capable of forming an anion or groups which can be changed thereinto under biological, i.e. physiological conditions or chemically.

And, the compounds (I), wherein $R^3$ stands for a group capable of forming anion or a group which can be changed thereinto (e.g. cyano) chemically (e.g. by oxidation, reduction or hydrolysis), are useful as intermediates for synthesis.

Preferable groups shown by $R^3$ are carboxyl or tetrazolyl.

Examples of substituents on the benzene ring A other than the groups shown by $R^2$ include halogen (e.g. F, Cl, Br, etc.), nitro, cyano, optionally substituted amino groups [e.g. amino, N-lower($C_{1-4}$) alkylamino (e.g. methylamino, etc.), N,N-di-lower($C_{1-4}$) alkylamino (e.g. dimethylamino, etc.), N-arylamino (e.g. phenylamino, etc.), alicyclic amino (e.g. morpholino, piperidino., piperazino, N-phenylpiperazino, etc.)], groups represented by the formula $-Y-R$ [wherein Y stands for a chemical bond, $-O-$, $-S-$ or

and R stands for hydrogen, an optionally substituted lower alkyl group (e.g. lower($C_{1-4}$) alkyl group optionally substituted with hydroxyl group, optionally substituted amino group, halogen, lower($C_{1-4}$) alkoxy, etc.), or groups represented by the formula $-CO-D''$: [wherein $D''$ stands for hydrogen, optionally substituted alkoxy group [e.g. lower ($C_{1-4}$) alkoxy optionally substituted with optionally substituted amino group, hydroxyl group, halogen, lower ($C_{1-4}$) alkoxy, etc.], optionally substituted amino group [e.g. amino, N-lower($C_{1-4}$) alkylamino (e.g. methylamino), N,N-di-lower ($C_{1-4}$) alkylamino (e.g. dimethylamino), N-arylamino (e.g. phenylamino), alicyclic amino (e.g. morpholino, piperidino, piperazino or N-phenylpiperazino), etc.], halogen (e.g. chlorine, etc.) or hydroxyl group]. Among them, halogen, lower($C_{1-4}$) alkyl, lower($C_{1-4}$) alkoxy, nitro, and groups represented by the formula:

—CO—D''' [wherein D''' stands for hydroxyl group or lower($C_{1-2}$) alkoxy] or amino optionally substituted with lower($C_{1-4}$) alkyl are preferable, and halogen and lower($C_{1-4}$) alkyl are more preferable.

X shows that the adjacent phenylene group is bonded to the phenyl group directly or through a spacer whose atomic length is 2 or less. As the spacer, any one can be used, so long as it is a divalent chain in which the number of atoms constituting the straight chain is 1 or 2, and it may have a side chain. More specifically, it is exemplified by lower($C_{1-4}$) alkylene,

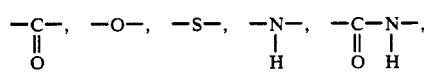

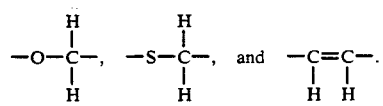

Among the compounds of the above formula (I), those of the formula (I')

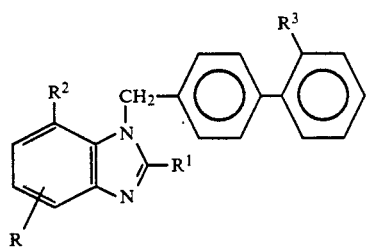

[wherein $R^1$ stands for lower($C_{2-5}$) alkyl optionally substituted with hydroxyl group, amino group, halogen or lower($C_{1-4}$) alkoxy group, $R^2$ stands for a group represented by the formula: —CO—D' [wherein D' stands for hydroxyl group, amino, N-lower($C_{1-4}$) alkylamino, N,N-di-lower($C_{1-4}$) alkylamino or lower($C_{1-4}$) alkoxy whose alkyl portion is optionally substituted with hydroxyl group, amino, halogen or lower($C_{1-4}$) alkoxy] or tetrazolyl group optionally protected with alkyl or acyl group, $R^3$ stands for carboxyl or tetrazolyl group optionally protected with alkyl or acyl group and R' stands for hydrogen, halogen, lower($C_{1-4}$) alkyl, lower($C_{1-4}$) alkoxy, nitro, a group represented by the formula: —CO—D''' [wherein D''' stands for hydroxyl group or lower($C_{1-2}$) alkoxy] or amino optionally substituted with lower($C_{1-4}$) alkyl (preferably hydrogen, lower($C_{1-4}$) alkyl, halogen, more preferably hydrogen)] are preferable.

Production Method

The compounds of the above-mentioned general formula (I) can be produced by, for example, the methods as shown below.

Reaction (a)

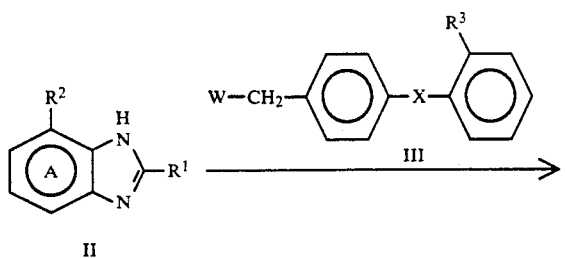

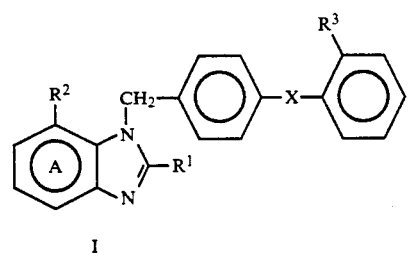

[wherein $R^1$, $R^2$, $R^3$, A and X are of the same meaning as defined above, and W stands for halogen atom].

Reaction (b)

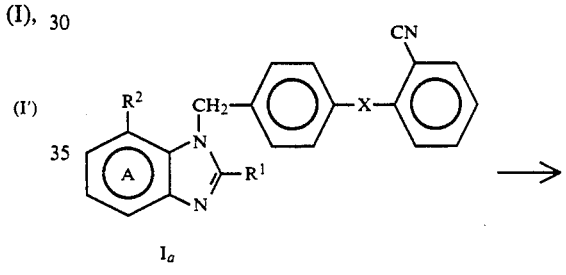

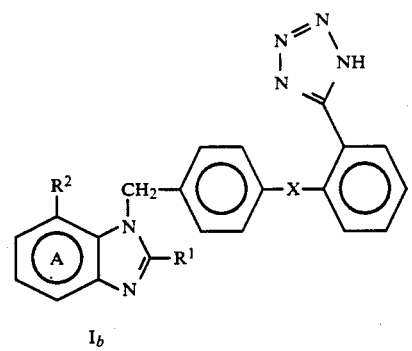

[wherein each symbol is of the same meaning as defined above].

Reaction (c)

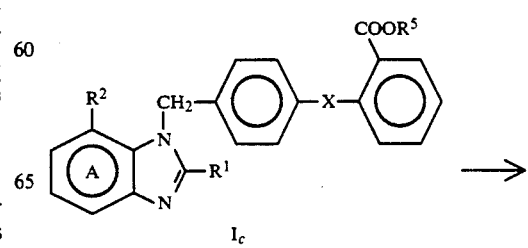

-continued

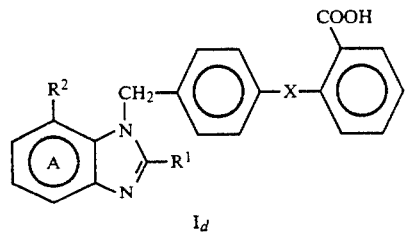

Reaction (f)

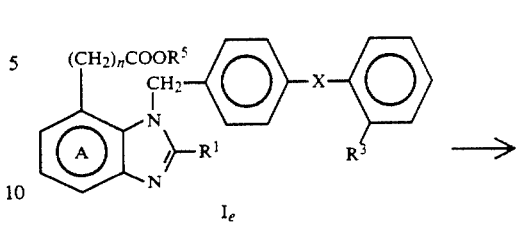

[wherein R¹, R², A and X are of the same meaning as defined above, and R⁵ stands for optionally substituted lower ($C_{1-4}$) alkyl].

Reaction (d)

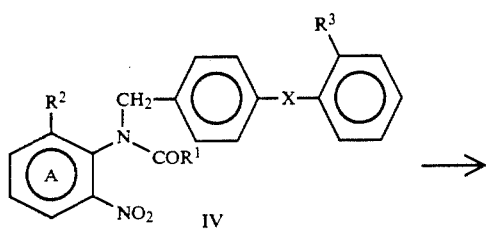

[wherein R¹, R³, R⁵, A and X are of the same meaning as defined above, and n denotes 0 or 1].

Reaction (g)

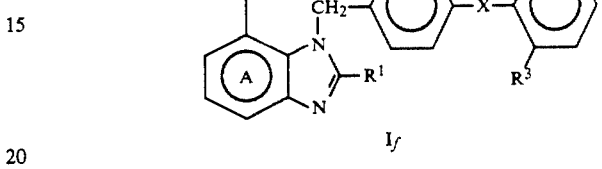

[wherein each symbol is of the same meaning as defined above].

Reaction (e)

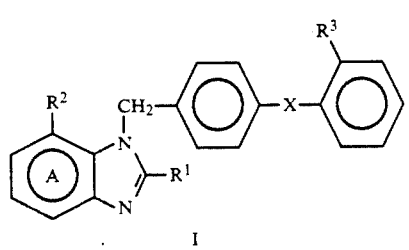

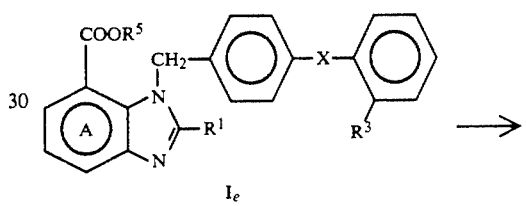

[wherein each symbol is of the same meaning as defined above].

Reaction (h)

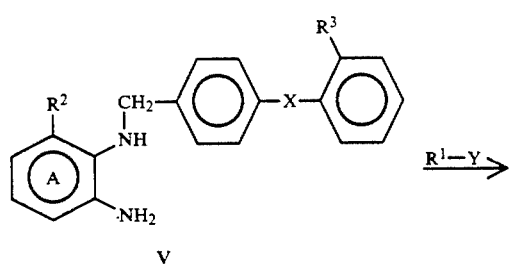

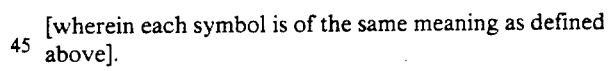

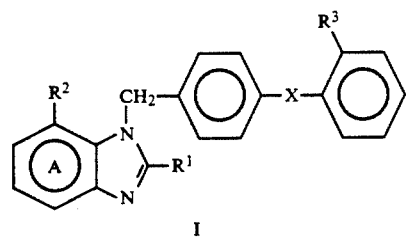

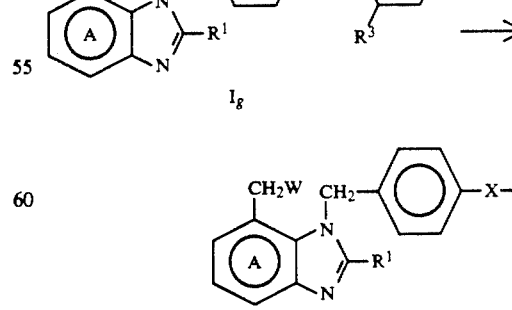

[wherein R¹, R², R³, A and X are of the same meaning as defined above, and Y stands for iminoether, iminothioether, carboxyl, amidine, cyano group, etc.].

[wherein R¹, R³, A and X are of the same meaning as defined above, and W stands for halogen atom].

Reaction (i)

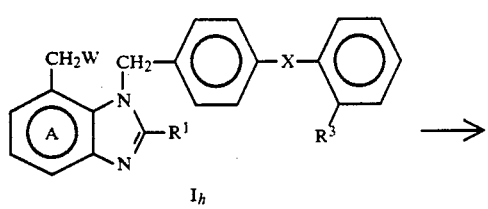

↓

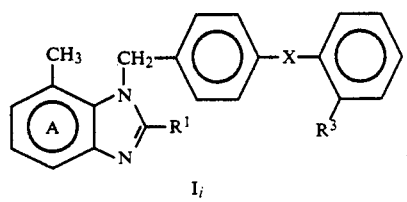

[wherein $R^1$, $R^3$, A, X and W are of the same meaning as defined above].

Reaction (j)

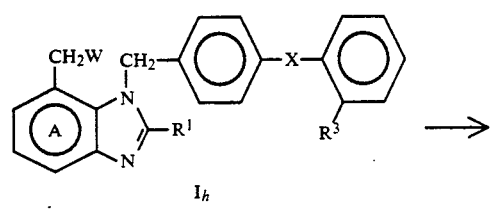

↓

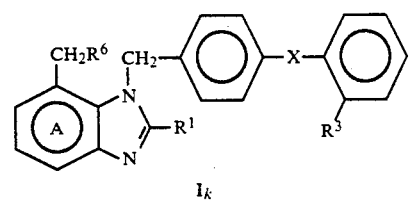

[wherein $R^1$, $R^3$, A, X and W are of the same meaning as defined above, and $R^6$ stands for lower alkoxy, lower alkylthio, optionally substituted amino group, or cyano group].

Reaction (k)

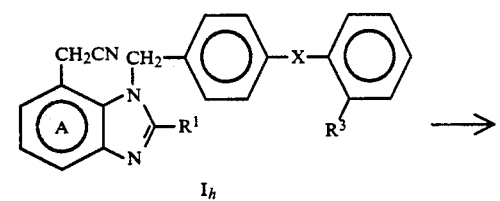

↓

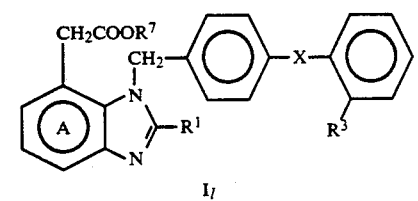

[wherein $R^1$, $R^3$, A and X are of the same meaning as defined above, $R^7$ stands for lower alkyl group].

Reaction (l)

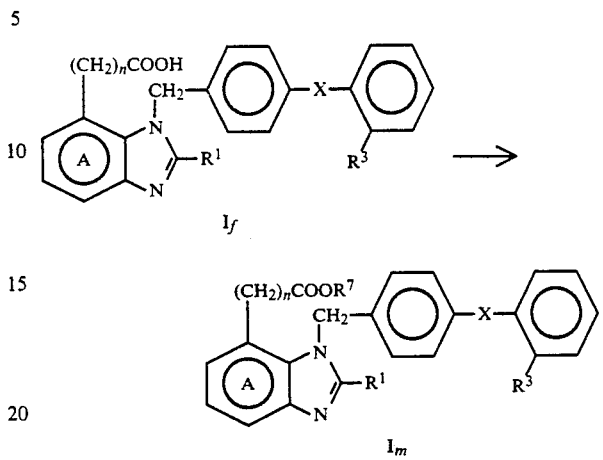

[wherein $R^1$, $R^3$, $R^7$, A and X are of the same meaning as defined above, and n denotes 0 or 1].

The above-mentioned reaction (a) is an alkylation by using the alkylating agent (III) in an organic solvent in the presence of a base.

Using about 1 to about 3 mol. of a base and about 1 to about 3 mol. of the alkylating agent (III) relative to 1 mol. of the compound (II), the reaction is conducted usually in a solvent such as dimethylformamide, dimethylacetamide, dimethylsulfoxide, acetonitrile, acetone, or ethyl methyl ketone.

As the base, use is made of e.g. sodium hydride, t-butoxy potassium, potassium carbonate or sodium carbonate.

The alkylating agent (III) is used in the form of a substituted halide (e.g. chloride, bromide and iodide), but it may be used in the form of a substituted sulfonic acid ester (e.g. methyl p-toluenesulfonate).

While reaction conditions vary with the combination of a base and the alkylating agent (III) to be employed, usually the reaction is conducted preferably at temperatures ranging from ice-cooling to room temperatures for about 1 to about 10 hours.

The reaction (b) is used to allow the cyano group substituted on the benzene ring of the compound (Ia) to react with various azides to give the tetrazole compound (Ib).

Using about 1 to about 3 mol. of an azide compound relative to 1 mol. of the compound (Ia), the reaction is carried out usually in a solvent e.g. dimethylformamide, dimethylacetamide, toluene or benzene.

Examples of these azides include trialkyltin azide, triphenyltin azide or hydrazoic acid.

When an organotin azide is employed, the reaction is conducted in toluene or benzene under reflux for 10 to 30 hours. When hydrazoic acid is employed, sodium azide and ammonium chloride are used about 2 times mol. relative to the compound (Ia), and the reaction is allowed to proceed in dimethylformamide at about 100 to about 130° C. for about 1 to 3 days. It is preferable to add to the reaction system an appropriate amount of sodium azide and ammonium chloride to accelerate the reaction.

The reaction (c) is used to obtain the carboxylic acid (Id) by hydrolysis of the ester (Ic) in the presence of alkali. Using about 1 to about 3 mol. of alkali relative to 1 mol. of the compound (Ic), the reaction is allowed to proceed in an aqueous alcohol (e.g. methanol, ethanol or methyl cellosolve). As the alkali, use is made of, among others, sodium hydroxide and potassium hydroxide. The reaction is allowed to proceed preferably at temperatures ranging from room temperatures to about 100° C. for about 1 to about 10 hours.

The reaction (d) is used to produce a benzimidazole derivative (I) by reduction of a nitro group, followed by intramolecular dehydrative cyclization.

The reaction is conducted by using about 2 to about 10 mol. of a reducing agent relative to 1 mol. of the compound (IV). As the reducing agent, mention is made of a metal such as iron, zinc or tin, and the reaction can be conducted usually under acid or alkaline conditions. As the solvent, use is made of alcohols (e.g. methanol and ethanol), ethers (e.g. dioxane and tetrahydrofuran) and acetic acid or hydrochloric acid singly or as a mixture solution.

The reaction conditions vary with a combination of a reducing agent, a solvent and acid (or alkali), and the reaction is usually allowed to proceed at temperatures ranging from room temperatures to about 100° C. for about 1 to about 5 hours.

For the completion of dehydrative cyclization after the reduction reaction, it is preferable to heat for about 2 to about 3 hours at about 50° C. to about 100° C. under acidic conditions.

The reaction (e) comprises a cyclization reaction of a diamino compound (V) with various compounds in an organic solvent into a benzimidazole compound (I).

The above-mentioned various compounds are exemplified by carboxylic acid, aldehyde, ortho ester, imino ether and imino thioether.

These reagents are used usually in quantities of 1 to about 10 mol. relative to 1 mol. of the compound (V), and the reaction is allowed to proceed in an organic solvent, but the reagent can be used dually as the solvent.

The organic solvents are, varying with the reagent then employed, exemplified by alcohols (methanol, ethanol, etc.), cellosolves (methyl cellosolve, ethyl cellosolve, etc.), halogenated hydrocarbons (chloroform, methylene chloride, etc.), ethers (dioxane, tetrahydrofuran, etc.), aromatic hydrocarbons (benzene, toluene), acetonitrile and dimethylformamide, among others.

For accelerating the reaction, an acid (hydrochloric acid, sulfuric acid, p-toluenesulfonic acid, etc.) or a base (triethylamine, pyridine, sodium methoxide, sodium ethoxide, potassium carbonate, etc.) can be added to the reaction system.

While the reaction conditions vary with reagents then employed, the reaction is conducted preferably at temperatures usually ranging from room temperatures to about the boiling point of the solvent then employed for about 1 hour to about 10 hours.

The reaction (f) is used to produce the carboxylic acid (If) by hydrolysis of the ester (Ie) in the presence of alkali.

Using about 1 to 3 mol. of alkali relative to 1 mol. of the compound (Ie), the reaction is carried out usually in an aqueous alcohol (e.g. methanol, ethanol, methyl cellosolve, etc.). As the alkali, use is made of sodium hydroxide and potassium hydroxide.

The reaction is conducted preferably at temperatures ranging from room temperatures to about 100° C. for about 1 to about 10 hours.

The reaction (g) is used to produce the hydroxymethyl compound (Ig) by reduction of the carboxylic acid ester (Ie).

The reaction is carried out by using about 1 to about 5 mol. of a reducing agent relative to 1 mol. of the compound (Ie). As the reducing agent, mention is made of, for example, lithium aluminum hydride or sodium borohydride. When the former is used, usually ether (tetrahydrofuran, dioxane, ethyl ether, etc.) is employed as the solvent, and the reaction is allowed to proceed for about 1 to about 20 hours at temperatures ranging from room temperatures to about the boiling point of the solvent then employed. And, when the latter is used, usually ether (tetrahydrofuran and dioxane) or alcohol (ethanol, propanol, butanol, etc.) is employed as the solvent, and it is preferable to add a suitable amount of methanol to the reaction system to accelerate the reaction. The reaction is allowed to proceed for about 1 to about 20 hours at temperatures ranging from room temperature to about the boiling point of the solvent then employed, preferably from about 50° C. to about the boiling point of the solvent.

The reaction (h) is used to produce the compound (Ih) by halogenation of the compound (Ig) with a halogenating reagent in an organic solvent.

Examples of the organic solvent include, among others, halogenated hydrocarbons such as dichloromethane, chloroform or dichloroethane and ethers such as ethyl ether, tetrahydrofuran or dioxane. As the halogenating reagent, use is made of, among others, thionyl chloride and phosphorus oxychloride. Among them thionyl chloride is preferable from the viewpoint of convenience of post-treatment of the reaction. The reaction is preferably carried out usually for about 1 to about 10 hours at temperatures ranging from room temperature to about the boiling point of the solvent then employed.

The reaction (i) is used to produce the methyl compound (Ii) by reducing the halogenated compound (Ih).

As the reducing agent, use is made of metal hydrides (e.g. organotin hydride), metal hydride complex compounds (e.g. sodium aluminum hydride or sodium borohydride), metals and salts thereof (e.g. zinc, copper, sodium or lithium). When, among them, a metal hydride (e.g. $Ph_3SnH$ or $Bu_3SnH$) is employed, the reaction carried out preferably in an aromatic hydrocarbon solvent (e.g. benzene or toluene) by using about 1 to about 3 times mol. of a tin hydride compound for about 3 to about 10 hours at about the boiling point of the solvent then employed. While the reaction proceeds rapidly when an iodide or bromide is employed, it is preferable to add peroxide (e.g. perbenzoic acid) or azobisisobutyronitrile (AIBN) to the reaction system to accelerate the reaction, when a chlorine compound is employed.

The reaction (j) is used to produce the substituted compound (Ik) by substitution reaction of the halogen compound (Ih) with a nucleophilic reagent in an organic solvent. Examples of the organic solvent include alcohols (e.g. methanol, ethanol, propanol, and butanol), ethers (e.g. tetrahydrofuran and dioxane), halogenated hydrocarbons (e.g. dichloromethane, chloroform and dichloroethane), acetonitrile and dimethylformamide. The solvent to be employed is preferably selected appropriately depending on the nucleophilic reagent then employed. Examples of the nucleophilic reagent include alcohols such as methanol, ethanol, etc., thiols such as methyl mercaptan, etc., amines such as alkylamine, aralkylamine, etc., and cyanides such as potassium cyanide, etc.

The reaction is carried out preferably in the presence of a suitable base (e.g. potassium carbonate, sodium carbonate, sodium hydride, sodium alkoxide, etc.).

Preferable reaction time is usually within the range from about one hour to about 10 hours at temperatures ranging from ice-cooling to about 50° C., but it varies with combination of the reagent and the solvent.

The reaction (k) is used to convert the nitrile (Ik) to the ester (Il).

It is convenient and preferable that the nitrile (Ik) is heated at temperatures ranging from about 50° C. to the boiling point of the solvent then employed for about 3 to about 20 hours in an alcohol (e.g. methanol, ethanol, propanol, butanol, etc.) containing about 3 to 10 molecular equivalents of excess hydrogen chloride gas. The alcohol then employed acts as the solvent and also as the reaction reagent. While, during the reaction, imino ether is produced as intermediate, it is preferable to obtain the ester compound without isolating the intermediate.

The reaction (l) is used to produce the ester (Im) by esterification of the carboxylic acid (If) with an alcohol.

The reaction is usually carried out by using a reactive alcohol (e.g. methanol, ethanol, propanol or butanol) in the presence of an acid catalyst. Examples of the catalyst include a mineral acid such as hydrochloric acid and sulfuric acid or an organic acid such as p-toluenesulfonic acid.

The reaction is preferably carried out for about 5 to about 20 hours at around the boiling point of the solvent.

The reaction products obtained by the reactions (a) to (l) can be easily isolated by conventional isolation and purification processes, for example, column chromatography and recrystallization.

These compounds (I) can be led, by a conventional method, to salts with a physiologically acceptable acid or base, for example, salts with an inorganic acid such as hydrochloride, sulfate and nitrate, salts with an organic acid such as acetate, oxalate, citrate and maleate, salts with an alkali metal such as sodium salt and potassium salt, and salts with an alkaline earth metal such as calcium salt.

Among these compounds, the starting compounds (II), (III), (IV) and (V) can be synthesized by, for example, the methods described in the following literature references or methods analogous thereto.

(1) P. N. Preston, "The Chemistry of Heterocyclic Compounds", Vol. 40, ed. by P. N. Preston, Tohn Wilcy & Sons, New York (1981), pp. 1-286, (2) A. Hunger, J. Kebrle, A. Rossi and K. Hottmann, Helv. Chim. Acta. 43, 1032 (1960), (3) R. C. De Selms, J. Org. Chem., 27, 2163 (1962), (4) A. F. Casy and J. Wrigit, J. Chem. Soc. (C), 1966, 1511, (5) O. Meth-Cohn, H. Suschitzky and M. E. Sutton, J. Chem. Soc. (C), 1968, 1722, (6) A. A. Shazhenov, Ch. Sh. Kadyrov and P. Kurbanov, Khim. Geterotsikl. Soedin., 1972, 641, (7) N. Vinot, Bull. Soc. Chim. Fr. 1966, 3989, (8) M. W. Partridge and H. A. Turner, J. Chem. Soc., 1958, 2086, (9) R. E. Lyle and J. L. Lamattina, J. Org. Chem., 40, 438(1975),

(10) S. H. Dandegaonker and C. R. Revankar, J. Karnatak Univ., 6, 25(1961) (cf. CA, 59, 10023b),

(11) Y. Kanaoka, O. Yonemitsu, K. Tanizawa and Y. Ban, Chem. Pharm. Bull., 12, 773 (1964),

(12) J. Preston, W. F. Dewinter and W. L. Hofferbert, Jr., J. Hetercycl. Chem., 6, 119(1969),

(13) B. C. Bishop, A. S. Jones and J. C. Tatlow, J. Chem., Soc., 1964, 3076,

(14) H. Depoorter, G. G. Van Mierlo, M. J. Libeer and J. M. Nys, Belg. 595, 327, Mar.23, 1961(cf. CA, 58, 9085a(1963)),

(15) H. J. J. Loozen and E. F. Godefroi, J. Org. Chem., 38, 3495(1973),

(16) N. Suzuki, T. Yamabayashi and Y. Izawa, Bull. Chem. Soc. Jpn., 49, 353(1976),

(17) V. J. Grerda, R. E. Jones, G. Gal and M. Sletzinger, J. Org. Chem., 30, 259 (1965),

(18) M. Itaya, Yakugaku Zasshi, 82, 1(1965),

(19) I. Ganea and R. Taranu, Stud. Univ. Babes-Bolyai. Ser. Chem., 1966, 95(cf.CA, 67, 32648s(1967)),

(20) D. Jerchel, H. Fischer and M. Kracht, Ann. Chem., 162(1952),

(21) N. S. Kozlov and M. N. Tovshtein, Vestsi Akad. Navuk Belarus. SSR, Ser. Khim. Navuk 1967, 89(cf.CA, 69, 49507p),

(22) J. B. Wright, Chem. Rev., 48, 397(1951).

And, the starting compound (IV) can easily be produced by alkylation of the compound (VI) synthesized by, for example, the method described in "K. Seno, S. Hagishita, T. Sato and K. Kuriyama, J. Chem. Soc., Perkin Trans. 1. 1984, 2013" or an analogous method thereto, or by subjecting the compound (VI) to a reaction similar to the reaction (a) or a reaction analogous thereto (e.g. the reaction shown by the following scheme (m)).

The starting compound (V) can be produced by the reaction shown by the following scheme (n) or a reaction analogous thereto.

The starting compounds (XIV) and (XV) can be produced by the reaction shown by the following scheme (o) or a reaction analogous thereto.

Reaction (m)

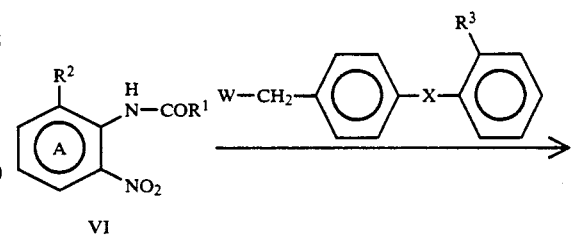

VI

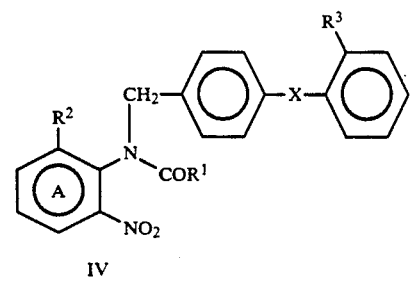

IV

[wherein A, $R^1$, $R^2$, $R^3$, X and n are of the same meaning as defined above, and W stands for halogen atom]

Reaction (n)

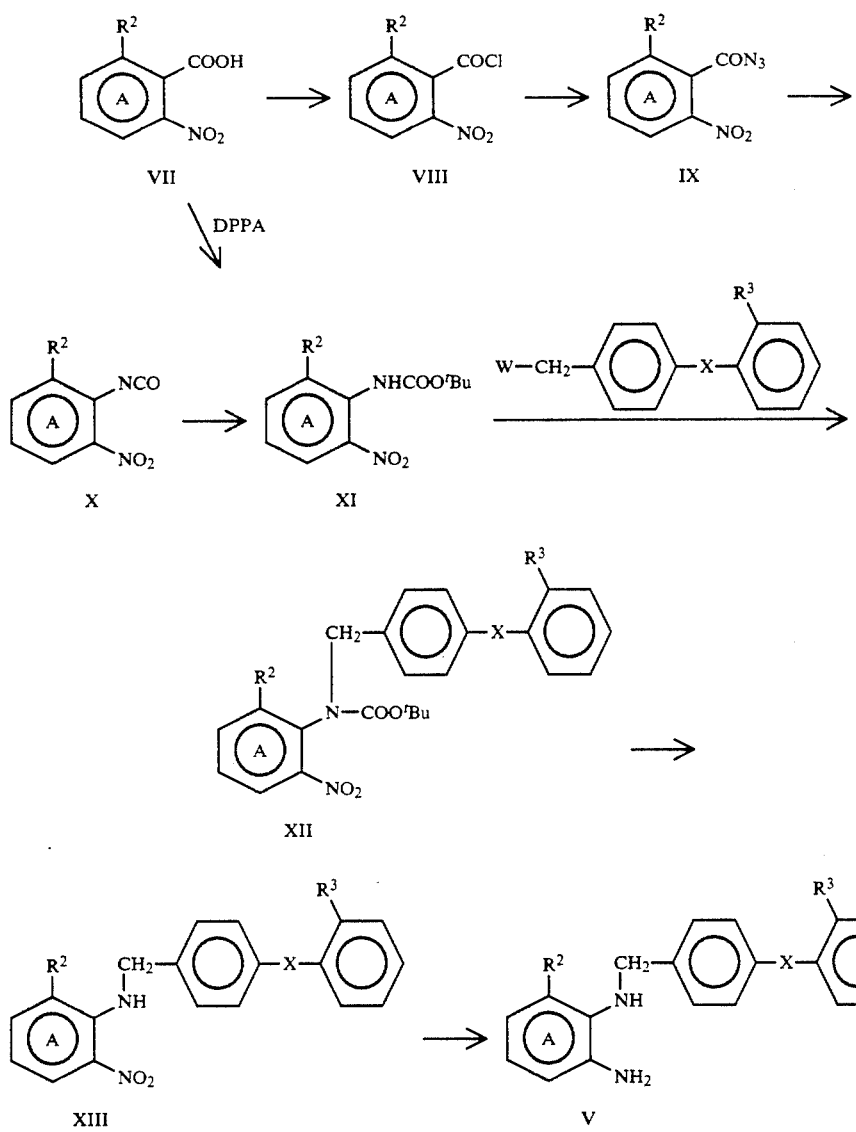
[wherein A, $R^2$, $R^3$ and X are of the same meaning as defined above, and W stands for halogen atom]
Reaction (o)
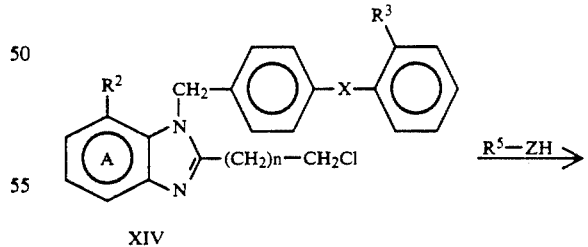
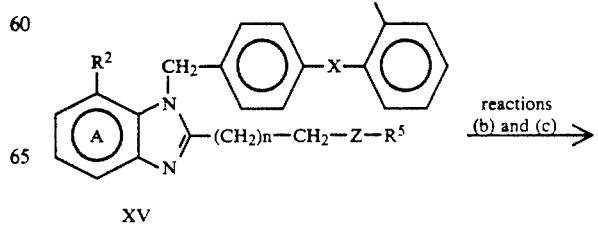

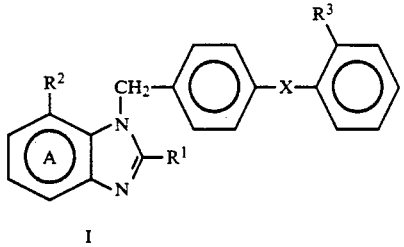

I

[wherein A, $R^1$, $R^2$, $R^3$, $R^5$ and X are of the same meaning as defined above, $R^8$ stands for carboxylic acid ester, cyano or optionally protected tetrazolyl, and Z is —O—, —NH— or —S—]

The reaction (m) produces an N-alkyl compound (IV) by alkylating the compound (VI) by a method similar to that of the reaction (a).

In the reaction (n), the acid azide (IX) which is produced by reacting the o-nitrobenzoate derivative (VII) with a halogenating reagent (e.g. thionyl chloride, phosphorus oxychloride, etc.) to give the acid chloride (VIII), followed by reaction with an azide compound (e.g. sodium azide, etc.) can be easily converted into the isocyanate (X), and the carbamic acid ester (XI) is produced in a high yield by heating the isocyanate (X) and t-butanol. On the other hand, the carbamic acid ester (XI) is produced by heating a mixture of the benzoate derivative (VII) and diphenyl phosphoryl azide (DPPA) in t-butanol. The diamino compound (V) is produced in a high yield by alkylating the obtained carbamic acid ester (XI) in a method similar to that of the reaction (m) to give the compound (XII), followed by deprotection and reaction with a reducing agent (e.g. raney nickel, stannic chloride, iron-hydrochloric acid, hydrazine-ferric chloride, etc.).

In the reaction (o), the benzimidazole derivative (XIV) is produced in a high yield by heating the diamino compound (V) and an acid chloride (e.g. chloroacetate chloride, 2-chloropropionate chloride, etc.) in the presence of a base (e.g. triethylamine, pyridine, etc.) to give a diacylamino compound, followed by heating the diacylamino compound and an acid (e.g. hydrochloric acid-ethanol, etc.), and the substituted compound (XV) is produced in a high yield by reacting the chloride (XIV) with various nucleophilic reagents (e.g. sodium methoxide, sodium ethoxide, methylamine, ethylamine, sodium thiomethoxide, sodium thioethoxide, etc.). The desired compound (I) can be produced by subjecting the obtained compound (XV) to the reaction (b), (c) or the like.

The compounds (I) and the salts thereof thus produced are less toxic, strongly inhibit the vasoconstrictive and hypertensive actions of angiotensin II, exert a hypotensive effect in animals, in particular mammals (e.g. human, dog, rabbit, rat, etc.), and therefore they are useful as therapeutics for not only hypertension but also cardiovascular diseases such as heart failure and cerebral stroke. The compounds (I) and salts thereof, when used as medicines as mentioned above, can be orally or nonorally administered as they are or in such dosage forms as powders, granules, tablets, capsules, injections, etc. prepared by mixing with appropriate pharmacologically acceptable carriers, excipients or diluents.

The dose varies with the diseases to be treated, symptoms, subjects and administration routes, and it is desirable that a daily dose of 1 to 50 mg for oral administration or 1 to 30 mg for intravenous injection is divided into 2 to 3 when used as an agent for the therapy of essential hypertension in adults.

EXAMPLES

By the following formulation examples, working examples, experimental examples and reference examples, the present invention will be explained more concretely, but they should not be interpreted as limiting the invention in any manner.

Examples of abbreviations in this specification are as follows:

Me: methyl, Et: ethyl, Pr: propyl, Bu: butyl, Pen: pentyl, Tet: tetrazolyl, THF: tetrahydrofuran, DMF: dimethylformamide, Ph: phenyl, Ac: acetyl

FORMULATION EXAMPLES

When the compound (I) of the present invention is used as a therapeutic agent for circulatory failures such as hypertension, heart failure, cerebral apoplexy, etc., it can be used in accordance with, for example, the following recipes.

1. Capsules

| (1) | 2-butyl-1-[[2'-(1H-tetrazol-5-yl)biphenyl-4-yl]methyl]benzimidazole-7-carboxylic acid | 10 mg |
|---|---|---|
| (2) | lactose | 90 mg |
| (3) | fine crystalline cellulose | 70 mg |
| (4) | magnesium stearate | 10 mg |
|   | one capsule | 180 mg |

(1), (2), (3) and a half of (4) are mixed and granulated. To the granules is added the remainder of (4), and the whole is filled into gelatin capsules.

2. Tablets

| (1) | 2-butyl-1-[[2'-(1H-tetrazol-5-yl)biphenyl-4-yl]methyl]benzimidazole-7-carboxylic acid | 10 mg |
|---|---|---|
| (2) | lactose | 35 mg |
| (3) | corn starch | 150 mg |
| (4) | fine crystalline cellulose | 30 mg |
| (5) | magnesium stearate | 5 mg |
|   | one tablet | 230 mg |

(1), (2), (3), two thirds of (4) and a half of (5) are mixed and granulated. To the granules are added the remainders of (4) and (5), followed by subjecting the granules to compression molding.

3. Injections

| (1) | 2-butyl-1-[[2'-(1H-tetrazol-5-yl)biphenyl-4-yl]methyl]benzimidazole-7-carboxylic acid disodium salt | 10 mg |
|---|---|---|
| (2) | inositol | 100 mg |
| (3) | benzyl alcohol | 20 mg |
|   | one ampoule | 130 mg |

(1), (2) and (3) are dissolved in distilled water for injection to make the whole volume 2 ml, which is filled into an ampoule. The whole process is conducted under sterile conditions.

4. Capsules

| (1) | 1-(cyclohexyloxycarbonyloxy)ethyl 2-butyl-1-[[2'-(1H-tetrazol-5-yl)biphenyl-4-yl]methyl]-benzimidazole-7-carboxylate | 10 mg |
|---|---|---|

4. Capsules

| | | |
|---|---|---|
| (2) | lactose | 90 mg |
| (3) | fine crystalline cellulose | 70 mg |
| (4) | magnesium stearate | 10 mg |
| | one capsule | 180 mg |

(1), (2), (3) and a half of (4) are mixed and granulated. To the granules is added the remainder of (4), and the whole is filled into gelatin capsules.

5. Tablets

| | | |
|---|---|---|
| (1) | 1-(cyclohexyloxycarbonyloxy)ethyl 2-butyl-1-[[2'-(1H-tetrazol-5-yl)biphenyl-4-yl]-methyl]benzimidazole-7-carboxylate | 10 mg |
| (2) | lactose | 35 mg |
| (3) | corn starch | 150 mg |
| (4) | fine crystalline cellulose | 30 mg |
| (5) | magnesium stearate | 5 mg |
| | one tablet | 230 mg |

(1), (2), (3), two thirds of (4) and a half of (5) are mixed and granulated. To the granules are added the remainders of (4) and (5), followed by subjecting the granules to compression molding.

6. Capsules

| | | |
|---|---|---|
| (1) | pivaloyloxymethyl 2-butyl-1-[[2'-(1H-tetrazol-5-yl)biphenyl-4-yl]methyl]benzimidazole-7-carboxylate | 10 mg |
| (2) | lactose | 90 mg |
| (3) | fine crystalline cellulose | 70 mg |
| (4) | magnesium stearate | 10 mg |
| | one capsule | 180 mg |

(1), (2), (3) and half of (4) are mixed and granulated. To the granules is added the remainder of (4), and the whole is filled into gelatin capsules.

7. Tablets

| | | |
|---|---|---|
| (1) | pivaloyloxymethyl 2-butyl-1-[[2'-(1H-tetrazol-5-yl)biphenyl-4-yl]methyl]benzimidazole-7-carboxylate | 10 mg |
| (2) | lactose | 35 mg |
| (3) | corn starch | 150 mg |
| (4) | fine crystalline cellulose | 30 mg |
| (5) | magnesium stearate | 5 mg |
| | one tablet | 230 mg |

(1), (2), (3), two thirds of (4) and a half of (5) are mixed and granulated. To the granules are added the remainders of (4) and (5), followed by subjecting the granules to compression molding.

REFERENCE EXAMPLE 1

2-Butyl-5-methoxybenzimidazole

To a solution of 4-methoxy-O-phenylenediamine (4.4 g) and ethyl valeriomidate hydrochloride (4.6 g) in ethanol (50 ml) was added triethylamine (5.7 g), and the mixture was stirred for 2.5 hours at room temperature. After removal of the solvent by evaporation, the resulting residue was dissolved in ethyl acetate and water, and the organic layer was washed with water, dried and concentrated. The concentrate was purified by column chromatography on silica gel to give a crystalline product. Recrystallization from isopropyl ether gave needles (2 7 g, 53%), m.p. 95°–96° C.

| Elemental Analysis for $C_{12}H_{16}N_2O$: | | |
|---|---|---|
| C(%) | H(%) | N(%) |
| Calcd: 70.50; | 7.89; | 13.71 |
| Found: 70.68; | 7.95; | 13.72 |

$^1$H-NMR(CDCl$_3$) δ: 0.93(3H,t), 1.2–2.0(4H,m), 2.89(2H,t), 3.81(3H,s), 6.84(1H,q), 7.02(1H,d), 7.42(1H,d).

In the manner of Reference Example 1, the following compounds were synthesized.

REFERENCE EXAMPLE 2

2-Butyl-5-chlorobenzimidazole

Colorless needles, m.p. 149°–150° C., yield 78%

| Elemental Analysis for $C_{11}H_{13}ClN_2$: | | |
|---|---|---|
| C(%) | H(%) | N(%) |
| Calcd: 63.31; | 6.28; | 13.42 |
| Found: 63.35; | 6.46; | 13.30 |

$^1$H-NMR(CDCl$_3$) δ: 0.90(3H,t), 1.20–1.60(2H,m), 1.67–2.00(2H,m), 1.67–2.00(2H,m), 2.92(2H,t), 7.17(1H,m), 7.38–7.52(2H,m).

REFERENCE EXAMPLE 3

2-Butyl-5-nitrobenzimidazole

Colorless crystals, m.p. 140–141° C., yield 77%.

REFERENCE EXAMPLE 4

2-Propylbenzimidazole

A mixture of o-phenylenediamine (2.2 g) in butyric anhydride (4.7 g) was stirred for 4 hours at 110° C. To the reaction mixture was added water, which was extracted with ethyl acetate. The organic layer was washed with an aqueous solution of sodium bicarbonate, dilute hydrochloric acid and water and then dried. The solvent was evaporated to dryness, and the residue was refluxed for 1.5 hour in 3N-HCl (35 ml). The reaction mixture was made basic with a 6N NaOH. The crystals were recrystallized from ethyl acetate-hexane to give colorless plates (0.9 g, 38%), m.p. 160°–162° C.

$^1$H-NMR(90 MHz,CDCl$_3$) δ: 1.00(3H,t), 1.88(2H,se(-hexaplet)), 2.91(2H,t), 2.91(2H,t), 7.10–7.35(2H,m), 7.45–7.70(2H,m), 8.30(1H,br s).

REFERENCE EXAMPLE 5

2-Pentylbenzimidazole

To a solution of 0-phenylenediamine (2.2 g) and triethylamine (2.0 g) in methylene chloride (20 ml) was added dropwise caproyl chloride (2.3 g) with stirring under ice-cooling. The mixture was stirred for 3 hours at room temperature, washed with a saturated aqueous sodium bicarbonate and water, then dried. The solvent was evaporated. To the residue was added 3N-HCl, and the mixture was heated for 1.5 hour under reflux. The reaction mixture was made basic with 6N NaOH. Then precipitating crystals were recrystallized from ethyl acetate-hexane to give colorless needles (1.5 g, 47%), m.p. 161°–162° C.

¹H-NMR(90 MHz, CDCl₃) δ: 0.86(3H,t), 1.1–1.6(4H,m), 1.7–2.0(2H,m), 2.92(2H,t), 7.1–7.3(2H,m), 7.5–7.7(2H,m).

REFERENCE EXAMPLE 6

2-Butyl-1-[(2,-cyanobiphenyl-4-yl)methyl]benzimidazole

To a solution of 2-butylbenzimidazole (0.87 g) in dimethylformamide (DMF) (5 ml) was added sodium hydride (60% oil, 0.24 g) under ice-cooling, and the mixture was stirred for 10 minutes. To the resultant mixture was added 4-(2-cyanophenyl)benzyl chloride (1.1 g), which was stirred for 1.5 hour. To the reaction mixture was added water and it was extracted with ethyl acetate. The extract was washed with water and concentrated under reduced pressure. The concentrate was purified by column chromatography on silica gel to give a colorless oil (1.8 g, quantitatively).

¹H-NMR(90 MHz, CDCl₃) δ: 0.90(3H,t), 1.2–1.6(2H,m), 1.65–2.00(2H,m), 2.85(2H,t), 5.37(2H,s), 7.0–7.9(12H,m).

The following compounds (Reference Examples 7–16) were prepared according to the procedure for Reference Example 6.

REFERENCE EXAMPLE 7

2-Butyl-1-[(2'-cyanobiphenyl-4-yl)methyl]-6-methoxy-benzimidazole

Oil (Yield 48%).
¹H-NMR(200 MHz,CDCl₃) δ: 0.93(3H,t), 1.14–1.53(2H,m), 1.76–1.91(2H,m), 2.83(2H,t), 3.81(3H,s), 5.37(2H,s), 6.70(1H,d), 6.89(1H,dd), 7.17(2H,d), 7.41–7.53(4H,m), 7.61–7.68(2H,m), 7.77(1H,dd).
IR(neat)cm⁻¹: 2220, 1620, 1595, 1520, 1485, 1460, 1415, 1350, 1275, 1260, 1215, 1175, 1135, 1105, 1025, 930, 815, 765.

REFERENCE EXAMPLE 8

2-Butyl-1-(2'-cyanobiphenyl-4-yl)methy]-5-methoxybenzimidazole

Oil (Yield 44%) ¹H-NMR(200 MHz,CDCl₃) δ: 0.93(3H,t), 1.35–1.53(2H,m), 1.76–1.92(2H,m), 2.85(2H,t), 3.86(3H,s), 5.38(2H,s), 6.86(1H,dd), 7.11(1H,d), 7.15(2H,d), 7.29(1H,d), 7.41–7.53(3H,m), 7.64(1H,dt), 7.77(1H,dd).
IR(neat)cm⁻¹: 2220, 1620, 1595, 1485, 1440, 1415, 1345, 1275, 1200, 1160, 1030, 835, 800, 765.

REFERENCE EXAMPLE 9

2-Butyl-5-chloro-1-(2'-cyanobiphenyl-4-yl)methyl]benzimidazole

Oil (Yield 48%).
¹H-NMR(200 MHz,CDCl) δ: 0.94(3H,t), 1.35–1.54(2H,m), 1.77–1.92(2H,m), 2.87(2H,t), 5.40(2H,s), 7.12–7.27(4H,m), 7.42–7.55(4H,m), 7.65(1H,q), 7.75–7.80(2H,m).
IR(neat)cm⁻¹: 2220, 1510, 1460, 1400, 760.

REFERENCE EXAMPLE 10

2-Butyl-6-chloro-1-[(2,-cyanobiphenyl-4-yl)methyl]-benzimidazole m.p. 124°–125° C. (yield 35%).
¹H-NMR(200 MHz,CDCl₃) δ: 0.94(3H,t), 1.35–1.54(2H,m), 1.77–1.92(2H,m), 2.85(2H,t), 5.37(2H,s), 7.14(2H,d), 7.20–7.25(2H,m), 7.41–7.55(4H,m), 7.61–7.70(2H,m), 7.77(1H,d).
IR(KBr)cm⁻¹: 2220, 1620, 1595, 1485, 1440, 1415, 1345, 1275, 1200, 1160, 1030, 835, 765.

REFERENCE EXMAPLE 11

2-Butyl-1-(2,-cyanobiphenyl-4-yl)methy4-5-nitrobenzimidazole

Oil (Yield 45%).

REFERENCE EXAMPLE 12

2-Butyl-1-(2'-cyanobiphenyl-4-yl)methyl-6-nitrobenzimidazole

Oil (Yield 43%).

REFERENCE EXAMPLE 13

1-(2'-Cyanobiphenyl-4-yl)methyl]-2-propylbenzimidazole

Oil (Yield quantitative).
¹H-NMR(200 MHz,CDCl₃) δ: 1.04(3H,t), 1.82–2.00(2H,m), 2.86(2H,t), 5.42(2H,s), 7.15(2H,d), 7.21–7.29(3H,m), 7.40–7.53(4H,m), 7.59–7.68(1H,m), 7.73–7.81(2H,m).
IR(neat)cm⁻¹: 2220, 1510, 1480, 1455, 1410, 760, 740.

REFERENCE EXAMPLE 14

1-(2'-Cyanobiphenyl-4-yl)methyl]-2-pentylbenzimidazole

Oil (Yield quantitative).
¹H-NMR(200 MHz,CDCl₃) δ: 0.88(3H,t), 1.23–1.44(4H,m), 1.80–1.95(2H,m), 2.87(2H,t), 5.43(2H,s), 7.16(2H,d), 7.21–7.29(3H,m), 7.41–7.53(4H,m), 7.60–7.68(1H,m), 7.74–7.82(2H,m).
IR(neat)cm⁻¹: 2220, 1510, 1480, 1455, 1410, 760, 740.

REFERENCE EXAMPLE 15

1-[(2'-Cyanobiphenyl-4-yl)methyl]benzimidazole

Oil (Yield quantitative).
¹H-NMR(200 MHz,CDCl₃) δ: 5.44(2H,s), 7.26–7.34(4H,m), 7.41–7.55(4H,m), 7.60–7.68(1H,m), 7.76(1H,dd), 7.83–7.87(1H,m), 8.01(1H,s).
IR(neat)cm⁻¹: 2220, 1500, 1480, 1460, 1440, 1365, 1285, 760, 740.

REFERENCE EXAMPLE 16

2-Butyl-1-(2,-cyanobiphenyl-4-yl)methylbenzimidazole

Oil (Yield quantitative).
¹H-NMR(90 MHz,CDCl₃) δ: 0.90(3H,t), 1.2–1.6(2H,m), 1.65–2.00(2H,m), 2.85(2H,t), 5.37(2H,s), 7.0–7.9(12H,m).

REFERENCE EXAMPLE 17

2-Butyl-1-2,-(1H-tetrazol-5-yl)biphenyl-4yl]methyl]-benzimidazole

A mixture of 2-butyl-1-[(2,-cyanobiphenyl-4-yl)methyl]benzimidazole (1.8 g), sodium azide (0.98 g) and ammonium chloride (0.80 g) was stirred in DMF (6 ml) at 110° C. for 5 days, while supplementing sodium azide (1.6 g), ammonium chloride (1.3 g) and DMF (5 ml) to the reaction system. To the reaction mixture were added water and ethyl acetate, and precipitating crystals were collected by filtration. The organic layer of the filtrate was washed with water, dried and concentrated under reduced pressure to give crude crystals. These crystals were combined with the crystals obtained previously, this was followed by recrystallization from ethyl acetate-methanol to afford colorless prisms (0.82 g, 41%), m.p. 235°–236° C.

| Elemental Analysis for C$_{25}$H$_{26}$N$_6$: | | | |
|---|---|---|---|
| | C(%) | H(%) | N(%) |
| Calcd: | 73.51; | 5.92; | 20.57 |
| Found: | 73.42; | 5.90; | 20.87 |

$^1$H-NMR(200 MHz,DMSO-d$_6$) δ: 0.87(3H,t), 1.226–1.45(2H,m), 1.62–1.77(2H,m), 2.82(2H,t), 5.49(2H,s), 7.05(4H,s), 7.13–7.22(2H,m), 7.46–7.71(6H,m).

IR(KBr)cm$^{-1}$: 1510, 1460, 1415, 775, 760, 745.

The following compounds were prepared according to the procedure for Reference Example 17.

REFERENCE EXAMPLE 18

2-Butyl-5-methoxy-1-[2,-(1H-tetrazol-5-yl)biphenyl-4-yl]methyl]benzimidazole m.p. 146°–149° C. (decomp.)

| Elemental Analysis for C$_{26}$H$_{26}$N$_6$O.2/5H$_2$O: | | | |
|---|---|---|---|
| | C(%) | H(%) | N(%) |
| Calcd: | 70.06; | 6.06; | 18.85 |
| Found: | 70.27; | 6.03; | 18.42 |

$^1$H-NMR(200 MHz,DMSO-d$_6$) δ: 0.87(3H,t), 1.25–1.44(2H,m), 1.60–1.75(2H,m), 2.78(2H,t), 3.77(3H,s), 5.45(2H,s), 6.80(1H,q), 7.01(2H,d), 7.06(2H,d), 7.13(1H,d), 7.35(1H,d), 7.47–7.70(4H,m).

IR(KBr)cm$^{-1}$: 1490, 1450, 1440, 1195, 1155, 1020, 825, 755.

REFERENCE EXAMPLE 19

2-Butyl-6-methoxy-1-[2,-(1H-tetrazol-5-yl)biphenyl-4-yl]methyl]benzimidazole m.p. 243°–244° C. (decomp.)

| Elemental Analysis for C$_{26}$H$_{26}$N$_6$O: | | | |
|---|---|---|---|
| | C(%) | H(%) | N(%) |
| Calcd: | 71.21; | 5.98; | 19.16 |
| Found: | 70.98; | 5.96; | 19.41 |

$^1$H-NMR(200 MHz,DMSO-d$_6$) δ: 0.86(3H,t), 1.24–1.43(2H,m), 1.58–1.73(2H,m), 2.75(2H,t), 3.75(3H,s), 5.45(2H,s), 6.78(1H,q), 7.05(5H,m), 7.43–7.70(5H,m).

IR(KBr)cm$^{-1}$: 1615, 1490, 1450, 1260, 1220, 1020, 825, 810, 745.

REFERENCE EXAMPLE 20

1-Butyl-5-chloro-1-2,-(1H-tetrazol-5-yl)bichenyl-4-yl]methyl]benzimidazole m.p. 249°–250° C. (decomp.)

| Elemental Analysis for C$_{25}$H$_{23}$ClN$_6$.1/2H$_2$O: | | | |
|---|---|---|---|
| | C(%) | H(%) | N(%) |
| Calcd: | 66.44; | 5.35; | 18.59 |
| Found: | 66.55; | 5.13; | 18.37 |

$^1$H-NMR(200 MHz,DMSO-d$_6$) δ: 0.87(3H,t), 1.26–1.44(2H,m), 1.61–1.76(2H,m), 2.81(2H,t), 5.50(2H,s), 6.99–7.09(4H,m), 7.20(1H,q), 7.47–7.70(7H,m).

IR(KBr)cm$^{-1}$: 1500, 1450, 1410, 1000, 785, 760.

REFERENCE EXAMPLE 21

2-Butyl-6-chloro-1-[[2'-(1H-tetrazol-5-yl)biphenyl-4-yl]methyl]benzimidazole m.p. 216°–217° C.

| Elemental Analysis for C$_{25}$H$_{23}$ClN$_6$: | | | |
|---|---|---|---|
| | C(%) | H(%) | N(%) |
| Calcd: | 67.79; | 5.23; | 18.97 |
| Found: | 67.41; | 5.19; | 19.02 |

$^1$H-NMR(200 MHz,DMSO-d$_6$) δ: 0.86(3H,t), 1.25–1.43(2H,m), 1.60–1.75(2H,m), 2.79(2H,t), 5.51(2H,s), 7.01(2H,d), 7.08(2H,d), 7.18(1H,q), 7.49–7.72(6H,m).

IR(KBr)cm$^{-1}$: 1460, 1410, 755.

REFERENCE EXAMPLE 22

1-[[2,-(1H-Tetrazol-5-yl)biphenyl-4-yl]methyl]benzimidazole

Yield: 51% m.p. 238°–239° C.

| Elemental Analysis for C$_{21}$H$_{16}$H$_6$.1/5H$_2$O: | | | |
|---|---|---|---|
| | C(%) | H(%) | N(%) |
| Calcd: | 70.85; | 4.64; | 23.61 |
| Found: | 70.75; | 4.40; | 23.41 |

$^1$H-NMR(200 MHz,DMSO-d$_6$) δ: 5.51(2H,s), 7.07(2H,d), 7.19–7.28(4H,m), 7.49–7.71(6H,m), 8.42(1H,s).

IR(KBr)cm$^{-1}$: 1505, 1460, 1375, 1290, 1265, 1230, 1195, 1145, 1035, 965, 945, 820, 775, 760, 750, 740.

REFERENCE EXAMPLE 23

2-Propyl-1-[[2,-(1H-tetrazol-5-yl)biphenyl-4-yl]methyl]benzimidazole

Yield: 70% m.p. 239°–240° C. (decomp.).

| Elemental Analysis for C$_{24}$H$_{22}$N$_6$.1/2MeOH.3/5H$_2$O: | | | |
|---|---|---|---|
| | C(%) | H(%) | N(%) |
| Calcd: | 69.85; | 6.03; | 19.95 |
| Found: | 69.88; | 6.01; | 19.79 |

$^1$H-NMR(200 MHz,DMSO-d$_6$) δ: 0.96(3H,t), 1.67–1.85(2H,m), 3.05(2H,t), 5.68(2H,s), 7.09(2H,d), 7.17(2H,d), 7.40–7.77(8H,m).

IR(KBr)cm$^{-1}$: 1505, 1480, 1460, 1415, 1405, 760, 745.

REFERENCE EXAMPLE 24

2-Pentyl-1-[[2'-(1H-tetrazol-5-yl)biphenyl-4-yl]methyl]-benzimidazole

Yield: 41% m.p. 208°–209° C.

| Elemental Analysis for C$_{26}$H$_{26}$N$_6$: | | | |
|---|---|---|---|
| | C(%) | H(%) | N(%) |
| Calcd: | 73.91; | 6.20; | 19.89 |

-continued

Elemental Analysis for $C_{26}H_{26}N_6$:

| | C(%) | H(%) | N(%) |
|---|---|---|---|
| Found: | 73.67; | 6.19; | 20.00 |

$^1$H-NMR(200 MHz,DMSO-d$_6$) δ: 0.84(3H,t), 1.27–1.34(4H,m), 1.64–1.78(2H,m), 2.81(2H,t), 5.49(2H,s), 7.04(4H,s), 7.12–7.20(2H,m), 7.46–7.69(6H,m).

IR(KBr)cm$^{-1}$: 1510, 1460, 1410, 745.

REFERENCE EXAMPLE 25

Methyl 2-[4-(2-butylbenzimidazol-1-yl)methylphenyl]benzoate

To a solution of 2-butylbenzimidazole (0.52 g) in DMF (4 ml) was added, under cooling with ice, sodium hydride (60% oil, 0.13 g), and then the mixture was stirred for 20 minutes. To the resultant mixture was added methyl 2-(4-bromomethylphenyl)benzoate (1.0 g), which was stirred for 1.5 hour at room temperature. To the mixture was added water, followed by extraction with ethyl acetate. The solvent was evaporated to dryness to give an oily residue. The oil was purified by column chromatography on silica gel to obtain a colorless oil (1.2 g, quantitatively).

$^1$H-NMR(90 MHz,CDCl$_3$) δ: 0.92(3H,t), 1.25–2.00(4H,m), 2.87 (2H,t), 3.60(3H,s), 5.36(2H,s), 7.05(2H,d), 7.15–7.60(8H,m), 7.65–7.9(2H,m).

IR(neat)cm$^{-1}$: 1725, 1455, 1405, 1280, 1245 780, 755, 740.

REFERENCE EXAMPLE 26

2-[4-(2-Butylbenzimidazol-1-yl)methylphenyl]benzoic acid

In a mixture of 1N NaOH solution (4.5 ml) and methanol (10 ml), methyl 2-[4-(2-butylbenzimidazol-1-yl)methylphenyl]benzoate (1.2 g) was heated for 3 hours under reflux. The reaction mixture was concentrated, and the concentrate was dissolved in water, washed with ether, then acidified with 1N-HCl to afford crystals. The crystals were collected by filtration and recrystallized from ethyl acetate-methanol to afford colorless crystals (0.64 g, 53%).

Elemental Analysis for $C_{25}H_{24}N_2O_2$:

| | C(%) | H(%) | N(%) |
|---|---|---|---|
| Calcd: | 78.10; | 6.29; | 7.29 |
| Found: | 77.99; | 6.36; | 7.22 |

$^1$H-NMR(200 MHz,CDCl$_3$) δ: 0.63(3H,t), 0.99–1.17(2H,m), 1.34–1 49(2H,m), 2.62(2H,t), 5.32(2H,s), 7.04(2H,d), 7.18–7.55(8H,m), 7.66(1H,dd), 7.92(1H,dd).

IR(KBr)cm$^{-1}$: 1690, 1610, 1600, 1515, 1465, 1420, 1300, 1250, 1140, 1090, 1005, 820, 765, 750.

REFERENCE EXAMPLE 27

Methyl 2-butylbenzimidazole-4-carboxylate

To a mixture of conc. HCl (5.3 ml) and methanol (35 ml) was added methyl 3-nitro-2-(N-valerylamino)benzoate (2.8 g), to which was added iron powder (1.7 g) in portions while stirring at room temperature. The resultant mixture was heated for 8 hours under reflux. Insoluble material was filtered off, and the filtrate was concentrated. To the concentrate were added water and ethyl acetate. The aqueous layer was made basic with 6N NaOH and was extracted with ethyl acetate. The organic layers were combined, washed with water and dried. The solvent was evaporated, and the residue was purified by column chromatography on silica gel. The crystals thus obtained were recrystallized from isopropyl ether to give colorless needles (1.6 g, 70%), m.p. 97°–98° C.

$^1$H-NMR(200 MHz,CDCl$_3$) δ: 0.93(3H,t), 1.37–1.56(2H,m), 1.80–1.95(2H,m), 2.96(2H,t), 4.00(3H,s), 7.26(1H,t), 7.85(1H,dd), 7.91(1H,d), 10.13(1H,br s).

REFERENCE EXAMPLE 28

Methyl 2-butyl-1-][(2'-cyanobiphenyl-4-yl)methyl]benzimidazole-4-carboxylate

To a solution of methyl 2-butylbenzimidazole-7-carboxylate (1.5 g) in DMF (15 ml) was added sodium hydride (60% oil, 0.13 g) under ice-cooling. The mixture was stirred for 20 minutes and there was added 4-(2-cyanophenyl)benzyl chloride (1.5 g). The resultant mixture was stirred for further 5 hours at room temperature and there was added water, followed by extraction with ethyl acetate. The organic layer was washed with water and dried. The solvent was evaporated to dryness, and the residue was purified by column chromatography on silica gel to give a pale yellow oil (2.3 g, 82%).

$^1$H-NMR(90 MHz,CDCl$_3$) δ: 0.94(3H,t), 1.37–1.55(2H,m), 1.78–1.93(2H,m), 2.96(2H,m), 4.05(3H,s), 5.46(2H,s), 7.12(2H,d), 7.25(1H,t), 7.39–7.52(5H,m), 7.64(1H,dt), 7.76(1H,d), 7.95(1H,dd).

IR(neat)cm$^{-1}$: 2220, 1710, 1510, 1480, 1435, 1405, 1350, 1290, 1245, 1215, 1190, 1130, 760.

REFERENCE EXAMPLE 29

Methyl 2-butyl-1-[[2,-(1H-tetrazol-5-yl)biphenyl-4-yl]methyl]-benzimidazole-4-carboxylate A mixture of methyl 2-butyl-1-[(2'-cyanobiphenyl-4-yl)methyl]benzimidazole-4-carboxylate (2.3 g), sodium azide (5.3 g) and ammonium chloride (4.4 g) was stirred in DMF (20 ml) at 110°–120 C. for 26 hours. To the reaction mixture were added water and ethyl acetate, which was then made acidic with concentrated hydrochloric acid. Precipitating crystals were collected by filtration and recrystallized from methanol to give colorless needles (0.22 g, 9%), m.p. 223°–224° C. (decomp.).

Elemental Analysis for $C_{27}H_{26}O_2 \cdot 0.3H_2O$:

| | C (%) | H (%) | N (%) |
|---|---|---|---|
| Calcd: | 68.72; | 5.68; | 17.81 |
| Found: | 68.69; | 5.68; | 17.57 |

$^1$H-NMR(200 MHz,DMSO-d$_6$) δ: 0.88(3H,t), 1.28–1.47(2H,m), 1.60–1.75(2H,m), 2.88(2H,t), 3.89(3H,s), 5.56(2H,s), 7.01(2H,d), 7.07(2H,d), 7.27(1H,t), 7.47–7.66(4H,m), 7.72–7.77(2H,m).

IR(KBr)cm$^{-1}$: 1710, 1460, 1435, 1420, 1295, 1140, 765.

REFERENCE EXAMPLE 30

2-Butyl-1-[[2'-(1H-tetrazol-5-yl)biphenyl-4-yl]methyl]-benzimidazole-4-carboxamide Substantially the same reaction as in Reference Example 29 was conducted. To the reaction mixture were added water and ethyl acetate, which was acidified with 6N-HCl. Precipitating crystals were collected by filtration. From the filtrate was separated the organic layer, which was washed with water, dried and concentrated to dryness. The residue was purified by column chromatography on silica gel. Crystals obtained thus above were recrystallized from methanol-chloroform to afford colorless prisms (0.37 g, 15%), m.p. 235–236°.

| Elemental Analysis for $C_{26}H_{25}N_7O.\frac{1}{2}H_2O$: | | | |
|---|---|---|---|
| | C (%) | H (%) | N (%) |
| Calcd: | 67.81; | 5.69; | 21.29 |
| Found: | 67.64; | 5.68; | 21.05 |

$^1$H-NMR(200 MHz,DMSO-d$_6$) δ: 0.89(3H,t), 1.30–1.48(2H,m), 1.65–1.80(2H,m), 2.90(2H,t), 5.58(2H,s), 7.06(4H,s), 7.30(1H,t), 7.48–7.74(5H,m), 7.84(1H,dd), 9.28(2H,s).

IR(KBr)cm$^{-1}$: 1660, 1610, 1565, 1500, 1465, 1420, 1390, 1350, 1255, 1080, 1070, 1015, 885, 800, 775, 750.

REFERENCE EXAMPLE 31

Methyl 3-nitro-2-valerylaminobenzoate

Fuming nitric acid (7.0 ml) was added dropwise to acetic anhydride (60 ml) under ice-cooling and there was added conc. sulfuric acid (0.2 ml). To the mixture was added methyl 2-valerylaminobenzoate (12 g), which was stirred for one hour at room temperature. To the resultant mixture was added ice-water and the mixture was then extracted with ethyl acetate. The organic layer was washed with water, dried and concentrated. The concentrate was purified by column chromatography on silica gel to give crude crystals, followed by recrystallization from isopropyl ether to afford colorless needles (3.9 g, 28%), m.p. 61°–62° C.

| Elemental Analysis for $C_{13}H_{16}N_2O_5$: | | | |
|---|---|---|---|
| | C (%) | H (%) | N (%) |
| Calcd: | 55.71; | 5.75; | 9.99 |
| Found: | 55.72; | 5.79; | 9.83 |

$^1$H-NMR(CDCl$_3$) δ: 0.95(3H,t), 1.30–1.50(2H,m), 1.65–1.80(2H,m), 2.46(2H,t), 3.97(3H,s), 7.30(1H,t), 8.10(1H,dd), 8.22(1H,dd).

REFERENCE EXAMPLE 32

Methyl 2-[N-(2'-cyanobiphenyl-4-yl)methyl-N-valeryl]amino-3-nitrobenzoate

A mixture of methyl 3-nitro-2-valerylaminobenzoate (3.9 g), 4-(2-cyanophenyl)benzyl bromide (3.8 g) and K$_2$CO$_3$ (2.1 g) in DMF (30 ml) was stirred for 15 hours at room temperature. To the reaction mixture was added water and it was extracted with ethyl acetate. The organic layer was washed with water and dried. The solvent was evaporated to dryness, and the residue was purified by column chromatography on silica gel. The resultant crude crystals were recrystallized from ethyl acetate-hexane to afford colorless crystals (5.1 g, 78%), m.p. 129°–130° C.

| Elemental Analysis for $C_{27}H_{25}N_3O_5$: | | | |
|---|---|---|---|
| | C (%) | H (%) | N (%) |
| Calcd: | 68.78; | 5.34; | 8.91 |
| Found: | 68.84; | 5.43; | 8.87 |

$^1$H-NMR(200 MHz,CDCl$_3$) δ: 0.85(3H,t), 1.18–1.36(2H,m), 1.61–1.76(2H,m), 2.08–2.16(2H,m), 3.67(3H,s), 4.65(1H,d), 4.96(1H,d), 7.20(2H,d), 7.38–7.50(4H,m), 7.56–7.68(2H,m), 7.75(1H,d), 7.98(1H,dd), 8.10(1H,dd).

REFERENCE EXAMPLE 33

Methyl 2-butyl-1-(2,-cyanobiphenyl-4-yl)methyl]benzimidazole-7-carboxylate

To a mixture of methyl 2-[N-(2,-cyanobiphenyl-4-yl)methyl-N-valeryl]amino-3-nitrobenzoate (5.14 g) in conc. HCl (4.0 ml) and methanol (10 ml) was added iron powder (1.9 g) in portions with stirring. The mixture was stirred for 3 hours at 70°–80° C., then insoluble material was filtered off, and the filtrate was concentrated. To the concentrate were added ethyl acetate and saturated aqueous sodium bicarbonate. Precipitating insoluble material was filtered off. From the filtrate was separated the aqueous layer, which was extracted with ethyl acetate. The organic layers were combined, dried and concentrated to give a crystalline residue. Recrystallization from ethyl acetate afforded colorless needles (4.15 g, 90%), m.p. 123°–124° C.

| Elemental Analysis for $C_{27}H_{25}N_3O_2$: | | | |
|---|---|---|---|
| | C (%) | H (%) | N (%) |
| Calcd: | 76.57; | 5.95; | 9.92 |
| Found: | 76.44; | 6.03; | 9.67 |

$^1$H-NMR(200MHz,CDCl$_3$) δ: 0.96(3H,t), 1.38–1.57(2H,m), 1.82–1.97(2H,m), 2.92(2H,t), 3.72(3H,s), 5.82(2H,s), 6.97(2H,d), 7.26(1H,t), 7.39–7.46(4H,m), 7.58–7.66(2H,m), 7.75(1H,dd), 7.97(1H,dd).

IR(KBr)cm$^{-1}$: 2220, 1725, 1480, 1440, 1420, 1400, 1280, 1260, 1195, 1140, 1115, 765, 750, 745.

The following compounds were prepared according to the procedure for Reference Example 31.

REFERENCE EXAMPLE 34

Methyl 2-butyrylamino-3-nitrobenzoate
m.p. 64°–65° C.
$^1$H-NMR(90MHz,CDCl$_3$) δ: 1.03(3H,t), 1.57–1.97(2H,m), 2.43(2H,t), 3.97(3H,s), 7.20–7.43(1H,m), 8.07–8.27(2H,m), 10.50(1H,br s).

IR(Nujol)cm$^{-1}$: 3300, 1725, 1690, 1585, 1535, 1510, 1445, 1355, 1265, 1210, 1115.

REFERENCE EXAMPLE 35

Methyl 2-hexanoylamino-3-nitrobenzoate
m.p. 74°–75° C. $^1$H-NMR(90MHz,CDCl$_3$) δ: 0.90(3H,t), 1.23–1.90(6H,m), 2.43(2H,t), 3.93(3H,s), 7.27(1H,t), 8.03–8.27(2H,m), 10.30(1H,br s).

IR(Nujol)cm$^{-1}$: 3320, 1725, 1675, 1535, 1505, 1270.

In substantially the same manner as in Reference Example 32, the following compounds were obtained.

REFERENCE EXAMPLE 36

Methyl 2-[N-butyryl-N-(2,-cyanobiphenyl-4-yl)methyl]amino-3-nitrobenzoate m.p. 150°–151° C. (yield 78%).
$^1$H-NMR(90MHz,CDCl$_3$) δ: 0.87(3H,t), 1.50–1.90(2H,m), 2.10(2H,t), 3.67(3H,s), 4.83(2H,q), 7.17–7.80(9H,m), 7.93–8.17(2H,m).
IR(Nujol)cm$^{-1}$: 2220, 1740, 1670, 1530, 1445, 1430, 1390, 1345, 1290, 1280, 1250, 1125, 770.

REFERENCE EXAMPLE 37

Methyl 2-N-(2'-cyanobiphenyl-4-yl)methyl-N-hexanoyl]amino-3-nitrobenzoate m.p. 85°–86° C. (yield 75%).
$^1$H-NMR(90MHz,CDCl$_3$) δ: 0.83(3H,t), 1.07–1.37(4H,m), 1.50–1.83(2H,m), 2.10(2H,t), 3.67(3H,s), 4.83(2H,q), 7.17–7.80(9H,m), 7.93–8.17(2H,m).
IR(Nujol)cm$^{-1}$: 2220, 1735, 1670, 1530, 1480, 1445, 1430, 1390, 1375, 1345, 1290, 1270, 1260, 1200, 1130, 775.

In substantially the same manner as in Reference Example 33, the following compounds were obtained.

REFERENCE EXAMPLE 38

Methyl 1-(2,-cyanobiphenyl-4-yl)methyl-2-propylbenzimidazole-7-carboxylate m.p. 130°–131° C. (yield 78%).
$^1$H-NMR(90MHz,CDCl$_3$) δ: 1.07(3H,t), 1.93(2H,br s), 2.90(2H,br s), 3.70(3H,s), 5.83(2H,br s), 6.93–8.07(11H,m).
IR(Nujol)cm$^{-1}$: 2220, 1710, 1450, 1400, 1290, 1270, 1265, 1200, 1125, 760.

REFERENCE EXAMPLE 39

Methyl 1-(2'-cyanobiphenyl-4-yl)methyl]-2-pentylbenzimidazole-7-carboxylate m.p. 109°–110° C. (yield 75%).
$^1$H-NMR(90MHz,CDCl$_3$) δ: 0.90(3H,t), 1.17–2.10(6H,m), 2.90(2H,t), 3.70(3H,s), 5.83(2H,s), 6.97(2H,d), 7.13–8.00(9H,m).
IR(Nujol)cm$^{-1}$: 2220, 1710, 1450, 1430, 1280, 1260, 1190, 1120, 750.

REFERENCE EXAMPLE 40

Methyl 3-nitro-4-valerylaminobenzoate

Fuming nitric acid (1.4 ml) was added dropwise to acetic anhydride (12 ml) under ice-cooling and then was added conc. sulfuric acid (0.1 ml). To the stirred mixture was added methyl 4-valerylaminobenzoate (2.3 g) under ice-cooling, followed by stirring for one hour. To the resultant mixture was added ice water, and the crystals separated out were recrystallized from ethyl acetate - hexane to give yellow prisms (2.14 g, 76%),
m.p. 106°–107° C.

| Elemental Analysis for C$_{13}$H$_{16}$N$_2$O$_5$: | | |
|---|---|---|
| | C (%) | H (%) | N (%) |
| Calcd: | 55.71; | 5.75; | 9.99 |
| Found: | 55.84; | 5.80; | 10.01 |

$^1$H-NMR(CDCl$_3$) δ: 0.98(3H,t), 1.20–1.60(2H,m), 1.70–1.85(2H,m), 2.53(2H,t), 3.96(3H,s), 8.28(1H,dd), 8.91(1H,d), 8.96(1H,d), 10.60(1H,br s).

REFERENCE EXAMPLE 41

Methyl 4-N-(2'-cyanobiphenyl-4-yl)methyl-N-valerylamino]-3-nitrobenzoate

A mixture of methyl 4-valerylamino-3-nitrobenzoate (2.1 g), 4-(2-cyanophenyl)benzyl bromide (2.0 g) and K$_2$CO$_3$ (1.1 g) in DMF (20 ml) was stirred for 4 hours at room temperature. To the reaction mixture was added water, the mixture was extracted with ethyl acetate, and the organic layer was washed with water. The resultant solution was dried and concentrated to give a syrup, which was purified by column chromatography on silica gel to afford a yellow syrup (3.5 g, quantitatively).
$^1$H-NMR(200MHz,CDCl$_3$) δ: 0.83(3H,t), 1.15–1.33(2H,m), 1.55–1.70(2H,m), 1.99–2.08(2H,m), 3.98(3H,s), 4.27(1H,d), 5.55(1H,d), 7.07(1H,d), 7.27(2H,d), 7.42–7.56(4H,m), 7.62–7.70(1H,m), 7.77(1H,d), 8.19(1H,q), 8.61(1H,d).
IR(Neat)cm$^{-1}$: 2220, 1730, 1610, 1535, 1480, 1435, 1390, 1345, 1285, 1240, 765.

REFERENCE EXAMPLE 42

Methyl 2-butyl-1-[(2'-cyanobiphenyl-4-y)methyl]benzimidazole-5-carboxylate

To a mixture of conc. HCl (4.0 ml) and methanol (10 ml) was added methyl 4-[N-(2'-cyanobiphenyl-4-yl)methyl-N-valerylamino]-3-nitrobenzoate (3.5 g). To the resultant mixture was added, with stirring, iron powder (1.3 g) in portions and the mixture was stirred for one hour at 70°–80° C., followed by filtering off an insoluble material. The filtrate was concentrated, which was dissolved in ethyl acetate, washed with water, dried and concentrated to dryness. The resultant syrup was purified by column chromatography on silica gel to afford a yellow syrup (1.7 g, 53%).
$^1$H-NMR(200MHz,CDCl$_3$) δ: 0.94(3H,t), 1.45(2H,se), 1.79–1.94(2H,m), 2.89(2H,t), 3.94(3H,s), 5.44(2H,s), 7.15(2H,d), 7.27(1H,d), 7.42–7.54(4H,m), 7.65(1H,dt), 7.77(1H,dd), 7.97(1H,dd), 8.50(1H,dd).
IR(neat)cm$^{-1}$: 2220, 1720, 1615, 1480, 1440, 1400, 1335, 1300, 1280, 1210, 755.

REFERENCE EXAMPLE 43

Methyl 2-butyl-1-2'-(1H-tetrazol-5-yl)biphenyl-4-yl]methyl]-benzimidazole-5-carboxylate A mixture of methyl 4-[N-(2'-cyanobiphenyl-4-yl)methyl-N-valerylamino]-3-nitrobenzoate (1.7 g), sodium azide (3.9 g) and ammonium chloride (3.2 g) in DMF (17 ml) was stirred at 115 ° C. for 5 days. To the reaction mixture was added water and the mixture was neutralized with 1N-HCl, followed by extraction with ethyl acetate. The organic layer was washed with water, dried and concentrated to dryness. The concentrate was purified by column chromatography on silica gel to give crude crystals. Recrystallization from ethyl acetate gave colorless needles (0.67 g, 34%), m.p. 134°-136° C.

| Elemental Analysis for $C_{27}H_{26}N_6O_2 \cdot \frac{1}{2}H_2O$: | | | |
|---|---|---|---|
| | C (%) | H (%) | N (%) |
| Calcd: | 68.19; | 5.72; | 17.67 |
| Found: | 68.46; | 5.77; | 17.31 |

$^1$H-NMR(200MHz,CDCl$_3$) δ: 0.83(3H,t), 1.18-1.37(2H,m), 1.50-1.65(2H,m), 2.38(2H,t), 3.90(3H,s), 5.24(2H,s), 6.68(2H,d), 6.91(2H,d), 7.06(1H,d), 7.28-7.33(1H,m), 7.54-7.69(3H,m), 7.87(1H,dd), 8.00(1H,dd).
IR(KBr)cm$^{-1}$: 1720, 1615, 1515, 1435, 1410, 1340, 1300, 1280, 1220, 1085, 770, 750.

REFERENCE EXAMPLE 44

2-Butyl-1-2'-(1H-tetrazol-5-yl)biphenyl-4-yl]methyl]-benzimidazole-5-carboxylic acid A mixture of methyl 2-butyl-1-[[2'-(1H-tetrazol-5-yl)biphenyl-4-yl]methyl]benzimidazole-5-carboxylate (0.3 g) in methanol (3 ml) containing 2N NaOH (1 ml) was heated under reflux for two hours. The reaction mixture was concentrated to dryness and then dissolved in water. The aqueous solution was made acidic with 1N-HCl to give crystals. Recrystallization from acetonitrile-methanol afforded colorless crystals (0.23 g, 83%), m.p. 180°-182° C.

| Elemental Analysis for $C_{26}H_{24}N_6O_2$: | | | |
|---|---|---|---|
| | C (%) | H (%) | N (%) |
| Calcd: | 68.16; | 5.49; | 19.08 |
| Found: | 68.43; | 5.27; | 18.88 |

$^1$H-NMR(200MHz,DMSO-d$_6$) δ: 0.88(3H,t), 1.28-1.46(2H,m), 1.63-1.78(2H,m), 2.89(2H,t), 5.58(2H,s), 7.07(4H,s), 7.47-7.70(5H,m), 7.86(1H,dd), 8.18(1H,s).

REFERENCE EXAMPLE 45

Methyl 3-valerylaminobenzoate

To a solution of methyl 3-aminobenzoate (6.0 g) and triethylamine (4.5 g) in methylene chloride (90 ml) was added dropwise, while stirring under ice-cooling, valeryl chloride (4.8 g). The mixture was stirred for one hour. The reaction mixture was washed with an aqueous solution of sodium bicarbonate, dilute hydrochloric acid and water, followed by drying and concentration to dryness. The concentrate was crystallized from ethyl acetate - hexane to afford colorless prisms (8.1 g, 87%), m.p. 101°-102° C.

$^1$H-NMR(90MHz,CDCl$_3$) δ: 0.93(3H,t), 1.2-1.9(4H,m), 2.37(2H,t), 3.90(3H,s), 7.36(1H,t), 7.5(1H,br s), 7.70-7.95(2H,m), 8.03(1H,t).

REFERENCE EXAMPLE 46

Methyl 4-nitro-3-valerylaminobenzoate

To a solution of methyl 3-valerylaminobenzoate (2.3 g) in acetic anhydride (12 ml) was added dropwise fuming nitric acid (1.4 ml) while stirring under ice-cooling. To the mixture was added one drop of conc. sulfuric acid and the mixture was stirred for two hours. To the reaction mixture was added ice-water and it was extracted with ethyl acetate. The organic layer was washed with an aqueous solution of sodium bicarbonate and water and then dried. The solvent was evaporated to dryness, and the residue was purified by column chromatography on silica gel to afford a brown oil (1.0 g, 36%).

$^1$H-NMR(90MHz,CDCl$_3$) δ: 0.96(3H,t), 1.1-1.9(4H,m), 2.51(2H,t), 3.96(3H,s), 7.80(1H,dd), 8.26(1H,d),9.41(1H,d), 10.23(1H,br s).
IR(neat)cm$^{-1}$: 3380, 1730. 1615, 1590, 1535, 1500, 1440, 1420, 1325, 1310, 1280, 1250, 1210, 1160, 1110, 1070, 845, 775, 740.

REFERENCE EXAMPLE 47

Methyl 3-[N-(2'-cyanobiphenyl-4-yl)methyl-N-valerylamino-4-nitrobenzoate

A mixture of methyl 4-nitro-3-valerylaminobenzoate (1.0 g), 4-(2-cyanophenyl)benzyl bromide (0.97 g) and potassium carbonate (0.55 g) in DMF (10 ml) was stirred for two days at room temperature. To the reaction mixture was added water and the mixture was extracted with ethyl acetate. The organic layer was washed with water and dried. The solvent was distilled off, and the residue was purified by column chromatography on silica gel to afford a pale yellow oil (1.24 g, 73%)

$^1$H-NMR(200MHz, CDCl$_3$) δ: 0.84(3H,t), 1.17-1.30(2H,m), 1.56-1.71(2H,m), 1.80-2.08(2H,m), 3.92(3H,s),4.43(1H,d), 5.37(1H,d), 7.26(2H,d), 7.40-7.51(4H,m), 7.60-7.69(2H,m), 7.75(1H,d), 7.97(1H,d), 8.16(1H,dd).
IR(neat)cm$^{-1}$: 2220, 1735, 1675, 1600, 1580, 1530, 1480, 1435, 1420, 1390, 1350, 1285, 1220, 1200, 1115, 1090, 825, 775, 765.

REFERENCE EXAMPLE 48

Methyl 2-butyl-1-(2'-cyanobiphenyl-4-yl)methyl]benzimidazole-6-carboxylate

To a solution of methyl 3-[N-(2'-cyanobiphenyl-4-yl)methyl-N-valerylamino]-4-nitrobenzoate (1.2 g) in methanol (10 ml) containing conc. HCl (1.3 ml), was added, while stirring at room temperature, iron powder (0.45 g) in portions. The mixture was stirred for 3 hours at 70°-80° C. To the reaction mixture were added water and ethyl acetate and the mixture was made basic with an aqueous solution of sodium bicarbonate. Precipitates then separated were filtered off. The organic layer separated from the filtrate was washed with water and dried. The solvent was evaporated to dryness, and the residue was purified by column chromatography on silica gel. Crude crystals thus obtained were recrystallized from ethyl acetate to give colorless needles (0.5 g, 45%), m.p. 166°-167° C.

| Elemental Analysis for $C_{27}H_{25}N_3O_2$: | | | |
|---|---|---|---|
| | C (%) | H (%) | N (%) |
| Calcd: | 76.57; | 5.95; | 9.92 |
| Found: | 76.39; | 6.05; | 9.79 |

$^1$H-NMR(200MHz,CDCl$^3$) δ: 0.94(3H,t), 1.35-1.54(2H,m), 1.79-1.94(2H,m), 2.88(2H,t), 3.92(3H,s), 5.47(2H,s), 7.14(2H,d), 7.40-7.53(4H,m), 7.60-7.68(1H,m), 7.74-7.80(2H,m), 7.96-8.02(2H,m).

IR(KBr)cm$^{-1}$: 2210, 1715, 1620, 1580, 1510, 1480, 1460, 1425, 1410, 1340, 1325, 1280, 1270, 1250, 1230, 1185, 1105, 1080, 770, 760, 745.

REFERENCE EXAMPLE 49

Methyl 2-butyl-1-[[2'-(1H-tetrazol-5-yl)biphenyl-4-yl]methyl]-benzimidazole-6-carboxylate A mixture of methyl 2-butyl-1-[2'-(cyanobiphenyl-4-yl)methyl]benzimidazole-6-carboxylate (0.5 g), sodium azide and ammonium chloride (1.15 g) in DMF (5 ml) was stirred at 115° C. for 3.5 days. To the reaction mixture was added water, which was made acidic with 1N-HCl, followed by extraction with ethyl acetate. The organic layer was washed with water, dried and concentrated to dryness. The concentrate was purified by column chromatography on silica gel. Crude crystals thus obtained were recrystallized from ethyl acetate methanol to afford colorless crystals (0.23 g, 41%), m.p. 224°–225° C.

| Elemental Analysis for $C_{27}H_{26}H_6O_2$: | | |
|---|---|---|
| C (%) | H (%) | N (%) |
| Calcd: 68.98; | 5.66; | 17.88 |
| Found: 68.89; | 5.68; | 17.66 |

$^1$H-NMR(200MHz,DMSO-d$_6$) δ: 0.87(3H,t), 1.26–1.45(2H,m), 1.63–1.78(2H,m), 2.85(2H,t), 3.85(3H,s), 5.62(2H,s), 7.00(2H,d), 7.07(2H,d), 7.48–7.70(5H,m), 7.82(1H,dd), 8.14(1H,s).
IR(KBr)cm$^{-1}$: 1725, 1460, 1450, 1435, 1340, 1265, 1235, 775, 760, 745.

REFERENCE EXAMPLE 50

2-Butyl-1-[[2'-(1H-tetrazol-5-yl)biphenyl-4-yl)methyl]-benzimidazole-6-carboxylic acid A solution of methyl 2-butyl-1-[2'-(1H-tetrazol-5-yl)biphenyl-4-yl)methyl]benzimidazole-6-carboxylate (0.1 g) in methanol (5 ml) containing 1 N NaOH (0.5 ml) was heated for 5 hours under reflux. The solvent was evaporated to dryness and to the residue was added 1N-HCl (0.5 ml), which was extracted with chloroform. The organic layer was washed with water, dried and concentrated to dryness. Crude crystals thus obtained were recrystallized from methanol - ethyl acetate to afford colorless crystals (60 mg, 58%), m.p. 258°–259° C.

| Elemental Analysis for $C_{27}H_{24}N_6O_2\cdot\frac{1}{2}$EtOAc: | | |
|---|---|---|
| C (%) | H (%) | N (%) |
| Calcd: 67.73; | 5.68; | 16.92 |
| Found: 67.79; | 5.50; | 16.89 |

$^1$H-NMR(200MHz,DMSO-d$_6$) δ: 0.87(3H,t), 1.27–1.45(2H,m), 1.63–1.79(2H,m), 2.85(2H,t), 5.60(2H,s), 7.00(2H,d), 7.08(2H,d), 7.48(5H,m), 7.84(1H,dd), 8.11(1H,s).
IR(KBr)cm$^{-1}$: 1730, 1460, 1410, 1335, 1285, 1265, 1225, 780, 760.

REFERENCE EXAMPLE 51

Methyl 2-amino-5-methylbenzoate

A mixture of 2-amino-5-methyl benzoic acid (10 g) in methanol (50 ml) containing conc. sulfuric acid (5.5 ml) was heated for 19 hours under reflux. The solvent was distilled off, and the residue was dissolved in water. The solution was neutralized with an aqueous sodium hydroxide, followed by extraction with ethyl acetate. The organic layer was dried and concentrated to afford a pale brown oil (8.1 g, 74%).

$^1$H-NMR(90MHz,CDCl$_3$) δ: 2.24(3H,s), 3.89(3H,s), 5.55(2H,s), 6.59(1H,d), 7.10(1H,dd), 7.68(1H,d).

REFERENCE EXAMPLE 52

Methyl 5-methyl-2-valerylaminobenzoate

To a solution of methyl 2-amino-5-methylbenzoate (8.1 g) and triethylamine (6.0 g) in methylene chloride (50 ml) was added dropwise, while stirring under ice-cooling, valeryl chloride (6.5 g). The reaction was allowed to stir for two hours, then the reaction mixture was washed with an aqueous solution of sodium carbonate, dilute hydrochloric acid and water, followed by drying. The solvent was evaporated to dryness to give a pale brown oil (12.8 g, 99%).

$^1$H-NMR(90MHz,CDCl$_3$) δ: 0.95(3H,t), 1.2–1.9(4H,m), 2.33(3H,s), 2.43(2H,t), 3.93(3H,s), 7.34(1H,dd), 7.82(1H,d), 8.62(1H,d).

REFERENCE EXAMPLE 53

Methyl 5-methyl-3-nitro-2-valerylaminobenzoate

To a mixture of methyl 5-methyl-2valerylaminobanzoate (12.8 g) in acetic anhydride (5.9 g) was added dropwise, while stirring under ice-cooling, fuming nitric acid (6.7 ml), followed by stirring for 3 hours. To the reaction mixture was added ice water, which was extracted with ethyl acetate. The extract was washed with an aqueous solution of sodium bicarbonate and water, which was then dried. The solvent was evaporated to dryness, and the residue was purified by column chromatography on silica gel. Crystals thus obtained were recrystallized from isopropyl ether gave colorless crystals (8.5 g, 60%), m.p. 59°–60° C.

$^1$H-NMR(200MHz,CDCl$_3$) : 0.94(3H,t), 1.31–1.50(2H,m), 1.63–1.78(2H,m), 2.43(2H,t), 3.95(3H,s), 7.90(1H,d), 8.00(1H,d), 10.16(1H,s).

REFERENCE EXAMPLE 54

Methyl 2-N-(2'-cyanobiphenyl-4-yl)methyl-N-valeryl]amino]-5-methyl-3-nitrobenzoate A mixture of methyl 5-methyl-3-nitro-2-valerylaminobenzoate (5.89 g), 4-(2-cyanophenyl)benzyl bromide (5.44 g) and potassium carbonate (3.0 g) in DMF (50 ml) was stirred for 15 hours at 50° C. To the reaction mixture was added water and it was extracted with ethyl acetate, and the organic layer was dried. The solvent was distilled off, and the residue was purified by column chromatography on silica gel. Crystals thus obtained were recrystallized from ethyl acetate - hexane to afford colorless crystals (3.1 g, 32%), m.p. 141°–142° C.

$^1$H-NMR(200MHz,CDCl$_3$) δ: 0.85(3H,t), 1.17–1.36(2H,m), 1.60–1.75(2H,m), 2.05–2.15(2H,m), 2.49(3H,s), 3.64(3H,s), 4.62(1H,d), 4.94(1H,d), 7.21(2H,d), 7.38–7.50(4H,m), 7.59–7.68(1H,m), 7.73–7.77(3H,m), 7.89(1H,m).

REFERENCE EXAMPLE 55

Methyl 2-butyl-1-(2'-cyanobiphenyl-4-yl)methyl-5-methylbenzimidazole-7-carboxylate To a solution of methyl 2-[[N-(2'-cyanobiphenyl-4-yl)methyl-N-valeryl]amino]-5-methyl-3-nitrobenzoate (3.1 g) in a mixture of conc. HCl (4.4 ml) and methanol (22 ml) was added, while stirring, iron powder (1.6 g) in portions. The mixture was heated for 7 hours under reflux. Insoluble materials were filtered off, and the filtrate was concentrated. To the concentrate was added water and this mixture was extracted with ethyl acetate. The organic layer was washed with an aqueous solution of sodium bicarbonate and water, followed by drying. The solvent was distilled off and the residue was purified by column chromatography on silica gel to afford a pale brown oil (2.8 g, quantitatively).

$^1$H-NMR(200MHz,CDCl$_3$) δ: 0.95(3H,t), 1.37–1.56(2H,m), 1.79–1.94(2H,m), 2.47(3H,s), 2.90(2H,t), 3.71(3H,s), 5.79(2H,s), 6.96(2H,d), 7.39–7.46(5H,m), 7.58–7.66(1H,m), 7.73–7.77(2H,m).

IR(neat)cm$^{-1}$: 2220, 1720, 1520, 1480, 1435, 1410, 1305, 1245, 1215, 1195, 1110, 1040, 780, 760.

REFERENCE EXAMPLE 56

Ethyl 2-amino-6-methylbenzoate

This compound was prepared according to the procedure for Reference Example 51. Oil (yield 82%).

$^1$H-NMR(90MHz, CDCl$_3$) δ: 1.34(3H,t), 2.43(3H,s), 4.35(2H,q), 5.06(2H,br s), 6.50(2H,d), 7.07(1H,t).

REFERENCE EXAMPLE 57

Ethyl 6-methyl-2-valerylaminobenzoate

This compound was prepared according to the procedure for Reference Example 52.

m.p. 56°–57° C. (yield 70%).

$^1$H-NMR(90MHz,CDCl$_3$) δ: 0.93(3H,t), 1.39(3H,t), 1.18–1.87(4H,m), 2.37(2H,t), 2.46(3H,s), 4.41(2H,q), 6.94(1H,d), 8.27(1H,d), 7.32(1H,t), 9.69(1H,br s).

REFERENCE EXAMPLE 58

Ethyl 6-methyl-3-nitro-2-valerylaminobenzoate

This compound was prepared according to the procedure for Reference Example 53.

m.p. 103°–104° C. (yield 52%).

$^1$H-NMR(90MHz,CDCl$_3$) δ: 0.93(3H,t), 1.35(3H,t), 1.17–1.85(4H,m), 2.38(2H,t), 2.49(3H,s), 4.38(2H,q), 7.14(1H,d), 7.97(1H,d).

REFERENCE EXAMPLE 59

Ethyl 6-methyl-3-nitro-2-[[2'-(N-triphenylmethyl-1H-tetrazol-5-yl)biphenyl-4-yl]methyl-N-valeryl]aminobenzoate This compound was prepared according to the procedure for Reference Example 54.

Oil (yield 80%).

$^1$H-NMR(200MHz,CDCl$_3$) δ: 0.86(3H,t), 1.34(3H,t), 1.20–1.45(2H,m), 1.60–1.78(2H,m), 2.14(2H,t), 2.40(3H,s), 4.09(1H,d), 5.28(1H,d), 4.23–4.42(2H,m), 6.81–6.96(10H,m), 7.19–7.53(13H,m), 7.69(1H,d), 7.88(1H,dd).

REFERENCE EXAMPLE 60

Methyl 2-amino-5-chlorobenzoate

To a solution of 2-amino-5-benzoic acid (25.5 g) in methanol (300 ml) was added conc. sulfuric acid (12 ml). The mixture was heated for 24 hours under reflux. The reaction mixture was concentrated and there was added water (300 ml), followed by neutralization with potassium carbonate. The mixture was extracted with ethyl acetate. The organic layer was washed with water and dried, then the solvent was distilled off to give crude crystals. Recrystallization from i-propyl ether - benzene gave pale yellow crystals (17.1 g, 63%), m.p. 68°–70° C.

REFERENCE EXAMPLE 61

Methyl 5-chloro-2-valerylaminobenzoate

To a solution of methyl 2-amino-5-chlorobenzoate (15 g) and triethylamine (12 ml) in methylene chloride (150 ml) was added dropwise, while stirring under ice-cooling, valeryl chloride (10 ml). The mixture was stirred at room temperature for further two hours. The reaction mixture was washed with an aqueous solution of sodium bicarbonate and water, followed by drying. The solvent was distilled off to afford a pale yellow crystals (13.4 g, 61%), m.p. 48°–49° C.

REFERENCE EXAMPLE 62

Methyl 5-chloro-3-nitro-2-valerylaminobenzoate

To a solution of methyl 5-chloro-2valerylaminobenzoate (13.4 g) in acetic anhydride (10 ml) was added dropwise, while stirring under ice-cooling, fuming nitric acid. The mixture was stirred for one hour at room temperature, then there was added ice water. The mixture was allowed to stand to give crystals Recrystallization from isopropyl ether afforded pale yellow crystals (9.5 g, 61%), m.p. 84°–85° C.

REFERENCE EXAMPLE 63

Methyl 5-chloro-2-[N-(2'-cyanobiphenyl-4-yl)methyl-N-valeryl]amino1-3-nitrobenzoate A mixture of methyl 5-chloro-3-nitro-2-valerylaminobenzoate (3.15 g), 4-(2-cyanophenyl)benzyl bromide (2.8 g) and potassium carbonate (1.8 g) in DMF (50 ml) was stirred for 3 hours at room temperature. The reaction mixture was concentrated to dryness, and the concentrate was extracted with ethyl acetate and H$_2$O. The organic layer was washed with water and dried. The solvent was distilled off to give crystals. Recrystallization from ethyl acetate - benzene afforded colorless crystals (4.0 g, 79%), 137°–138° C.

REFERENCE EXAMPLE 64

Methyl 5-chloro-3-nitro-2-[υ2'-(N-triphenylmethyl-1H-tetrazol-5-yl)biphenyl-4-yl]methyl-N-valeryl]aminobenzoate To a solution of methyl 5-chloro-3-nitro-2-valerylaminobenzoate (0.93 g) in DMF (10 ml) were added potassium carbonate (0.5 g) and N-triphenylmethyl-5-[2'-(4-bromomethyl)biphenylmethyl]tetrazole (1.84 g). The mixture was stirred for 19 hours at room temperature. To the reaction mixture was added water (50 ml) and the mixture was extracted with ethyl acetate. The organic layer was washed with water and dried, then the solvent was distilled off. The residue (3.8 g) was purified by column chromatography on silica gel to give pale yellow crystals (1.89 g, 82%).

$^1$H-NMR(200MHz,CDCl$^3$) δ: 0.86(3H,t), 1.17–1.35(2H,m), 1.56–1.80(2H,m), 2.03–2.10(2H,m), 3.63(3H,s), 4.41(1H,d), 4.82(1H,d), 6.76–6.98(10H,m), 7.20–7.54(12H,m), 7.88(1H,d), 7.90–7.93)1H,m), 7.98(1H,d).

IR(KBr)cm$^{-1}$: 1750, 1690, 1555, 1295, 1270, 1225, 760, 710.

REFERENCE EXAMPLE 65

Methyl 2-butyl-5-chloro-1-[(2'-cyanobiphenyl-4-yl)methylbenzimidazole-7-carboxylate To a solution of methyl 5-chloro-2-[N-(2'-cyanobiphenyl-4-yl)methyl-N-valeryl]amino-3nitrobenzoate (3.33 g) in a mixture of conc. HCl (4 ml) and methanol (50 ml) was added, while stirring at room temperature, iron powder (95% purity, 1.1 g) in portions. The mixture was stirred for 24 hours at 80° C. Then, insoluble materials were filtered off, and the filtrate was concentrated to dryness. The concentrate was subjected to extraction with ethyl acetate - water. The organic layer was washed with an aqueous solution of sodium bicarbonate and water, dried and concentrated. The solvent was distilled off, and the residue was purified by column chromatography on silica gel to afford colorless needles (1.83 g, 61%).

$^1$H-NMR(200MHz,CDCl$_3$) δ: 0.96(3H,t), 1.38–1.57(2H,m), 1.80–1.95(2H,m), 2.92(2H,t), 3.72(3H,s), 5.79(2H,s), 6.94(2H,d), 7.41–7.49(4H,m), 7.59–7.63(1H,m), 7.73–7.78(1H,m), 7.61(1H,d), 7.91(1H,d).

REFERENCE EXAMPLE 66

Ethyl 2-carboxy-3-nitrobenzoate

A solution of 3-nitrophthalic acid (35 g) in ethanol (300 ml) containing conc. sulfuric acid (20 ml) was heated for 24 hours under reflux. The solvent was distilled off, and the residue was poured into ice-water (700 ml), which was extracted with ethyl acetate. The organic layer was washed with water, which was extracted with an aqueous solution of potassium carbonate. The aqueous layer was made acidic with hydrochloric acid, followed by extraction with methylene chloride. The organic layer was washed with water and dried. The solvent was distilled off to give a solid product (29 g, 74%), which was used in the subsequent reaction without purification.

$^1$H-NMR(90MHz,CDCl$_3$) δ: 1.43(3H,t), 4.47(2H,q), 7.70(1H,t), 8.40(2H,d), 9.87(1H,br s).

IR(Nujol)cm$^{-1}$: 1725, 1535, 1350, 1300, 1270.

REFERENCE EXAMPLE 67

Ethyl 2-t-butoxycarbonylamino-3-nitrobenzoate

A mixture of ethyl 2-carboxy-3-nitrobenzoate (23.9 g) and thionyl chloride (12 ml) in benzene (150 ml) was heated for 3 hours under reflux. The resultant solution was concentrated to dryness to give the acid chloride (26 g, quantitatively), which was dissolved in methylene chloride (20 ml). The solution was added dropwise to a mixture of sodium azide (9.75 g) in DMF (20 ml) while stirring vigorously. The reaction mixture was poured into a mixture of ether-hexane (3 ml: 1,200 ml) and water (250 ml), and the whole mixture was shaken. The organic layer was washed with water and dried, followed by distilling off the solvent. The residue was dissolved in t-butanol (200 ml), and the temperature of the solution was raised, while stirring gradually, followed by heating for two hours under reflux. The reaction mixture was concentrated under reduced pressure to obtain an oil (30 g).

$^1$H-NMR(90MHz,CDCl$_3$) δ: 1.40(3H,t), 1.53(9H,s), 4.43(2H,q), 7.23(1H,t), 8.03–8.27(2H,m), 9.70(1H,br s).

IR(Neat)cm$^{-1}$: 3320, 2980, 1740, 1700, 1585, 1535, 1500, 1440, 1375, 1265, 1155.

REFERENCE EXAMPLE 68

Ethyl 2-[(2'-cyanobiphenyl-4-yl)methylamino-3-nitrobenzoate

To a solution of ethyl 2-t-butoxycarbonylamino-3-nitrobenzoate (20 g) in THF (50 ml) was added, while stirring under ice-cooling, sodium hydride (60% oil, 2.8 g). To the mixture were then added 4-(2cyanobiphenyl)methyl bromide (18 g) and potassium iodide (0.36 g), followed by stirring for 15 hours at room temperature. The reaction mixture was heated for 4 further hours under reflux. The solvent was distilled off, and the residue was extracted with water (250 ml) and ether (200 ml). The organic layer was concentrated to give a yellow oil, which was dissolved in a mixture of trifluoroacetic acid (60 ml) and methylene chloride (40 ml), and the solution was stirred for one hour at room temperature. The reaction mixture was concentrated to dryness and to the concentrate was added ethyl ether (200 ml) to give crystals. The crystals were collected by filtration, washed with ether and dried to afford pale yellow crystals (22.1 g, 85%), m.p. 119°–120° C.

$^1$H-NMR(90MHz,CDCl$_3$) δ: 1.37(3H,t), 4.23(2H,s), 4.37(2H,q), 6.37(1H,t), 7.33–7.83(9H,m), 7.97–8.20(2H,m).

IR(Nujol)cm$^{-1}$: 3280, 2220, 1690, 1575, 1530, 1480, 1450, 1255, 1125, 1105, 755.

REFERENCE EXAMPLE 69

Ethyl 3-amino-2-[(2'-cyanobiphenyl-4-yl)methyl]amino benzoate

To a solution of ethyl 2-[(2'-cyanobiphenyl-4-yl)methyl]amino-3-nitrobenzoate (5.5 g) in THF (50 ml) was added Raney nickel (5 g). Catalytic reduction was conducted at room temperature under atmospheric pressure. The catalyst was filtered off, and the filtrate was concentrated to give a yellow oil (5 g, quantitatively).

$^1$H-NMR(90MHz,CDCl$_3$–D$_2$O) δ: 1.30(3H,t), 4.23(2H,s), 4.27(2H,q), 6.87–7.03(2H,m), 7.33–7.87(9H,m).

IR(Neat)cm$^{-1}$: 3435, 3350, 2980, 1690, 1615, 1465, 1365, 1280, 1240, 1215, 1190, 1065, 755.

REFERENCE EXAMPLE 70

Ethyl 2-butyl-1-(2'-cyanobiphenyl-4-yl)methyl]benzimidazole-7-carboxylate

A solution of ethyl 3-amino-2-[(2'-cyanobiphenyl-4-yl)methyl]benzoate (0.31 g) and ethyl butyroimidate (0.18 g) in ethanol (2 ml) was stirred for 2 hours at 70° C. The reaction mixture was concentrated to dryness, and the concentrate was extracted with ethyl acetate and an aqueous solution of sodium bicarbonate. The organic layer was washed with water, dried and concentrated to give crystals. Recrystallization from ethyl acetate - hexane afforded pale yellow needles (0.22 g, 60%), m.p. 112°-114° C.

1H-NMR(90MHz,CDCl3) δ: 0.93(3H,t), 1.20(3H,t), 1.33-2.07(4H,m), 2.90(2H,t), 4.20(2H,q), 5.87(2H,s), 7.00(2H,d), 7.17-8.03(9H,m).

IR(Nujol)cm−1: 2220, 1725, 1480, 1450, 1420, 1400, 1285, 1255, 1245, 1190, 1110, 750.

REFERENCE EXAMPLE 71

2-Butyl-1-(2'-cyanobiphenyl-4-yl)methyl-7-hydroxymethylbenzimidazole

To a solution of methyl 2-butyl-1-[(2'-cyanobiphenyl-4-yl)methyl]benzimidazole-7-carboxylate (10 g) and NaBH. (2.2 g) in tetrahydrofuran (100 ml) was added dropwise methanol (19 ml) during 80 minutes. The mixture was heated for 27 further hours under reflux, and the reaction mixture was concentrated to dryness. To the concentrate was added water, which was neutralized with conc. HCl. Crystals thus separated were collected by filtration. Recrystallization from methanol afforded colorless needles (8.8 g, 93%), m.p. 203°-204° C.

| Elemental Analysis for $C_{26}H_{25}N_3O$: | | | |
|---|---|---|---|
| | C (%) | H (%) | N (%) |
| Calcd: | 78.96; | 6.37; | 10.62 |
| Found: | 79.24; | 6.36; | 10.69 |

NMR(200MHz,CDCl3) δ: 0.94(3H,t), 1.36-1.55(2H,m), 1.79-1.95(2H,m), 2.85(2H,t), 4.66(2H,d), 5.82(2H,s), 7.04(2H,d), 7.10(1H,dd), 7.18-726(1H,m), 7.40-7.52(4H,m), 7.64(1H,dt).

IR(KBr)cm−1: 3200, 2210, 1510, 1480, 1455, 1425, 1410, 1280, 1015, 765, 750.

REFERENCE EXAMPLE 72

2-Butyl-1-[(2'-cyanobiphenyl-4-yl)methyl-7-chloromethylbenzimidazole

To a solution of 2-butyl-1-[(2'-cyanobiphenyl-4yl)methyl]-7-hydroxybenzimidazole (5.4 g) and thionyl chloride (8.3 g) in chloroform (80 ml) was added a catalytic amount of DMF (one drop), then the mixture was heated for one hour under reflux. The reaction mixture was washed with an aqueous solution of sodium bicarbonate and water, followed by drying and concentration to dryness. The concentrate was crystallized from ethyl acetate - hexane to afford colorless needles (5.3 g, 92%), m.p. 144°-145° C.

| Elemental Analysis for $C_{26}H_{24}ClN_3$: | | | |
|---|---|---|---|
| | C (%) | H (%) | N (%) |
| Calcd: | 75.44; | 5.84; | 10.15 |
| Found: | 75.29; | 5.87; | 10.04 |

NMR(200MHz,CDCl3) δ: 0.96(3H,t), 1.38-1.57(2H,m), 1.82-1.97(2H,m), 2.88(2H,t), 4.60(2H,s), 5.78(s), 7.07(2H,d), 7.14(1H,dd), 7.21(1H,d), 7.41-7.54(4H,m), 7.60-7.69(1H,m), 7.75-7.84(2H,m).

IR(KBr)cm−1: 2210, 1515, 1480, 1450, 1425, 1400, 1350, 1280, 760, 745, 690.

REFERENCE EXAMPLE 73

2-Butyl-1-[(2'-cyanobiphenyl-4-yl)methyl]-7-cyanomethylbenzimidazole

A mixture of 2-butyl-1-[(2'-cyanobiphenyl-4-yl)methyl]-7-chloromethylbenzimidazole (0.83 g) and sodium cyanide (0.12 g) in DMF (10 ml) was stirred for 22 hours at room temperature. To the reaction mixture was added water and this mixture was extracted with ethyl acetate. The organic layer was washed with water and dried. The solvent was distilled off, and the residue was crystallized from ethyl acetate to givecolorless prisms (0.76 g, 94%), m.p. 180°-181° C.

| Elemental Analysis for $C_{27}H_{24}N_4$: | | | |
|---|---|---|---|
| | C (%) | H (%) | N (%) |
| Calcd: | 80.17; | 5.98; | 13.85 |
| Found: | 80.22; | 6.17; | 13.69 |

REFERENCE EXAMPLE 74

Ethyl[[2-butyl-1-(2'-cyanobiphenyl--4yl)methyl]benzimidazol-7-yl]acetate

A mixture of 2-butyl-1-[(2'-cyanobiphenyl-4-yl)methyl]-7-cyanomethylbenzimidazole (0.76 g) in 3.5N-hydrochloride in ethanol (10 ml) was heated for 2.5 hours under reflux. The reaction mixture was diluted with water, which was made basic with an aqueous solution of sodium bicarbonate, followed by extraction with ethyl acetate. The organic layer was washed with water and dried. The solvent was distilled off, and the residue was purified by column chromatography on silica gel to give a colorless oil (0.9 g, quantitatively).

NMR(200MHz,CDCl3) δ: 0.94(3H,t), 1.23(3H,t), 1.37-1.55(2H,m), 1.80-1.95(2H,m), 2.85(2H,t), 3.65(2H,s), 4.10(2H,q), 5.73(2H,s), 7.01-7.07(3H,m), 7.21(1H,t), 7.74-7.68(5H,m), 7.71-7.78(2H,m).

IR(neat)cm−1: 2210, 1730, 1510, 1475, 1435, 1400, 1365, 1350, 1275, 1040, 760, 735.

REFERENCE EXAMPLE 75

2-Butyl-1-(2'-cyanobiphenyl-4-yl)methyl)]-7-methylbenzimidazole

A mixture of 2-butyl-1-[(2'-cyanobiphenyl-4-yl)methyl]-7-chloromethylbenzimidazole (0.62 g), tributyltin hydride (3.0 g) and perbenzoic acid (catalytic amount) in toluene (20 ml) was heated for 5.5 hours under reflux in nitrogen atmosphere. The reaction mixture was concentrated, purified by column chromatography on silica gel and recrystallized from ethyl acetate - hexane to give colorless crystals (0.5 g, 88%), m.p. 115°-116° C.

| Elemental Analysis for $C_{26}H_{25}N_3$: | | | |
|---|---|---|---|
| | C (%) | H (%) | N (%) |
| Calcd: | 82.29; | 6.64; | 11.07 |
| Found: | 82.30; | 6.74; | 10.94 |

NMR(200MHz,CDCl3) δ: 0.93(3H,t), 1.35-1.53(2H,m), 1.77-1.92(2H,m), 2.51(3H,s), 2.82(2H,t), 5.64(2H,s), 6.94(1H,d), 7.05(2H,d), 7.15(1H,t), 7.41-7.53(4H,m), 7.60-7.68(2H,m), 7.76(1H,d).

IR(KBr)cm−1: 2210, 1595, 1515, 1480, 1460, 1415, 1400, 1345, 1280, 780, 760, 740.

REFERENCE EXAMPLE 76

2-Butyl-1-(2'-cyanobiphenyl-4-yl)methyl]-7-hydroxybenzimidazole

To a solution of 2-butyl-1-[(2'-cyanobiphenyl-4-yl)methyl]-7-methoxybenzimidazole (1.2 g) in methylene chloride (5 ml) was added boron tribromide (1.7 g) at −72 °C. in nitrogen atmosphere. The mixture was stirred for 8 hours at room temperature and there was added water, followed by stirring for further one hour. The reaction mixture was made basic with 6N NaOH, followed by extraction with ethyl acetate. The organic layer was washed with water, dried and concentrated. The concentrate was purified by column chromatography on silica gel. Crude crystals thus obtained were recrystallized from ethyl acetate - hexane to give colorless prisms (0.69, 63%), m.p. 185°–186° C.

| Elemental Analysis for $C_{25}H_{23}N_3O$: | | | |
|---|---|---|---|
| | C (%) | H (%) | N (%) |
| Calcd: | 78.71; | 6.08; | 11.02 |
| Found: | 78.70; | 6.07; | 11.01 |

$^1$H-NMR(200MHz,CDCl$^3$) δ: 0.81(3H,t), 1.22–1.42(2H,m), 1.66–1.81(2H,m), 2.80(2H,t), 5.81(2H,s), 6.71(1H,d), 7.00(1H,t), 7.19–7.26(3H,m), 7.38–7.50(4H,m), 7.61(1H,m), 7.74(4H,d).

IR(KBr)cm$^{-1}$: 2210, 1615, 1590, 1500, 1475, 1440, 1410, 1365, 1290, 1195, 1160, 1065, 780, 755, 725.

REFERENCE EXAMPLE 77

2-Methoxy-6-nitroaniline

A mixture of 2-amino-3-nitrophenol (7.7 g) and potassium carbonate (7.6 g) in DMF (15 ml) was stirred for 30 minutes at room temperature and there was then added methyl iodide (7.8 g). The mixture was stirred for 5 further hours at room temperature. To the reaction mixture was added water, which was extracted with ethyl acetate. The organic layer was washed with water and, then, dried. The solvent was distilled off to give crude crystals and recrystallization from isopropyl ether gave orange prisms (6.9 g, 82%), m.p. 76°–77° C.

REFERENCE EXAMPLE 78

N-(2-Methoxy-6-nitrophenyl)valeroamide

To a mixture of 2-methoxy-6-nitroaniline (5.9 g) in valeric anhydride (14 g) was added a catalytic amount of conc. sulfuric acid, which was stirred for 1.5 hour at 130°–140° C. To the reaction mixture was added water, which was made basic with 6N NaOH. The reaction mixture was extracted with ethyl acetate. The organic layer was washed with water and dried. The solvent was distilled off. The residue was purified by column chromatography on silica gel. Crude crystals thus obtained were recrystallized from ethyl acetate-hexane to give colorless crystals (3.2 g, 36%), m.p. 113°–114° C.

$^1$H-NMR(90MHz,CDCl$_3$) δ: 0.95(3H,t), 1.33–1.51(2H,m), 1.64–1.79(2H,m), 2.42(2H,t), 3.94(3H,s), 7.14(1H,dd), 7.26(1H,t), 7.51(1H,dd), 7.64(1H,brs).

IR(KBr)cm$^{-1}$: 3300, 1670, 1600, 1590, 1545, 1520, 1485, 1460, 1430, 1360, 1275, 1055, 800, 735.

REFERENCE EXAMPLE 79

N-(2'-Cyanobiphenyl-4-yl)methyl-N-(2-methoxy-6-nitrophenyl)valeramide

To a solution of N-(2-methoxy-6-nitrophenyl)valeramide (3.2 g) in DMF (15 ml) was added, under ice-cooling, sodium hydride (60% oil, 0.61 g). The mixture was stirred for 20 minutes and then there was added 4-(2-cyanophenyl)benzyl bromide (3.5 g), followed by stirring for one hour at room temperature. To the reaction mixture was added water, which was extracted with ethyl acetate. The organic layer was washed with water and dried. The solvent was distilled off, and the residue was purified by column chromatography on silica gel to give a yellow oil (5.8 g, quantitatively).

$^1$H-NMR(90MHz,CDCl$_3$) δ: 0.84(3H,t), 1.12–1.35(2H,m), 1.56–1.70(2H,m), 1.91–2.23(2H,m), 3.61(3H,s), 4.42(1H,d), 5.20(1H,d), 7.03–7.12(1H,m), 7.22(2H,d), 7.34–7.49(6H,m), 7.63(1H,m), 7.74(1H,d).

IR(Neat)cm$^{-1}$: 2220, 1670, 1535, 1480, 1390, 1275, 1050, 800, 760, 730.

REFERENCE EXAMPLE 80

2-Butyl-1-[(2'-cyanobiphenyl-4-yl)methyl-7-methoxybenzimidazole

To a solution of N-[(2'-cyanobiphenyl-4-yl)methyl]-N-(2-methoxy-6-nitrophenyl)valeramide (5.8 g) in methanol (50 ml) and conc. HCl (7 ml) was added, while stirring at room temperature, iron powder (2.3 g) in portions. The reaction mixture was heated for 5 hours under reflux, then the solvent was distilled off. To the residue were added ethyl acetate and water, which was made basic with 6N NaOH. Insoluble materials were filtered off, and the filtrate was allowed to form two layers. The organic layer was washed with water and dried, followed by removal of the solvent. The residue was recrystallized from ethyl acetate - hexane to afford colorless prisms (4.1 g, 80%), m.p. 127°–128° C.

$^1$H-NMR(200MHz,CDCl$_3$) δ: 0.91(3H,t), 1.32–1.51(2H,m), 1.73–1.89(2H,m), 2.79(2H,t), 3.83(3H,s), 5.71(2H,s), 6.69(1H,d), 7.11–7.19(3H,m), 7.38–7.51(5H,m), 7.63(1H,m), 7.76(1H,d).

IR(KBr)cm$^{-1}$: 2210, 1605, 1585, 1505, 1480, 1460, 1445, 1420, 1400, 1280, 1255, 1090, 770, 720.

REFERENCE EXAMPLE 81

2-Butyl-1-(2'-cyanobiphenyl-4-yl)methyl]-7-methoxymethylbenzimidazole

A mixture of 2-butyl-1-[(2'-cyanobiphenyl-4-yl)methyl]-7-hydroxymethylbenzimidazole (0.79 g), thionyl chloride (0.36 g) and DMF (catalytic amount) in chloroform (20 ml) was heated for one hour under reflux. The solvent was distilled off and the residue was dissolved in methanol (15 ml). To the solution was added sodium methoxide (4.9 M methanol solution, 2 ml), followed by heating for 6 hours under reflux. The solvent was distilled off. To the residue was added water, followed by extraction with ethyl acetate. The organic layer was washed with water and dried, followed by evaporation of the solvent. The residue was purified by column chromatography on silica gel to give an oil (0.48 g, 59%).

$^1$H-NMR(90MHz,CDCl$_3$) δ: 0.92(3H,t), 1.20–2.05(4H,m), 2.84(2H,t), 3.30(3H,s), 4.34(2H,s), 5.74(2H,s), 6.90–7.90(11H,m).

IR(neat)cm$^{-1}$: 2220, 1520, 1480, 1460, 1440, 1425, 1280, 1190, 760.

The following compounds (Reference Examples 82–84) were prepared according to the procedure for Reference Example 32.

REFERENCE EXAMPLE 82

Ethyl 2-[N-acetyl-N-(2′-cyanobiphenyl-4-yl)methylamino-3-nitrobenzoate

Oil $^1$H-NMR(90 MHz,CDCl$_3$) δ: 1.30(3H,t), 1.97(3H,s), 4.17(1H,d), 4.83(1H,d), 7.17–8.17(11H,m),

IR(Neat)cm$^{-1}$: 2985, 2230, 1730, 1675, 1600, 1540, 1390, 1365, 1285, 770.

REFERENCE EXAMPLE 83

Ethyl 2-N-propionyl-N-(2′-cyanobiphenyl-4-yl)methylamino-3-nitrobenzoate

Oil.

$^1$H-NMR(90MHz,CDCl$_3$) δ: 1.13(3H,t), 1.27(3H,t), 2.17(2H,q), 4.13(2H,q), 4.77(1H,d), 4.83(1H,d), 7.10–8.17(11H,m).

IR(Neat)cm$^{-1}$: 2985, 2220, 1730, 1675, 1600, 1535, 1480, 1445, 1390, 1350, 1290, 1265, 1210, 770.

REFERENCE EXAMPLE 84

Ethyl 2-[N-isobutylyl-N-(2′-cyanobiphenyl-4-yl)methyl]amino-3-nitrobenzoate

Oil.

$^1$H-NMR(900MHz,CDCl$_3$) δ: 1.07(3H,d), 1.13(3H,d), 1.30(3H,t), 2.03–2.47(1H,m), 4.20(2H,q), 4.70(1H,d), 5.13(1H,d), 7.17–8.27(1H,m).

IR(Neat)cm$^{-1}$: 2980, 2220, 1730, 1670, 1590, 1530, 1480, 1390, 1350, 1285, 1260, 1240, 1205, 765.

The following compounds (Reference Examples 85–87) were prepared according to the procedure for Reference Example 33.

REFERENCE EXAMPLE 85

Ethyl 1-[(2′-cyanobiphenyl-4-yl)methyl]-2-methylbenzimidazole-7-carboxylate m.p. 167°–168° C. (yield 81%).

$^1$H-NMR(90MHz,CDCl$_3$) δ: 1.20(3H,t), 2.63(3H,s), 4.20(2H,q), 5.83(2H,s), 7.00(2H,d), 7.17–7.97(9H,m).

IR(Neat)cm$^{-1}$: 2220, 1705, 1395, 1280, 1265, 1210.

REFERENCE EXAMPLE 86

Ethyl 1-[(2′-cyanobiphenyl-4-yl)methyl]-2-ethylbenzimidazole-7-carboxylate m.p. 163°–164° C. (yield 76%).

$^1$H-NMR(90MHz,CDCl$^3$) δ: 1.20(3H,t), 1.47(3H,t), 2.93(2H,q), 4.20(2H,q), 5.83(2H,s), 6.97(2H,d), 7.17–8.00(9H,m).

IR(Nujol)cm$^{-1}$: 2220, 1720, 1480, 1450, 1420, 1400, 1380, 1280, 1250, 1200, 1145, 1110.

REFERENCE EXAMPLE 87

Ethyl 1-(2′-cyanobiphenyl-4-yl)methyl-2′-isopropylbenzimidazole-7-carboxylate m.p. 107°–108° C. (yield 77%).

$^1$H-NMR(90MHz,CDCl$_3$) δ: 1.17(3H,t), 1.43(6H,d), 3.03–3.47(1H,m), 4.17(2H,q), 5.87(2H,s), 6.93(2H,d), 7.17–7.80(8H,m), 7.97(1H,d).

IR(Nujol)cm$^{-1}$: 2220, 1730, 1440, 1400, 1280, 1250, 1205, 1140, 1110, 765, 740.

REFERENCE EXAMPLE 88

Ethyl 2-chloromethyl-1-(2′-cyanobiphenyl-4-yl)methyl]benzimidazole-7-carboxylate To an ice-cooled solution of ethyl 3-amino-2-[(2′-cyanobiphenyl-4-yl)methyl]aminobenzoate (1.0 g) and triethylamine (0.3 g) in methylenechloride (10 ml) was added chloroacetyl chloride (0.24 ml) in portions. The mixture was allowed to stir for 13 hours and then evaporated to dryness to give a residue. The residue was washed with H$_2$O, dried and dissolved in EtOH (10 ml). To the solution was added conc-HCl (1 ml) and the solution was refluxed for 6 hours. The reaction solution was evaporated to dryness to give a residue and the residue was dissolved in methylene chloride and water. The solution was made basic with 1N-NaOH and the organic layer was washed with water, dried and evaporated to dryness to give crystals. Recrystallization from ethyl acetate-isopropylether gave colorless crystals. (0.88 g, 76%)

$^1$H-NMR(200MHz,CDCl$_3$) δ: 1.21(3H,t), 4.21(2H,q), 4.83(2H,s), 6.02(2H,s), 7.02(2H,d), 7.29–7.49 (5H,m), 7.58–7.79(3H,m), 8.00 (1H,dd).

REFERENCE EXAMPLE 89

Ethyl 1-(2′-cyanobiphenyl-4-yl)methyl]-2-methoxymethylbenzimidazole-7-carboxylate A solution of ethyl 2-chloromethyl-1-[(2-cyanobiphenyl-4-yl)methyl]-benzimidazole-7-carboxylate (0.8 g) and NaOMe (1.08 g, 28% solution in methanol) in methanol (15 ml) was refluxed for 2 hours. The reaction solution was evaporated to dryness to give a residue and the residue was dissolved in CH$_2$Cl$_2$-H$_2$O. The organic layer was washed with H$_2$O, dried and evaporated to dryness to give a syrup. The syrup was purified by column chromatography on silica gel to give a yellow syrup (0.4 g, 52%).

$^1$H-NMR(200MHz,CDCl$^3$) δ: 3.43(3H,s), 3.72(3H,s), 4.78(2H,s), 5.97(2H,s), 6.99(2H,d), 7.25–7.49(5H,m), 7.55–7.77(3H,m), 7.99(1H,dd).

The following compounds (Reference Examples 90–93) were prepared by a method like that of Reference Example 89.

REFERENCE EXAMPLE 90

Ethyl 1-[(2′-cyanobiphenyl-4-yl)methyl-2-ethoxymethylbenzimidazole-7-carboxylate pale brown syrup (92%).

$^1$H-NMR(200MHz,CDCl$^3$) δ: 1.16(3H,t), 1.23(3H,t), 3.59(2H,q), 4.21(2H,q), 4.82(2H,s), 5.99(2H,s), 6.99(2H,d), 7.24–7.45(5H,m), 7.55–7.75(3H,m), 7.98(1H,dd).

REFERENCE EXAMPLE 91

Ethyl 1-[(2′-cyanobiphenyl-4-yl)methyl]-2-methylthiomethylbenzimidazole-7-carboxylate pale yellow syrup (72%).

¹H-NMR(200MHz,CDCl₃) δ: 1.20(3H,t), 2.18(3H,s), 3.90(2H,s), 4.20(2H,q), 5.96(2H,s), 7.01(2H,d), 7.23–7.35(1H,m), 7.37–7.50(4H,m), 7.59–7.80(3H,m), 7.97(1H,dd).

REFERENCE EXAMPLE 92

Ethyl 1-(2'-cyanobiphenyl-4-yl)methyl]-2-ethylthiomethyl-benzimidazole-7-carboxylate pale brown syrup (88%).

¹H-NMR(200MHz,CDCl₃) δ: 1.20(3H,t), 1.27(3H,t), 2.62(2H,q), 3.96(2H,s), 4.20(2H,q), 6.00(2H,s), 7.01(2H,d), 7.29(1H,t), 7.38–7.49(4H,m), 7.57–7.78(3H,m), 7.96(1H,dd).

REFERENCE EXAMPLE 93

Ethyl 2-acetoxymethyl-1-[(2'-cyanobiphenyl-4-yl)methyl]benzimidazole-7-carboxylate pale brown syrup (99%).

REFERENCE EXAMPLE 94

Methyl 3-amino-2-[(2'-cyanobiphenyl-4-yl)methyl]aminobenzoate

A mixture of ethyl 3-amino-2-[(2'-cyanobiphenyl-4-yl)methyl]aminobenzoate (5g) and NaH (60% oil, 1.62 g) in methanol (50 ml) was stirred at room temperature for 24 hours. The reaction mixture was concentrated to dryness to give a syrup, which was poured into saturated aqueous NaHCO₃ solution (100 ml). The mixture was extracted with chloroform and the organic layer was washed with H₂O, dried and evaporated to dryness to give a crystalline product. Recrystallization from ethyl acetate-hexane gave colorless crystals (3.9 g, 82%), m.p. 106°–108° C.

¹H-NMR(200MHz,CDCl³) δ: 3.81(3H,s), 3.97(2H,br s) 4.23(2H,s), 6.40(1H,br s), 6.88–6.91 (2H,m), 7.34–7.55(7H,m), 7.64(1H,dt), 7.77(1H,dd).

IR (KBr) cm⁻¹: 3410, 3350, 2225, 1695, 1485, 1470, 1290, 1200, 780, 760.

REFERENCE EXAMPLE 95

Methyl 2-(2-chloroethyl)-1-(2'-cyanobiphenyl-4-yl)methyl]benzimidazole-7-carboxylate To a cold solution of methyl 3-amino-2-[(2'-cyanobiphenyl-4-yl)methyl]aminobenzoate (0.5 g) in CH₂Cl₂ (5 ml) was added 3-chloropropionyl chloride (0.15 ml) dropwise. The reaction mixture was stirred at room temperature for 30 minutes and then concentrated to dryness to give a residue. The residue was dissolved in methanol (5 ml) containing conc. HCl (0.5 ml) and the solution was stirred at room temperature for 16 hours. The reaction solution was concentrated to dryness to give a residue, which was dissolved in CH₂Cl₂-H₂O. The aqueous layer was made basic and then extracted. The organic layer was washed with H₂O, dried and evaporated to dryness to give a pale brown syrup (0.7 g, 100%).

¹H-NMR(200MHz,CDCl₃) δ: 3.37(2H,t), 3.74(3H,s), 4.09(2H,t), 5.87(2H,s), 7.00(2H,d), 7.29(1H,t), 7.39–7.81(7H,m), 7.97(1H,dd).

REFERENCE EXAMPLE 96

Methyl 1-(2'-cyanobiphenyl-4-yl)methyl]-2-(2-methoxyethyl)-benzimidazole-7-carboxylate A mixture of methyl 2-(2-chloroethyl)-1-[(2'-cyanobiphenyl-4-yl)methyl]benzimidazole-7-carboxylate (1.0 g) and K₂CO₂ (0.25 g) in methanol (30 ml) was refluxed for 2 hours. The reaction mixture was concentrated to dryness to give a residue. The residue was dissolved in CH₂Cl₂ and an insoluble material was filtered off. The filtrate was concentrated to dryness and a resulting syrup was purified by column chromatography on silica gel to give a pale yellow syrup (0.45 g, 59%).

¹H-NMR(200MHz,CDCl₃) δ: 3.19(2H,t), 3.34(3H,s), 3.72(3H,s), 3.92(2H,t), 5.88(2H,s), 7.00(2H,d), 7.26(1H,t), 7.40–7.48(4H,m), 7.56–7.76(3H,m), 7.95(1H,dd).

REFERENCE EXAMPLE 97

Methyl 1-[(2'-cyanobiphenyl-4-yl)methyl]-2-(2-methylthiomethyl)benzimidazole-7-carboxylate This compound was prepared by a method like that of Reference Example 96.

colorless powder (1.1 g, 93%).

¹H-NMR(200MHz,CDCl₃) δ: 2.14(3H,s), 3.02–3.11(2H,m), 3.16–3.25(2H,m), 3.74(3H,s), 5.86(2H,s), 7.00(2H,d), 7.28(1H,t), 7.39–7.49(4H,m), 7.58–7.78(3H,m), 7.97(1H,dd).

REFERENCE EXAMPLE 98

2-Butyl-1-(2'-cyanobiphenyl-4-yl)methyl]-7-(N,N-dimethylaminoethyl)benzimidazole A mixture of 2-butyl-1-[(2'-cyanobiphenyl-4-yl)methyl]-7-chloromethylbenzimidazole (0.65 g) and dimethylamine (50% aqueous solution, 1.5 ml) in ethanol (3 ml) was heated in a sealed tube for 5 hours. The reaction solution was concentrated to dryness and a resulting syrup was dissolved in ethyl acetate. The solution was washed with water, dried and evaporated to dryness to give a syrup, which was purified by column chromatography on silica gel to give a colorless syrup 0.4 g, 63%).

¹H-NMR(200MHz,CDCl₃) δ: 0.92(3H,t), 1.35–1.53(2H,m), 1.81–1.94(2H,m), 2.16(6H,s), 2.80(2H,t), 3.34(2H,s), 6.00(2H,s), 6.95–7.01(3H,m), 7.16(1H,t), 7.39–7.50(4H,m), 7.62(1H,m), 7.73–7.77(2H,m).

IR (Neat) cm⁻¹: 2210, 1515, 1480, 1460, 1440, 1405, 1360, 1330, 1275, 1005, 840, 785, 760.

REFERENCE EXAMPLE 99

Ethyl 1-(2'-cyanobiphenyl-4-yl)methyl -2-secbutylbenzimidazole-7-carboxylate

A mixture of ethyl 3-amino-2-[(2'-cyanobiphenyl-4-yl)methyl]aminobenzoate (1.1 g) and 2-methylbutyric anhydride (0.56 g) in pyridine (2 ml) was heated at 115° C. for 15 hours. The reaction mixture was digested with ethyl acetate (50 ml) and the solution was washed with water, dried and evaporated to dryness to give a syrup. The syrup was dissolved in ethanol (15 ml) containing conc. HCl (0.5 ml) and the solution was refluxed for 3 hours. After removal of the solvent, the resulting syrup was purified by column chromatography on silica gel to afford a pale yellow syrup (1.2 g, 92%).

$^1$H-NMR(90MHz,CDCl$_3$) δ: 0.90(3H,t), 1.20(3H,t), 1.40(3H,d), 1.50-2.10(1H,m), 4.17(2H,q), 5.87(2H,s), 6.97(2H,d), 7.17-8.03(9H,m).

IR (Neat) cm$^{-1}$: 2975, 2930, 2875, 2220, 1480, 1445, 1410, 1370, 1280, 1260, 1200, 1140, 1110, 1035, 760.

REFERENCE EXAMPLE 100

Ethyl 1-[(2'-cyanobiphenyl-4-yl)methyl-2-isobutylbenzimidazole-7-carboxylate

This compound was prepared by a method similar to that of Reference Example 99.

a pale yellow syrup (quant.)

$^1$H-NMR(90MHz,CDCl$^3$) δ: 1.03(6H,d), 1.20(3H,t), 2.07-2.53(1H,m), 2.80(2H,d), 4.17(2H,q), 5.83(2H,s), 6.93(2H,d), 7.13-8.00(9H,m).

IR (Neat) cm$^{-1}$: 2960, 2215, 1710, 1480, 1400, 1280, 1255, 1200, 1120, 760.

REFERENCE EXAMPLE 101

2-Butyl-1-2'-(N-triphenylmethyltetrazol-5-yl)biphenyl-4-yl]methyl]benzimidazole-7-carboxylic acid A mixture of 2-butyl-1-[[2'-(1H-tetrazol-5-yl)biphenyl-4-yl]methyl]benzimidazole-7-carboxylic acid (3.0 g), triphenylmethyl chloride (1.96 g) and triethylamine (1.0 ml) in CH$_2$Cl$_2$ (20 ml) was stirred at room temperature for 16 hours. The reaction solution was washed with H$_2$O, dried over Na$_2$SO$_4$ and concentrated to dryness to give a solid residue. The residue was purified by column chromatography on silica gel to give a colorless powder (4.25 g, 91%), m.p. 120°-123° C.

$^1$H-NMR(200MHz,CDCl$^3$) δ: 0.88 (3H,t), 1.26-1.45(2H,m), 1.72-1.88(2H,m), 2.81(2H,t), 5.72(2H,s), 6.63(2H,d), 6.92-6.97(8H,m), 7.12-7.43(13H,m), 7.68(1H,d), 7.78-7.83(1H,m), 7.92(1H,d).

IR (Neat) cm$^{-1}$: 3050, 2950, 2925, 1690, 1595, 1510, 1490, 1440, 1405, 1275, 1240, 1180, 740, 690.

WORKING EXAMPLE 1

2-Butyl-1-[[2'-(1H-tetrazol-5-yl)biphenyl-4-yl]methyl]-benzimidazole-7-carboxylic acid A mixture of methyl 2-butyl-1-[(2'-cyanobiphenyl-4-yl)methyl]benzimidazole-7-carboxylate (3.2 g), sodium azide (7.4 g) and ammonium chloride (6.1 g) in DMF (30 ml) was stirred for 4 days at 115° C. To the reaction mixture was added water, which was adjusted to pH 3-4 with 1N-HCl. Resulting crude crystals (1) were purified by column chromatography on silica gel. The crystals thus obtained were recrystallized from ethyl acetate - methanol to afford colorless prisms (2.27 g, 63%), m.p. 168°-169° C.

| Elemental Analysis for C$_{26}$H$_{24}$N$_6$O$_2$.H$_2$O: | | | |
|---|---|---|---|
| | C (%) | H (%) | N (%) |
| Calcd: | 66.37; | 5.57; | 17.86 |
| Found: | 66.04; | 5.69; | 17.58 |

$^1$H-NMR(200MHz,DMSO-d$_6$) δ: 0.88(3H,t), 1.28-1.46(2H,m), 1.65-1.80(2H,m), 2.82(2H,t), 5.85(2H,s), 6.79(2H,d), 7.00(2H,d), 7.24(1H,t), 7.45(5H,m), 7.83(1H,dd).

IR(KBr)cm$^{-1}$: 1720, 1600, 1510, 1455, 1285, 1255, 1240, 775, 755, 745.

WORKING EXAMPLE 2

2-Butyl-1-2'-(N-methyltetrazol-5-yl)biphenyl-4-yl]methyl]benzimidazole-7-carboxylic acid The crude crystal (1) obtained in Working Example 1 was purified by column chromatography on silica gel, followed by recrystallization from ethyl acetate hexane to give colorless needles (0.17 g, 4.7%), m.p. 133°-135° C.

| Elemental Analysis for C$_{27}$H$_{26}$N$_6$O$_2$: | | | |
|---|---|---|---|
| | C (%) | H (%) | N (%) |
| Calcd: | 69.51; | 5.62; | 18.01 |
| Found: | 69.47; | 5.66; | 17.92 |

$^1$H-NMR(200MHz,CDCl$_3$) δ: 0.94(3H,t), 1.35-1.55(2H,m), 1.78-1.93(2H,m), 2.96(2H,t), 3.15(3H,s), 5.82(2H,s), 6.81(2H,d), 6.97(2H,d), 7.25(1H,t), 7.48-7.67(4H,m), 7.80(1H,dd), 7.95(1H,dd).

IR(KBr)cm$^{-1}$: 1715, 1520, 1415, 1290, 1260, 1200, 1125, 780, 750.

WORKING EXAMPLE 3

2-Butyl-N-isopropyl-1-[2'-(1H-tetrazol-5-yl)biphenyl-4-yl]methyl]benzimidazole-7-carboxamide A solution of 2-butyl-1-[[2'-(1H-tetrazol-5-yl)biphenyl-4-yl]methyl]benzimidazole-7-carboxylic acid (0.71 g) and diethyl cyanophosphate (purity 90%, 0.82 g) in DMF (6 ml) was stirred for one hour under ice-cooling. To the solution were then added isopropylamine hydrochloride (0.14 g) and triethylamine (0.61 g), and the mixture was stirred for 2 hours at room temperature. To the reaction mixture was added water, which was neutralized with 1N-HCl, followed by extraction with ethyl acetate. The organic layer was washed with water, dried and, then concentrated to dryness. Recrystallization of thus-obtained crude crystals from methanol - ethyl acetate gave colorless prisms (0.31 g, 41%), m.p. 247°-249° C.

| Elemental Analysis for C$_{29}$H$_{32}$N$_7$O.1/5H$_2$O: | | | |
|---|---|---|---|
| | C (%) | H (%) | N (%) |
| Calcd: | 69.91; | 6.55; | 19.68 |
| Found: | 69.91; | 6.30; | 19.87 |

$^1$H-NMR(200MHz,DMSO-d$_6$) δ: 0.87(3H,t), 0.93(6H,d), 1.26-1.44(2H,m), 1.62-1.77(2H,m), 2.80(2H,t), 3.85-3.95(1H,m), 5.67(2H,s), 6.84(2H,d), 6.99(2H,d), 7.16-7.24(2H,m), 7.44(1H,d), 7.51-7.72(4H,m), 8.27(1H,d).

IR(KBr)cm$^{-1}$: 1640, 1540, 1510, 1455, 1415, 755, 740.

WORKING EXAMPLE 4

2-Butyl-1-[[2'-(1H-tetrazol-5-yl)biphenyl-4-yl]methyl]-benzimidazole-7-carboxylic acid 2-sodium salt 2-Butyl-1-[2'-(1H-tetrazol-5-yl)biphenyl-4-yl]methyl-benzimidazole-7-carboxylic acid (0.2 g) was added to methanol (15 ml) containing NaOMe (46 mg), and the mixture was stirred for 15 minutes at room temperature. To the reaction mixture was added toluene (30 ml) and the mixture was concentrated under reduced pressure to give crystals. The crystals separated out were collected by filtration to give colorless powdery crystals (0.14 g, 62%), m.p. 255°–257 °C. (decomp.).

| Elemental Analysis for $C_{26}H_{22}N_6Na_2O_2 \cdot 2H_2O$: | | | |
|---|---|---|---|
| | C(%) | H(%) | N(%) |
| Calcd: | 58.64; | 4.92; | 15.78 |
| Found: | 58.98; | 4.60; | 15.66 |

$^1$H-NMR(200MHz,DMSO-d$_6$) δ: 0.85(3H,t), 1.27–1.39(2H,m), 1.59–1.74(2H,m), 2.69(2H,t), 6.10(2H,s), 6.81(2H,d), 6.98–7.07(3H,m), 7.19–7.53(6H,m)

IR(KBr)cm$^{-1}$: 1610, 1410, 1360, 760.

WORKING EXAMPLE 5

Butyl 2-butyl-1-[[2'-(1H-tetrazol-5-yl)biphenyl-4-yl]methyl]-benzimidazole-7-carboxylate A mixture of 2-butyl-1-[[2'-(1H-tetrazol-5-yl)biphenyl-4-yl]methylbenzimidazole-7-carboxylic acid (0.47 g) and conc. sulfuric acid (0.1 ml) in butanol (10 ml) were heated for 66 hours under reflux. The solvent was removed by evaporation. To the residue was added water and the mixture was adjusted to pH 3 to 4 with 1N-NaOH, followed by extraction with ethyl acetate. The organic layer was washed with water and dried. After removal of the solvent, the residue was purified by column chromatography on silica gel. Recrystallization from ethyl acetate - hexane afforded colorless prisms (0.15 g, 29%), m.p. 192°–193° C.

| Elemental Analysis for $C_{30}H_{32}N_6O_2$: | | | |
|---|---|---|---|
| | C(%) | H(%) | N(%) |
| Calcd: | 70.84; | 6.34; | 16.52 |
| Found: | 70.99; | 6.46; | 16.25 |

$^1$H-NMR(200MHz,CDCl$_3$) δ: 0.83(3H,t), 0.85(3H,t), 1.18–1 39(4H,m), 1.45–1.64(4H,m), 2.38(2H,t), 3.99(2H,t), 5.50(2H,s), 6.47(2H,d), 6.79(2H,d), 6.93(1H,d), 7.04(1H,t), 7.27–7.32(1H,m), 7.50(1H,dd), 7.56–7.68(2H,m), 7.97–8.01(1H,m).

IR(KBr)cm$^{-1}$: 1710, 1465, 1455, 1415, 1280, 1265, 1125, 760.

WORKING EXAMPLE 6

(4-Pyridyl)methyl 2-butyl-1-[[2'-(1H-tetrazol-5-yl)biphenyl-4-yl]methyl]-benzimidazole-7-carboxylate A solution of (4-pyridyl)methyl 2-butyl-1-[(2'-cyanobiphenyl-4-yl)methyl]benzmidazole-7-carboxylate (0.61 g) and trimethyltin azide (0.75 g) in toluene (10 ml) was heated for 4 days under reflux in nitrogen atmosphere. After removal of the solvent, the resulting solvent residue was dissolved in ethanol (5 ml). To the solution was added 1N-HCl (8 ml), and the mixture was stirred for 5 minutes at room temperature and this mixture was neutralized with 1N NaOH, followed by extraction with ethyl acetate. The extract was washed with water, dried, and evaporated to dryness. The resulting residue was purified by column chromatography on silica gel to give crystals. Recrystallization from ethyl acetate - hexane afforded colorless prisms (0.54 g, 83%), m.p. 179°–180° C.

| Elemental Analysis for $C_{32}H_{29}N_7O_2$: | | | |
|---|---|---|---|
| | C(%) | H(%) | N(%) |
| Calcd: | 70.70; | 5.38; | 18.04 |
| Found: | 70.96; | 5.45; | 18.02 |

$^1$H-NMR(200MHz,CDCl$_3$) δ: 0.80(3H,t), 1.18–1.36(2H,m), 1.53–1.68(2H,m), 2.49(2H,t), 5.19(2H,s), 5.51(2H,s), 6.44(2H,d), 6.79(2H,d), 7.15–7.31 (4H,m), 7.47–7.61(3H,m), 7.67(1H,dd), 7.92(1H,dd), 8.35(2H,d).

IR(KBr)cm$^{-1}$: 1720, 1600, 1410, 1280, 1250, 1120, 760, 750, 740.

WORKING EXAMPLE 7

2-Propyl-1-[[2'-(1H-tetrazol-5-yl)biphenyl-4-yl]methyl-benzimidazole-7-carboxylic acid A mixture of methyl 2-propyl-1-[(2'-cyanobiphenyl-4-yl)methyl]benzimidazole-7-carboxylate (2.5 g), sodium azide (3.9 g) and ammonium chloride (3.2 g) in DMF (30 ml) was stirred for 5 days at 110° C.-120° C. To the reaction mixture was added water and the solution was made acidic (pH 3–4), followed by extraction with ethyl acetate. The organic layer was washed with water and dried. After removal of the solvent, the residue was purified by column chromatography on silica gel to give crystals. Recrystallization from DMF-ethanol afforded colorless crystals (0.8 g, 23%), m.p. 275°–276° C. (decomp.).

| Elemental Analysis for $C_{25}H_{22}N_6O_2 \cdot \frac{1}{2}H_2O$: | | | |
|---|---|---|---|
| | C(%) | H(%) | N(%) |
| Calcd: | 67.10; | 5.18; | 18.78 |
| Found: | 67.19; | 4.95; | 18.84 |

$^1$H-NMR(90MHz,CDCl$^3$-CF$_3$COOH) δ: 1.10(3H,t), 1.70–2.20(2H,m), 3.23(2H,t), 5.97(2H,s), 6.90(2H,d), 7.13(2H,d), 7.47–7.80(5H,m), 8.03–8.17(2H,m).

IR(KBr)cm$^{-1}$: 3070, 2720, 2440, 1700, 1450, 1410, 1405, 1285, 1235, 1200, 1190, 1120, 755.

WORKING EXAMPLE 8

2-Pentyl-1-[[2'-(1H-tetrayol-5-yl)biphenyl-4-yl]methyl-benzimidazole-7-carboxylic acid A mixture of methyl 1-[(2'-cyanobiphenyl-4-yl)methyl]-2-pentylbenzimidazole-7-carboxylate (3.25 g), sodium azide (2.6 g) and ammonium chloride (2.1 g) in DMF (20 ml) was stirred for 5 days at 110 - 120° C. To the reaction mixture was added water, which was made acidic, (pH 3–4) with 1N-HCl, followed by extraction with ethyl acetate. The organic layer was washed with water and dried. After removal of the solvent, the residue was purified by column chromatography on silica gel to give crystals. Recrystallization from ethyl acetate - ethanol, followed by treatment with hot water, afforded colorless powdery crystals (1.0 g, 29%), m.p. 205°–207° C. (decomp.).

| Elemental Analysis for $C_{27}H_{26}N_6O_2 \cdot 1/5H_2O$: | | | |
|---|---|---|---|
| | C(%) | H(%) | N(%) |
| Calcd: | 68.98; | 5.66; | 17.88 |
| Found: | 69.14; | 5.60; | 17.90 |

¹H-NMR(90MHz,CDCl₃CF₃COOH) δ: 0.87(3H,t), 1.13–1.53(4H,m), 1.67–2.10(2H,m), 3.27(2H,t), 6.00(2H,s), 6.93(2H,d), 7.17(2H,d), 7.47–7.90(5H,m), 8.07–8.20(2H,m).

IR(Nujol)cm⁻¹: 3040, 2775, 1695, 1485, 1450, 1425, 1410, 1290, 1240, 1200, 755.

WORKING EXAMPLE 9

Methyl 2-butyl-5-methyl-1-[2'-(1H-tetrazol-5-yl)methylbenzimidazole-7-carboxylate A mixture of methyl 2-butyl-1-[(2'-cyanobiphenyl-4-yl)methyl]-5-methylbenzimidazole-7-carboxylate (2.8 g), sodium azide (6.2 g) and ammonium chloride (5.1 g) in DMF (25 ml) was stirred for 3 days at 110°–120° C. The reaction mixture was diluted with water, which was made acidic (pH 3–4) with 1N HCl, followed by extraction with ethyl acetate. The organic layer was washed with water and dried. After removal of the solvent, the residue was purified by column chromatography on silica gel to give crystals. Recrystallization from ethyl acetate - methanol afforded colorless prisms (0.72 g, 24%), m.p. 144°–145° C.

| Elemental Analysis for $C_{28}H_{28}N_6O_2 \cdot 0.1H_2O$: | | | |
|---|---|---|---|
| | C(%) | H(%) | N(%) |
| Calcd: | 69.72; | 5.89; | 17.42 |
| Found: | 69.58; | 5.89; | 17.28 |

¹H-NMR(200MHz,CDCl³) δ: 0.82(3H,t), 1.17–1.37(2H,m), 1.45–1.60(2H,m), 2.26(3H,s), 2.34(2H,t), 3.56(3H,s), 5.23(2H,s), 6.43(2H,d), 6.60(1H,s), 6.76(2H,d), 7.28–7.32(2H,m), 7.59–7.69(2H,m), 7.96–8.00(1H,m).

IR(KBr)cm⁻¹: 1715, 1515, 1455, 1440, 1410, 1315, 1255, 1225, 1050, 785, 765.

WORKING EXAMPLE 10

2-Butyl-5-methyl-1-2'-(1H-tetrazol-5-yl)biphenyl-4-yl]methyl1benzimidazole-7-carboxylic acid A mixture of methyl 2-butyl-5-methyl-1-[[2'-(1H-tetrazol-5-yl)biphenyl-4-yl]methyl]benzimidazole-7carboxylate (0.15 g) in 1N NaOH (1.2 ml) and methanol (2 ml) was heated for 2 hours under reflux. The reaction mixture was diluted with water, washed with ether and made acidic (pH 3–4) with 1N-HCl. Crystals separated were collected by filtration and recrystallized from ethyl acetate to afford colorless crystals (0.1 g, 71%), m.p. 175°–178° C. (decomp.).

| Elemental Analysis for $C_{27}H_{26}N_6O_2 \cdot \frac{1}{2}H_2O$: | | | |
|---|---|---|---|
| | C(%) | H(%) | N(%) |
| Calcd: | 68.19; | 5.72; | 17.67 |
| Found: | 68.25; | 5.66; | 17.59 |

¹H-NMR(200MHz,DMSO-d₆) δ: 0.87(3H,t), 1.25–1.44(2H,m), 1.63–1.77(2H,m), 2.41(3H,s), 2.79(2H,t), 5.82(2H,s), 6.76(2H,d), 6.99(2H,d), 7.45–7.49(2H,m), 7.55–7.69(4H,m).

IR(KBr)cm⁻¹: 3440, 1700, 1600, 1515, 1450, 1410, 1310, 1240, 765.

WORKING EXAMPLE 11

Ethyl 2-butyl-6-methyl-1-[[2'-(1H-tetrazol-5-yl)biphenyl-4-yl]methyl]benzimidazole-7-carboxylate A mixture of ethyl 6-methyl-3-nitro-[N-[2'-(N-triphenylmethyltetrazol-5-yl)bipheny-4-yl]methyl-N-valeroyl] anthranylate (2.1 g) and iron powder (0.73 g) in conc. HCl (2.1 ml) and ethanol (10 ml) was heated for 18 hours under reflux. Insoluble materials in the reaction mixture were filtered off. The filtrate was then concentrated to dryness. The residue was dissolved in 1N-NaOH, and the resulting precipitates were filtered off through celite. The filtrate was made acidic with conc. HCl. The oily product was separated and extracted with methylene chloride. The extract was washed with water and concentrated to dryness. The syrupy product thus obtained was purified by column chromatography on silica gel to give a crystalline product. Recrystallization from ethyl acetate - isopropyl ether afforded pale brown prisms (0.8 g, 59%), m.p. 164°–165° C.

¹H-NMR(200MHz,CDCl₃) δ: 0.84, 1.06(each 3H,t), 1.20–1.39(2H,m), 1.48–1.63(2H,m), 2.32(3H,s), 2.38(2H,t), 3.88(2H,q), 5.28(2H,s), 6.56(2H,d), 6.74(1H,d), 6.86(3H,dd), 7.28–7.33(1H,m), 7.58–7.63(2H,m), 7.91–7.97(1H,m).

WORKING EXAMPLE 12

Methyl 2-butyl-5-chloro-1-[[2'-(1H-tetrazol-5-yl)biphenyl-4-yl]methyl]benzimidazole-7-carboxylate To a mixture of methyl 5-chloro-3-nitro-2-[N-[2'-(N-triphenylmethyl-1H-tetrazol-5-yl)biphenyl-4yl]methyl]-N-valerylanthranylate (1.26 g), conc. HCl (1.6 ml) and iron powder (95% purity, 0.45 g) in methanol (15 ml) was heated for 20 hours under reflux. Insoluble materials were filtered off, and the filtrate was concentrated. The concentrate was extracted with ethyl acetate and water. To the organic layer was added an aqueous solution of sodium bicarbonate and insoluble materials formed were filtered off. The filtrate was washed with water, dried and concentrated. The concentrate was purified by column chromatography on silica gel to give crystals, which were recrystallized from ethyl acetate - benzene to afford colorless crystals (0.59 g, 74%), m.p. 132°–133° C.

| Elemental Analysis for $C_{27}H_{25}N_6O_2Cl$: | | | |
|---|---|---|---|
| | C(%) | H(%) | N(%) |
| Calcd: | 64.73; | 5.03; | 16.77 |
| Found: | 64.49; | 5.06; | 16.50 |

¹H-NMR(200MHz,CDCl³) δ: 0.84(3H,t), 1.23–1.41(2H,m), 1.52–1.68(2H,m), 2.50(2H,t), 3.62(3H,s), 5.48(2H,s), 6.46(2H,d), 6.83(2H,d), 6.93(1H,m), 7.31–7.36(1H,m), 7.49(1H,d), 7.63–7.68(2H,m), 7.96–8.00(1H,m).

IR(KBr)cm⁻¹: 2960, 2875, 1720, 1510, 1460, 1430, 1400, 1280, 1230, 1190, 750.

WORKING EXAMPLE 13

2-Butyl-5-chloro-1-[[2'-(1H-tetrazol-5-yl)biphenyl-4-yl)methyl]benzimidazole-7-carboxylic acid A solution of methyl 2-butyl-5-chloro-1-[[2'-(1H-tetrazol-5-yl)biphenyl-4-yl]methyl]benzimidazol-7carboxylate (0.28 g) in 1N NaOH (2 ml) and methanol (4 ml) was stirred for 16 hours at room temperature. The reaction mixture was concentrated, and the concentrate was dissolved in water (10 ml), which was made acidic with 1N-HCl. Crystals thus separated were collected by filtration, recrystallized from methanol-chloroform to afford colorless crystals (0.2 g, 72%), m.p. 232°–234° C.

| Elemental Analysis for $C_{26}H_{23}N_6O_2 \cdot \frac{1}{2}H_2O$: | | | |
|---|---|---|---|
| | C(%) | H(%) | N(%) |
| Calcd: | 62.96; | 4.88; | 16.94 |
| Found: | 63.01; | 4.81; | 16.87 |

$^1$H-NMR(200 MHz,DMSO-d$_6$) δ: 0.87(3H,t), 1.26–1.45(2H,m), 1.64–1.79(2H,m), 2.82(2H,t), 5.81(2H,s), 6.78(2H,d), 7.00(2H,d), 7.45–7.69(5H,m), 7.91(1H,d).

IR(KBr)cm$^{-1}$: 2975, 2930, 2875, 1705, 1480, 1460, 1400, 1270, 1240, 1220, 1190, 870, 760, 740.

WORKING EXAMPLE 14

Ethyl 2-butyl-1-[2'-(1H-tetrazol-5-yl)biphenyl-4-yl]methyl]-benzimidazole-7-carboxylate A mixture of ethyl 2-butyl-1-[(2,-cyanobiphenyl-4-yl)methyl]benzimidazole-7-carboxylate (0.21 g), sodium azide (1.3 g) and ammonium chloride (1.07 g) in DMF (8 ml) was stirred for 60 hours at 110°–120° C. To the mixture was added water and the mixture was made acidic (pH 3-4) with 1N-HCl, followed by extraction with ethyl acetate. The organic layer was washed with water, dried and concentrated to dryness. To the concentrate was added ether, and resulting crude crystals were collected by filtration, followed by recrystallization from ethanol to afford colorless crystals (0.95 mg, 41%), m.p. 138°–139° C.

$^1$H-NMR(90 MHz,CDCl$_3$) δ: 0.80(3H,t), 1.07–1.77(7H,m), 2.37(2H,t), 4.07(2H,q), 5.50(2H,s), 6.47(2H,d), 6.80(2H,d), 7.00–7.10(2H,m), 7.23–7.73(4H,m), 7.90–8.10(1H,m).

IR(Nujol)cm$^{-1}$: 1715, 1410, 1290, 1260, 1125, 1040, 750.

WORKING EXAMPLE 15

2-Butyl-1-[2'-(1H-tetrazol-5-yl)biphenyl-4-yl]methyl]-benzimidazole-7-carboxylic acid A mixture of ethyl 2-butyl-1-[[2'-(1H-tetrazol-5- yl)-biphenyl-4-yl]methyl]benzimidazole-7-carboxylate (80 mg) in 2-methoxyethanol (1.5 ml) and 2N NaOH (1.5 ml) was stirred for one hour at 110°–120° C. The reaction mixture was neutralized with 2N-HCl, and then concentrated to dryness. The concentrate was dissolved in chloroform. After removal of insoluble materials by filtration, the filtrate was concentrated to dryness. Crude crystals thus obtained were recrystallized from aqueous ethanol to give colorless crystals (60 mg, 77%).

The melting point, $^1$H-NMR and IR data are in good agreement with those observed in Working Example 1.

WORKING EXAMPLE 16

2-Butyl-7-hydroxymethyl-1-[[2'-(1H-tetrazol-5-yl)biphenyl-4-yl]methyl]benzimidazole A mixture of 2-butyl-1-[(2'-cyanobiphenyl-4-yl)methyl]-7-hydroxymethylbenzimidazole (0.4 g), sodium azide (0.98 g) and ammonium chloride (0.8 g) in DMF (4 ml) was stirred for 4 days at 110°–120° C. To the reaction mixture was added water, which was extracted with ethyl acetate. The extract was washed with water and dried. After removal of the solvent, the residue was crystallized from ethyl acetate-methanol to give colorless needles, m.p. 152°–153° C.

| Elemental Analysis for $C_{26}H_{26}N_6O \cdot \frac{1}{4}C_4H_8O_2 \cdot 1/10H_2O$: | | | |
|---|---|---|---|
| | C(%) | H(%) | N(%) |
| Calcd: | 69.43; | 6.28; | 17.35 |
| Found: | 69.14; | 6.22; | 17.59 |

WORKING EXAMPLE 17

Ethyl [[2-butyl-1-[2'-(1H-tetrazol-5-yl)biphenyl-4-yl]methyl]-benzimidazol-7-yl]acetate A mixture of ethyl 2-butyl-1-[(2'-cyanobiphenyl-4yl)-methyl]benzimidazole-7-carboxylate (0.86 g), sodium azide (0.5 g) and ammonium chloride (1.6 g) in DMF (10 ml) was stirred in DMF for 4.5 days at 110°–120° C. To the reaction mixture was added water, which was made acidic (pH 3-4) with 1N-HCl, followed by extraction with ethyl acetate. The organic layer was washed with water and dried, then the solvent was distilled off. The residue was purified by column chromatography on silica gel to give crude crystals. Recrystallization from ethyl acetate afforded colorless needles (0.53 g, 56%), m.p. 129°–130° C.

| Elemental Analysis for $C_{29}H_{30}N_6O_2 \cdot 0.4H_2O$: | | | |
|---|---|---|---|
| | C(%) | H(%) | N(%) |
| Calcd: | 69.41; | 6.19; | 16.75 |
| Found: | 69.50; | 5.94; | 17.03 |

$^1$H-NMR(200 MHz,CDCl$_3$) δ: 0.83(3H,t), 1.12–1.33(5H,m), 1.48–1.63(2H,m), 2.24(2H,t), 3.41(2H,s), 4.03(2H,q), 5.46(2H,s), 6.55–6.66(3H,m), 6.87(2H,d), 6.93–6.99(2H,m), 7.28–7.32(1H,m), 7.55–7.68(2H,m), 7 95–7.99(1H,m).

IR(KBr)cm$^{-1}$: 1740, 1720, 1510, 1410, 1280, 1255, 1145, 755, 740.

WORKING EXAMPLE 18

2-Butyl-1-[[2'-(1H-tetrazol-5-yl)biphenyl-4-yl]methyl]-benzimidazole-7-acetic acid A mixture of ethyl 2-butyl-1-[[2'-(1H-tetrazol-5-yl)biphenyl-4-yl)methyl]benzimidazole-7-acetate (0.28 g) in 1N NaOH (1.5 ml) and methanol (5 ml) was heated for two hours under reflux. The reaction mixture was concentrated, which was neutralized with 1N-HCl. Crystals separated out were collected by filtration and purified by column chromatography on silica gel to afford colorless crystals (0.12 g, 46%), m.p. 170°–171° C.

| Elemental Analysis for $C_{27}H_{26}N_6O_2$: | | | |
|---|---|---|---|
| | C(%) | H(%) | N(%) |
| Calcd: | 69.51; | 5.62; | 18.01 |
| Found: | 69.60; | 5.78; | 17.90 |

$^1$H-NMR(200 MHz,DMSO-d$_6$) δ: 0.87(3H,t), 1.27-1.44(2H,m), 1.64-1.75(2H,m), 2.79(2H,t), 3.58(2H,s), 5.62(2H,s), 6.80(2H,d), 6.98-7.16(4H,m), 7.49-7.71(5H,m).

IR(KBr)cm$^{-1}$: 3430, 1720, 750.

WORKING EXAMPLE 19

2-Butyl-7-methoxymethyl-1-[[2'-(1H-tetrazol-5-yl)biphenyl-4-yl]methyl]benzimidazole sodium salt A mixture of 2-butyl-1-[(2'-cyanobiphenyl-4-yl)methyl]-7-methoxymethylbenzimidazole (0.6 g) and trimethyltin azide (1.2 g) in toluene (12 ml) was heated for 3 days under reflux in toluene (12 ml). The solvent was distilled off. To the residue was added 1N-HCl (8 ml) and the mixture was stirred for a while, followed by extraction with ethyl acetate. The organic layer was washed with water and dried, then the solvent was distilled off. The residue was purified by column chromatography on silica gel to give an oil. The product was dissolved in ethyl acetate, to which was added a methanol solution of sodium salt of 2-ethyl hexanoic acid (0.25 g). The mixture was concentrated. Crystals separated out were recrystallized from toluene-ethyl acetate to afford colorless crystals (0.22 g, 31%), m.p.175°-178° C.

| Elemental Analysis for $C_{27}H_{27}N_6ONa \cdot H_2O$: | | | |
|---|---|---|---|
| | C(%) | H(%) | N(%) |
| Calcd: | 65.84; | 5.93; | 17.06 |
| Found: | 65.94; | 5.81; | 17.06 |

$^1$H-NMR(200 MHz,CDCl$_3$) δ: 0.70(3H,t), 1.06-1.25(2H,m), 1.50-1.65(2H,m), 2.49(2H,t), 2.86(3H,s), 4.21(2H,s), 5.27(2H,s), 6.41(2H,d), 6.73-6.77(3H,m), 6.92-7.00(2H,m), 7.19-7.30(2H,m), 7.37(1H,d), 7.62(1H,d).

IR(KBr)cm$^{-1}$: 1510, 1455, 1420, 1405, 1350, 1280, 1080, 740.

WORKING EXAMPLE 20

2-Butyl-7-methoxy-1-[[2'-(1H-tetrazol-5-yl)biphenyl-4-yl]methyl]benzimidazole hydrochloride A mixture of 2-butyl-1-[(2'-cyanobiphenyl-4-yl)methyl]-7-methoxybenzimidazole (0.8 g) and trimethyltin azide (1.6 g) in toluene (15 ml) was heated for 44 hours under reflux. Crystals then separated out were collected by filtration and were dissolved in methanol (20 ml). To the solution was added 1N-HCl (8 ml), and the mixture was stirred for 5 minutes at room temperature. To the reaction mixture was added water, followed by extraction with ethyl acetate. The organic layer was washed with water and dried. The solvent was distilled off, and the residue was purified by column chromatography on silica gel to give crude crystals. Recrystallization from ethyl acetate-methanol afforded colorless prisms (0.83 g, 87%), m.p. 189°-190° C.

| Elemental Analysis for $C_{26}H_{26}N_6O \cdot HCl$: | | | |
|---|---|---|---|
| | C(%) | H(%) | N(%) |
| Calcd: | 65.75; | 5.73; | 17.69 |
| Found: | 65.46; | 5.85; | 17.44 |

$^1$H-NMR(200 MHz,DMSO-d$_6$) δ: 0.87(3H,t), 1.26-1.44(2H,m), 1.61-1.76(2H,m), 3.14(2H,t), 3.83(3H,s), 5.82(2H,s), 7.07-7.18(5H,m), 7.38(1H,d), 7.45-7.73(5H,m).

IR(KBr)cm$^{-1}$: 1615, 1550, 1490, 1455, 1440, 1355, 1275, 1260, 1130, 1100, 1060, 990, 870, 850, 775, 750, 730.

WORKING EXAMPLE 21

2-Butyl-6-methyl-1-[[2'-(1H-tetrazol-5-yl)biphenyl-4-yl]benzimidazole-7-carboxylic acid A mixture of ethyl 2-butyl-6-methyl-1-[[2'-(1H-tetrazol-5-yl)biphenyl-4-yl]methyl]benzimidazole-7-carboxylate (0.55 g) in 5N aqueous sodium hydroxide (5 ml) and ethanol (10 ml) was heated for 100 hours under reflux. The reaction mixture was concentrated to dryness and then was dissolved in water, and the solution was made acidic with conc. HCl. Precipitates separated out were collected by filtration and washed with a mixture of dichloromethane and methanol. The precipitates were dissolved in saturated aqueous sodium bicarbonate. After removal of insoluble materials by filtration, the filtrate was made acidic with conc. HCl. Precipitates then separated out were collected by filtration and crystallized from dimethylformamide -H$_2$O to afford colorless crystals (0.22 g, 42%), m.p. 298°-299° C. H-NMR(200 MHz,CDCl$_6$) δ: 0.85(3H,t), 1.23-1.43(2H,m), 1.58-1.75(2H,m), 2.38(3H,s), 2.70(2H,t), 5.47(2H,s), 6.87, 7.02 (each 2H,d), 7.07(1H,d), 7.45-7.71(5H,m).

| Elemental Analysis for $C_{27}H_{26}N_6O_2 \cdot 1/10H_2O$: | | | |
|---|---|---|---|
| | C(%) | H(%) | N(%) |
| Calcd: | 69.24; | 5.64; | 17.94 |
| Found: | 68.97; | 5.85; | 17.81 |

WORKING EXAMPLE 22

2-Butyl-1-[[2'-(1H-tetrazol-5-yl)biphenyl-4-yl]methyl]-7-methylbenzimidazole

A mixture of 2-butyl-1-[(2'-cyanobiphenyl-4-yl)methyl]-7-methylbenzimidazole (0,5 g), sodium azide (1.3 g) and ammonium chloride (1.1 g) in DMF (5 ml) was stirred for 3.5 days at 110°-120° C. To the reaction mixture was added water, which was made acidic (pH 3-4) with 1N-HCl, followed by extraction with ethyl acetate. The organic layer was washed with water and dried. The solvent was distilled off, and the residue was purified by column chromatography on silica gel to give crystals. Recrystallization from ethyl acetate-methanol afforded colorless crystals (0.36 g, 62%), m.p. 222°-224° C.

| Elemental Analysis for $C_{26}H_{26}N_6 \cdot \tfrac{1}{4}C_4H_8O_2$: | | | |
|---|---|---|---|
| | C(%) | H(%) | N(%) |
| Calcd: | 72.95; | 6.35; | 18.90 |
| Found: | 72.80; | 6.35; | 19.02 |

¹H-NMR(200 MHz,CDCl₃) δ: 0.80(3H,t), 1.14–1.32(2H,m), 1.44–1.59(2H,m), 2.14(2H,t), 2.26(3H,s], 5.32(2H,s), 6.48–6.56(3H,m), 6.83–6.89(4H,m), 7.29–7.34(1H,m), 7.55–7.68(2H,m), 7.92–7.97(1H,m).

IR(KBr)cm⁻¹: 1510, 1450, 1410, 780, 750, 740.

WORKING EXAMPLE 23

Ethyl 2-isopropyl-1-[[2'-(1H-tetrazol-5-yl)biphenyl-4-yl]methyl]benzimidazole-7-carboxylate A mixture of ethyl 1-[(2'-cyanobiphenyl-4-yl)methyl]-2-isopropylbenzimidazole-7-carboxylate (2.12 g), sodium azide (3.9 g) and ammonium chloride (3.2 g) in DMF (15 ml) was stirred for 5 days at 110°–120 C. To the reaction mixture was added water (150 ml), which was made acidic (pH 3–4) with dilute hydrochloric acid, followed by extraction with ethyl acetate. The organic layer was washed with water, dried and concentrated to dryness. The concentrate was crystallized from ethanol to afford colorless prisms (1.2 g, 52%), m.p. 144°–146° C.

| Elemental Analysis for C₂₇H₂₆N₆O₂.¼C₂H₅OH.H₂O: | | | |
|---|---|---|---|
|  | C(%) | H(%) | N(%) |
| Calcd: | 66.58; | 5.99; | 16.94 |
| Found: | 66.38; | 5.74; | 16.69 |

¹H-NMR(90 MHz,CDCl₃-CF₃COOH) : 1.30(3H,t), 1.53(6H,d), 3.37–3.80(1H,m), 4.30(2H,q), 5.97(2H,s), 6.90(2H,d), 7.13(2H,d), 7.43–8.10(7H,m).

IR(Nujol)cm 1730, 1450, 1285, 1270, 750.

WORKING EXAMPLE 24

Ethyl 2-methyl-1-[[2'-(1H-tetrazol-5-yl)biphenyl-4-yl]methyl]benzimidazol-7-carboxylate A mixture of ethyl 1-[(2'-cyanobiphenyl-4-yl)methyl]-2-methylbenzimidazole-7-carboxylate (2.5 g), sodium azide (3.9 g) and ammonium chloride (3.2 g) in DMF (30 ml) was stirred for 4 days at 110°–120° C. The reaction mixture was worked up according to the procedure described in Working Example 23 to give crystals. Recrystallization from ethanol afforded colorless prisms (1.36 g, 49%), m.p. 205°–206° C.

| Elemental Analysis for C₂₅H₂₂N₆O₂.2/5EtOH: | | | |
|---|---|---|---|
|  | C(%) | H(%) | N(%) |
| Calcd: | 67.82; | 5.38; | 18.39 |
| Found: | 67.64; | 5.38; | 18.24 |

¹H-NMR(90 MHz,CDCl₃-CF₃COOH) δ: 1.27(4H,t). 2.90(3H,s), 3.87(1H,q), 4.30(2H,q), 5.93(2H,s), 6.93(2H,d), 7.10(2H,d), 7.40–7.80(5H,m), 8.00(2H,d).

IR(Nujol)cm 1725, 1410, 1290, 1260, 1220, 1115, 1040, 750.

WORKING EXAMPLE 25

Ethyl 2-ethyl-1-[[2'-(1H-tetrazol-5-yl)biphenyl-4-yl]methyl]-benzimidazole-7-carboxylate A mixture of ethyl 1-[(2'-cyanobiphenyl-4yl)methyl]-2-ethylbenzimidazole-7-carboxylate (1.55 g), sodium azide (2.6 g) and ammonium chloride (2.14 g) in DMF (15 ml) was stirred for 5 days at 110°–120 C. The reaction mixture was worked up according to the procedure described in Working Example 23 to give crystals. Recrystallization from ethanol afforded colorless prisms (0.68 g, 40%), m.p. 188°–189° C.

| Elemental Analysis for C₂₆H₂₄N₆O₂.2/5H₂O: | | | |
|---|---|---|---|
|  | C (%) | H (%) | N (%) |
| Calcd: | 67.93; | 5.44; | 18.28 |
| Found: | 67.76; | 5.36; | 18.54 |

¹H-NMR(90 MHz,CDCl₃-CF₃COOH) δ: 1.33(3H,t), 1.50(3H,t), 3.27(2H,q), 4.33(2H,q), 5.97(2H,s), 6.93(2H,d), 7.17(2H,d), 7.40–8.07(7H,m).

IR(Nujol)cm⁻¹: 1710, 1285, 1265, 755.

WORKING EXAMPLE 26

2-Methyl-1-2'-(1H-tetrazol-5-yl)biphenyl-4yl]methyl]-benzimidazole-7-carboxylic acid Ethyl 2-methyl-1-[[2'-(1H-tetrazol-5-yl)biphenyl4-yl]methyl]benzimidazole-7-carboxylate (0.64 g) was heated under reflux for 4 hours in a mixture of methanol (10 ml) and 2N NaOH. The reaction mixture was concentrated to dryness, and the concentrate was dissolved in water, followed by neutralization with 1N-HCl to afford crystals. Recrystallization from DMF-EtOH-H₂O gave colorless prisms (0.3 g, 49%), m.p. 283°–284° C. (decomp.).

| Elemental Analysis for C₂₃H₁₈N₆O₂.1/5H₂O: | | | |
|---|---|---|---|
|  | C (%) | H (%) | N (%) |
| Calcd: | 66.72; | 4.48; | 20.30 |
| Found: | 66.96; | 4.40; | 20.25 |

¹H-NMR(90 MHz,CDCl₃-CF₃COOH) δ: 2.97(3H,s), 5.97(2H,s), 6.97(2H,d), 7.17(2H,d), 7.50–7.90(5H,m), 8.10(1H,d), 8.20(1H,d).

IR(Nujol)cm⁻¹: 2470, 1700, 1455, 1410, 1240, 1220, 990, 750.

WORKING EXAMPLE 27

2-Ethyl-1-[[2'-(1H-tetrazol-5-yl)biphenyl-4-yl]methyl]-benzimidazole-7-carboxylic acid A mixture of ethyl 2-ethyl-1-[[2'-(1H-tetrazol-5-yl)biphenyl-4-yl]methyl]benzimidazole-7-carboxylate (0.5 g) in methanol (10 ml) and 2N NaOH was heated under reflux for 4 hours. The reaction mixture was concentrated to dryness. The concentrate was dissolved in water, followed by neutralization with 1N-HCl to give crystals. Recrystallization from DMF-ethanol-water afforded colorless prisms (0.27 g, 58%), m.p. 261°–262° C.

| Elemental Analysis for C₂₄H₂₀N₆O₂: | | | |
|---|---|---|---|
|  | C (%) | H (%) | N (%) |
| Calcd: | 67.63; | 4.70; | 19.45 |
| Found: | 67.91; | 4.75; | 19.80 |

¹H-NMR(90 MHz,CDCl₃-CF₃COOH) δ: 1.50(3H,t), 3.20(2H,q), 5.97(2H,s), 6.93(2H,d), 7.13(2H,d), 7.37–8.17(7H,m).

IR(Nujol)cm⁻¹: 3070, 2720, 1700, 1450, 1410, 1290, 1250, 1210, 755.

WORKING EXAMPLE 28

2-Isopropyl-1-[[2'-(1H-tetrazol-5-yl)biphenyl-4-yl]methyl]benzimidazole-7-carboxylic acid A mixture of ethyl 2-isopropyl-1-[[2'-(1H-tetrazol-5-yl)biphenyl-4-yl]methyl]benzimidazole-7-carboxylate (1.2 g) in methanol (5 ml) and 2N NaOH (5 ml) was heated for 4 hours under reflux. The reaction mixture was concentrated to dryness and then dissolved in water, followed by neutralization with 1N-HCl to give crystals. Recrystallization from DMF–50% EtOH afforded colorless prisms (0.8 g, 71%), m.p. 265°–267° C. (decomp.).

| Elemental Analysis for $C_{25}H_{22}N_6O_2 \cdot 3/10H_2O$: | | | |
|---|---|---|---|
| | C (%) | H (%) | N (%) |
| Calcd: | 67.65; | 5.13; | 18.93 |
| Found: | 67.64; | 5.07; | 19.00 |

$^1$H-NMR(90 MHz,CDCl$_3$-CF$_3$COOH) δ: 1.67(6H,d), 3.40–3.83(1H,m), 6.00(2H,s), 6.90(2H,d), 7.13(2H,d), 7.43–7.83(5H,m), 8.07(2H,d).

IR(Nujol)cm$^{-1}$: 2620, 1695, 1285, 1260, 1245, 1205, 760.

WORKING EXAMPLE 29

2-Butyl-1-[[2'-(1H-tetrazol-5-yl)biphenyl-4yl]methyl]-benzimidazole-7-carboxylic acid 2.potassium salt To a solution of 2-butyl-1-[[2'-(1H-tetrazol-5-yl)biphenyl-4-yl]methyl]benzimidazole-7-carboxylic acid (1.2 g) and potassium 2-ethyl hexanoate (1.3 g) in ethanol (50 ml) was added toluene (50 ml) and the ethanol was removed by evaporation. Crystals then separated out give colorless crystals (1.1 g, 79%), m.p. 355°–358° C. (decomp.)

| Elemental Analysis for $C_{26}H_{22}K_2N_6O_2 \cdot H_2O$: | | | |
|---|---|---|---|
| | C (%) | H (%) | N (%) |
| Calcd: | 57.12; | 4.42; | 15.37 |
| Found: | 56.93; | 4.26; | 15.01 |

$^1$H-NMR(200 MHz, DMSO-d$_6$) δ: 0.86(3H,t), 1.22–1.43(2H,m), 1.60–1.76(2H,m), 2.70(2H,t), 6.06(2H,s), 6.79(2H,d), 6.94–7.03(3H,m), 7.20–7.34(4H,m), 7.40(1H,dd), 7.53–7.58(1H,m).

IR(KBr)cm$^{-1}$: 3350, 1600, 1570, 1515, 1460, 1400, 1360, 1315, 1280, 1005, 825, 785, 760.

WORKING EXAMPLE 30

2-Butyl-7-hydroxy-1-[2'-(1H-tetrazol-5-yl)biphenyl-4-yl]methyl]benzimidazole A mixture of 2-butyl-1-[(2'-cyanobiphenyl-4yl)methyl]-7-hydroxybenzimidazole (0.69 g) and trimethyltin azide (1.1 g) in toluene (15 ml) was heated for 4 days under reflux. Crystals then separated out were collected by filtration and then stirred in a mixture of 1N-HCl (10 ml) and methanol (15 ml) for 10 minutes at room temperature. To the resultant solution was added 1N NaOH to adjust to pH 3–4 to give crystals. The crude crystals were purified by column chromatography on silica gel to give crystals. Recrystallization from acetone afforded colorless crystals, m.p. 186°–188° C.

| Elemental Analysis for $C_{25}H_{24}N_6O \cdot 1/2H_2O$: | | | |
|---|---|---|---|
| | C (%) | H (%) | N (%) |
| Calcd: | 69.27; | 5.81; | 19.39 |
| Found: | 69.60; | 5.69; | 19.26 |

$^1$H-NMR(200 MHz,DMSO-d$_6$) δ: 0.84(3H,t), 1.23–1.41(2H,m), 1.55–1.70(2H,m), 2.71(2H,t), 5.68(2H,s), 6.60(1H,d), 6.95(1H,t), 7.02–7.06(5H,m), 7.48–7.70(4H,m), 10.00(1H,s).

IR(KBr)cm$^{-1}$: 1620, 1490, 1460, 1350, 1295, 780, 755, 730.

WORKING EXAMPLE 31

Methyl 2-propyl-1-[[2'-(1H-tetrazol-5-yl)biphenyl-4-yl)methyl]-benzimidazole-7-carboxylate A mixture of 2-propyl-1-[[2'-(1H-tetrazol-5-yl)biphenyl-4-yl]methyl]benzimidazole-7-carboxylic acid (465 mg) and conc. sulfuric acid (7.2 g) in methanol (60 ml) was heated for 24 hours under reflux. After removal of solvent, the residue was suspended with water, to which was added 1N-NaOH to adjust to pH 3–4, followed by extraction with ethyl acetate. The organic layer was washed with water and dried, followed by evaporation of the solvent. The residue was purified by column chromatography on silica gel. Recrystallization from ethanol afforded colorless prisms (310 mg), m.p. 195°–196° C.

| Elemental Analysis for $C_{26}H_{24}N_6O_2 \cdot 2/5H_2O$: | | | |
|---|---|---|---|
| | C (%) | H (%) | N (%) |
| Calcd: | 67.93; | 5.44; | 18.28 |
| Found: | 68.02; | 5.33 | 18.33 |

$^1$H-NMR(90 MHz,CDCl$_3$) δ: 0.87(3H,t), 1.37–1.80(2H,m), 2.30(2H,t), 3.60(3H,s), 5.47(2H,s), 6.47(2H,d), 6.80(2H,d), 6.93–8.00(7H,m).

IR(Nujol)cm : 1730, 1440, 1290, 1280, 1270, 760.

The following compounds (Working Examples 32–33) were prepared according to the procedure described in Working Example 5.

WORKING EXAMPLE 32

Methyl 2-ethyl-1-[[2'-(1H-tetrazol-5-yl)biphenyl-4-yl]methyl]-benzimidazole-7-carboxylate m.p.: 185°–186° C.

| Elemental Analysis for $C_{25}H_{22}N_6O_2 \cdot 1/2C_4H_8O_2 \cdot H_2O$: | | | |
|---|---|---|---|
| | C (%) | H (%) | N (%) |
| Calcd: | 66.70; | 5.47; | 17.29 |
| Found: | 66.70; | 4.26; | 17.49 |

WORKING EXAMPLE 33

Methyl 2-isopropyl-1-[[2'-(1H-tetrazol-5-yl)biphenyl-4-yl]methyl]benzimidazole-7-carboxylate

WORKING EXAMPLE 34

Methyl 2-butyl-1-[[2'-(1H-tetrazol-5-yl)biphenyl-4-yl]methyl]-benzimidazole-7-carboxylate A mixture of 2-butyl-1-[[2'-(1H-tetrazol-5-yl)biphenyl-4-yl]methyl]benzimidazole-7-carboxylic acid (1.8 g) in methanol (18 ml) and conc. sulfuric acid (14.4 g) was heated for 24 hours under reflux. After removal of the solvent by evaporation, the residue was suspended with water, whose pH was adjusted to 3-4 with 1N-NaOH, followed by extraction with ethyl acetate. The organic layer was washed with water and dried. The solvent was removed by evaporation and the residue was purified by column chromatography on silica gel. Recrystallization from ethanol afforded colorless prisms (1.05 g), m.p. 153°-155° C.

| Elemental Analysis for $C_{27}H_{26}N_6O_2 \cdot 2/5H_2O$: | | | |
|---|---|---|---|
| | C (%) | H (%) | N (%) |
| Calcd: | 68.45; | 5.70; | 17.74 |
| Found: | 68.63; | 5.61; | 17.72 |

$^1$H-NMR(90 MHz,CDCl$_3$) δ: 0.80(3H,t), 1.00-1.73(4H,m), 2.37(2H,t), 3.60(3H,s), 5.47(2H,s), 6.47(2H,d), 6.80(2H,d), 6.97-8.00(7H,m).

IR(Nujol)cm$^{-1}$: 1720, 1450, 1430, 1290, 1280, 1270, 755.

WORKING EXAMPLE 35

Ethyl 2-sec-butyl-1-[[2'-(1H-tetrazol-5-yl)biphenyl-4-yl]methyl]benzimidazole-7-carboxylate This compound was prepared according to the procedure described in Working Example 14.

Melting point : 128°-130° C.

| Elemental Analysis for $C_{28}H_{28}N_6O_2 \cdot 2/5C_4H_8O_2 \cdot 2/5H_2O$: | | | |
|---|---|---|---|
| | C (%) | H (%) | N (%) |
| Calcd: | 67.98; | 6.06; | 16.07 |
| Found: | 68.10; | 6.07; | 15.94 |

WORKING EXAMPLE 36

Pivaloyloxymethyl 2-butyl-1-[[2'-(1H-tetrazol-5-yl)biphenyl-4-yl]methyl]-benzimidazole-7-carboxylate A solution of 2-butyl-1-[[2'-(1H-tetrazol-5-yl)biphenyl-4-yl]methyl]benzimidazole-7-carboxylic acid (3.0 g), triphenylmethyl chloride (1.96 g) and triethylamine (1.0 ml) in methylene chloride (20 ml) was stirred for 16 hours at room temperature. The reaction mixture was washed with water and dried. After removal of the solvent, the residue was purified by column chromatography on silica gel to give colorless powder (4.25 g). The N-trityl compound thus obtained was dissolved in DMF (5 ml). To the solution were added potassium carbonate (0.2 g) and pivaloyloxymethyl iodide (0.35 g), and the mixture was stirred for 2 hours at room temperature. The reaction mixture was concentrated. To the concentrate were added water and ethyl acetate, which was subjected to extraction. The organic layer was washed with water and dried. After removal of the solvent by evaporation, the residue was dissolved in methanol (10 ml). To the solution was added 1N-HCl (3 ml), and the mixture was stirred for 1.5 hour at room temperature. The reaction mixture was concentrated to dryness, and the concentrate was purified by column chromatography on silica gel to give colorless powdery crystals (0.43 g, 74%), m.p. 102°-105° C.

| Elemental Analysis for $C_{32}H_{34}N_6O_4 \cdot 1/2H_2O$: | | | |
|---|---|---|---|
| | C (%) | H (%) | N (%) |
| Calcd: | 66.77; | 6.13; | 14.60 |
| Found: | 66.76; | 6.09; | 14.45 |

$^1$H-NMR(200 MHz,CDCl$_3$) δ: 0.87(3H,t), 1.16(9H,s), 1.23-1.42(2H,m), 1.57-1.72(2H,m), 2.53(2H,t), 5.60(2H,s), 5.70(2H,s), 6.60(2H,d), 6.89(2H,d), 7.11(1H,t), 7.25-7.27(1H,m), 7.33-7.38(1H,m), 7.58-7.63(3H,m), 7.97-8.02(1H,m).

IR(KBr)cm$^{-1}$: 2975, 1750, 1730, 1480, 1450, 1410, 1280, 1260, 1150, 1100, 1010, 950, 760, 750.

In accordance with the method of Working Example 36, the following compounds were synthesized.

WORKING EXAMPLE 37

1-(Cyclohexyloxycarbonyloxy)ethyl 2-butyl-1-[[2'-(1H-tetrazol-5-yl)biphenyl-4-yl]methyl]benzimidazole-7-carboxylate Yield : 74%.

Melting point : 102°-105° C.

| Elemental Analysis for $C_{35}H_{38}N_6O_5 \cdot 1/5CHCl_3$: | | | |
|---|---|---|---|
| | C (%) | H (%) | N (%) |
| Calcd: | 65.39; | 5.95; | 13.00 |
| Found: | 65.18; | 5.99; | 12.86 |

$^1$H-NMR(200 MHz,CDCl$_3$) : 0.87(3H,t), 1.17-1.87(18H,m), 2.53(2H,t), 4.45-4.58(1H,m), 5.52-5.75(2H,m), 6.60(2H,d), 6.73(1H,q), 6.89(2H,d), 7.12(1H,t), 7.27-7.35(2H,m), 7.57-7.66(3H,m), 7.98-8.03(1H,m).

IR(KBr)cm$^{-1}$: 2950, 2875, 1760, 1740, 1450, 1420, 1280, 1250, 1080, 1000, 910, 760.

WORKING EXAMPLE 38

1-(Ethoxycarbonyloxy)ethyl 2-butyl-1-[[2'-(1H-tetrazol-5-yl)biphenyl-4-yl]methyl]-benzimidazole-7-carboxylate Yield : 75%.

Melting point : 92°-95° C.

| Elemental Analysis: | | | |
|---|---|---|---|
| | C (%) | H (%) | N (%) |
| Calcd: | 64.46; | 5.76; | 14.55 |
| Found: | 64.56; | 5.69; | 14.52 |

$^1$H-NMR(200 MHz,CDCl$_3$) δ: 0.86(3H,t), 1.21(3H,t), 1.27-1.43(2H,m), 1.42(3H,d), 1.46-1.69(2H,m), 2.50(2H,t), 4.13(2H,dq), 5.48-5.73(2H,m), 6.56(2H,d), 6.72(1H,q), 6.86(2H,d), 7.09(1H,t), 7.19-7.23(1H,m), 7.29-7.34(1H,m), 7.55-7.64(3H,m), 7.97-8.01(1H,m).

IR(KBr)cm$^{-1}$: 1760, 1730, 1410, 1375, 1275, 1245, 1070, 990, 760.

WORKING EXAMPLE 39

(5-Methyl-2-oxo-1,3-dioxolen-4-yl)methyl 2-butyl-1-[[2'-(1H-tetrazol-5-yl)biphenyl-4-yl]methyl]-benzimidazole-7-carboxylate Yield : 71%.
Melting point : 123°–125° C.

| Elemental Analysis for $C_{31}H_{28}N_6O_5.1/2H_2O$: | | | |
|---|---|---|---|
| | C (%) | H (%) | N (%) |
| Calcd: | 64.91; | 5.10; | 14.65 |
| Found: | 64.79; | 4.82; | 14.34 |

$^1$H-NMR(200 MHz,CDCl$_3$) δ: 0.84(3H,t), 1.22–1.40(2H,m), 1.53–1.68(2H,m), 2.16(3H,s), 2.46(2H,t), 4.81(2H,s), 5.54(2H,s), 6.53(2H,d), 6.86(2H,d), 7.08–7.22(2H,m), 7.43–7.38(1H,m), 7.58–7.65(3H,m), 7.95–8.00(1H,m).

IR(KBr)cm$^{-1}$: 1820, 1720, 1400, 1300, 1275, 1250, 1220, 1185, 1105, 1000, 745.

WORKING EXAMPLE 40

2-Hydroxyethyl 2-butyl-1-[[2'-(1H-tetrazol-5-yl)biphenyl-4-yl]methyl]-benzimidazole-7-carboxylate To a solution of ethyl 2-butyl-1-[[2'-(1H-tetrazol-5-yl)biphenyl-4-yl]methyl]benzimidazole-7-carboxylate (0.72 g) in ethylene glycol (15 ml) was added, while stirring at room temperature, sodium hydride (60% oil, 0.25 g) and the mixture was stirred at room temperature for 15 hours. To the reaction mixture was added ice-water (100 ml), which was made acidic with formic acid. Precipitates then formed were dissolved in ethyl acetate (100 ml) and the solution was washed with water, dried and concentrated to dryness to give a crystalline product. The crystals were recrystallized from acetone to afford colorless crystals (0.49 g, 66%), m.p. 145°–147° C.

| Elemental Analysis for $C_{28}H_{28}N_6O_3.1/2C_3H_6O$: | | | |
|---|---|---|---|
| | C (%) | H (%) | N (%) |
| Calcd: | 67.41; | 5.94; | 15.99 |
| Found: | 67.19; | 5.84; | 15.79 |

$^1$H-NMR(200 MHz,CDCl$_3$) δ: 0.93(3H,t), 1.23–1.97(4H,m), 2.13(3H,s), 2.87(2H,t), 3.77(2H,t), 4.23(2H,t), 5.73(2H,s), 6.77(2H,d), 7.00(2H,d), 7.20(1H,t),7.43–7.93(6H,m).

IR(Nujol)cm$^{-1}$: 3340, 1715, 1410, 1290, 1265, 1035, 755.

WORKING EXAMPLE 41

2-(4-Morpholino)ethyl 2-butyl-1-[[2'-(1H-tetrazol-5-yl)biphenyl-4-yl]methyl]-benzimidazole-7-carboxylate To a cold solution of 2-butyl-1-[[2'-(N-triphenylmethyltetrazol-5-yl)biphenyl-4-yl] methylbenzimidazole-7-carboxylic acid (0.4 g), 4-(2-hydroxyethyl)morpholine (0.15 g) and diethyl phosphocyanidate (0.1 g) in DMF (2 ml) was added a solution of triethylamine (0.06 g) in DMF (1 ml) and the mixture was stirred at room temperature for 30 hours. The reaction mixture was concentrated to dryness to give a residue, which was purified by column chromatography on silica gel to afford a colorless powder (0.3 g, 65%). The product was dissolved in methanol (7 ml) and to the solution was added 1N-HCl (1.2 ml). After stirring at room temperature for 2 hours, the reaction solution was concentrated to dryness to give a residue. The residue was dissolved in CH$_2$Cl$_2$-H$_2$O and the aqueous layer was made basic with aqueous NaHCO$_3$ solution. The aqueous layer extracted with CH$_2$Cl$_2$ and the combined CH$_2$Cl$_2$ solution was washed with H$_2$O, dried and evaporated to dryness to give a residue. The residue was purified by column chromatography on silica gel to give colorless fine crystals (0.19 g, 87%), m.p. 98°–110° C.

| Elemental Analysis for $C_{32}H_{35}N_7O_3.3/5\ H_2O$: | | | |
|---|---|---|---|
| | C (%) | H (%) | N (%) |
| Calcd: | 66.67; | 6.33; | 17.01 |
| Found: | 66.41; | 6.15; | 16.89 |

$^1$H-NMR(200 MHz,CDCl$_3$) δ: 0.96(3H,t), 1.34–1.52(2H,m), 1.71–1.88(2H,m), 2.58(4H,br t), 2.85(2H,t), 2.94(2H,br t), 3.39(2H,br t), 4.10(2H,br t), 5.65(2H,s), 6.63(2H,d), 6.96(2H,d), 7.25(1H,t), 7.40–7.61(4H,m), 7.77(1H,dd), 7.83(1H,d).

The following compounds (Working Examples 42–43) were prepared by a method similar to that of Working Example 41.

WORKING EXAMPLE 42

2-(1-Piperidino)ethyl 2-butyl-1-[[2'-(1H-tetrazol-5-yl)biphenyl-4-yl]methyl]-benzimidazole-7-carboxylate colorless powder (55%), m.p. 210°–213° C.

| Elemental Analysis for $C_{33}H_{37}N_7O_2.3/5\ H_2O$: | | | |
|---|---|---|---|
| | C (%) | H (%) | N (%) |
| Calcd: | 68.99; | 6.70; | 17.07 |
| Found: | 68.93; | 6.59; | 16.94 |

$^1$H-NMR(200 MHz,CDCl$_3$) δ: 0.96(3H,t), 1.27–1.58(8H,m), 1.79–1.94(2H,m), 2.72–2.85(4H,m), 2.93(2H,t), 3.20–3.31(2H,m), 4.10–4.27(2H,m), 5.63(2H,br s), 6.59–6.70(2H,m), 7.04(2H,d), 7.26(1H,t), 7.36–7.50(4H,m), 7.72–7.77(1H,m), 7.98(1H,dd).

WORKING EXAMPLE 43

2-(Dimethylamino)ethyl 2-butyl-1-[[2'-(1H-tetrazol-5-yl)biphenyl-4-yl]methyl]-benzimidazole-7-carboxylate colorless powder (91%), m.p. 206°–208° C.

| Elemental Analysis for $C_{30}H_{33}N_7O_2.2.1\ H_2O$: | | | |
|---|---|---|---|
| | C (%) | H (%) | N (%) |
| Calcd: | 64.18; | 6.68; | 17.46 |
| Found: | 64.31; | 6.40; | 17.16 |

$^1$H-NMR(200 MHz,CDCl$_3$) δ: 0.96(3H,t), 1.39–1.57(2H,m), 1.79–1.94(2H,m), 2.34(6H,s), 2.94(2H,t), 3.10(2H,br t), 4.19(2H,br t), 5.66(2H,s), 6.63(2H,d), 7.03(2H,d), 7.27(1H,t), 7.39–7.54(4H,m), 7.73–7.78(1H,m), 7.97(1H,dd).

WORKING EXAMPLE 44

Methyl 2-methoxymethyl-1-[[2'-(1H-tetrazol-5-yl)biphenyl-4-yl]methyl]benzimidazole-7-carboxylate A mixture of methyl 1-[(2'-cyanobiphenyl-4-yl)methyl]-2-methoxymethylbenzimidazole-7-carboxylate (0.4 g) and trimethyltin azide (1.0 g) in toluene (10 ml) was refluxed for 49 hours. The reaction solution was concentrated to dryness to give a residue and the residue was dissolved in methanol (6 ml) and 1N-HCl (6 ml). The solution was allowed to stir for 3 hours and concentrated to dryness to give a residue. The residue was dissolved in $CH_2Cl_2$-$H_2O$ and the mixture was made neutral with 1N-NaOH. The organic layer was washed with $H_2O$, dried and concentrated to dryness to give a residue, which was purified by column chromatography on silica gel to give a crystalline product. Recrystallization from ethyl acetate-isopropylether gave colorless needles (0.3 g, 68%).

m.p. 191°–194° C.

| Elemental Analysis for $C_{25}H_{22}N_6O_3.3/5$ $H_2O$: | | | |
|---|---|---|---|
| | C (%) | H (%) | N (%) |
| Calcd: | 64.53; | 5.03; | 18.06 |
| Found: | 64.57; | 4.94; | 17.97 |

$^1$H-NMR(200 MHz,CDCl$_3$) δ: 3.27(3H,s), 3.66(3H,s), 4.21(2H,s), 5.62(2H,s), 6.59(2H,d), 6.87(2H,d), 7.16(1H,t), 7.30–7.36(2H,m), 7.55–7.63(3H,m), 7.93–7.99(1H,m).

The following compounds (Working Examples 45–47) were prepared by a method similar to that of Working Example 44.

WORKING EXAMPLE 45

Ethyl 2-ethoxymethyl-1-[[2'-(1H-tetrazol-5-yl)biphenyl-4-yl]methyl]benzimidazole-7-carboxylate colorless powder.

$^1$H-NMR(200 MHz,CDCl$_3$) δ: 1.14(3H,t), 1.21(3H,t), 3.45(2H,q), 4.20(2H,q), 4.85(2H,s), 5.89(2H,s), 6.95(2H,d), 7.10–7.40(3H,m), 7.56–7.70(3H,m), 7.96(1H,dd).

WORKING EXAMPLE 46

Ethyl 2-ethylthiomethyl-1-[[2'-(1H-tetrazol-5-yl)biphenyl-4-yl]methyl]benzimiaazole-7-carboxylate colorless powder (75%).

$^1$H-NMR(200 MHz,CDCl$_3$) δ: 1.12(3H,t), 1.23(3H,t), 2.46(2H,q), 4.11(2H,q), 3.36(2H,s), 5.63(2H,s), 6.58(2H,d), 6.87(2H,d), 7.10–7.36(3H,m), 7.56–7.64(3H,m), 7.97–8.04(1H,m).

WORKING EXAMPLE 47

Ethyl 2-methylthiomethyl-1-[[2'-(1H-tetrazol-5-yl)biphenyl-4-yl] methyl]benzimidazole-7-carboxylate colorless powder (56%).

$^1$H-NMR(200 MHz,CDCl$_3$) δ: 1.21(3H,t), 2.03(3H,s), 4.11(2H,q), 5.63(2H,s), 6.60(2H,d), 6.91(2H,d), 7.15–7.40(3H,m), 7.55–7.68(3H,m), 8.00–8.10(1H,m).

WORKING EXAMPLE 48

Ethyl 2-hydroxymethyl-1-[2'-(1H-tetrazol-5-yl)biphenyl-4-yl)biphenyl-4-yl]methyl]benzimidazole-7-carboxylate The compound was prepared by a method similar to that of Working Example 44 from ethyl 2-acetoxymethyl-1-[[2'-(1H-tetrazol-5-yl)biphenyl-4yl]methyl]benzimidazole-7-carboxylate.

pale yellow powder (80%).

$^1$H-NMR(200 MHz,CDCl$_3$) δ: 1.20(3H,t), 4.17(2H,q), 4.82(2H,br s), 5.56(2H,br s), 6.65(2H,d), 6.86(2H,d), 6.82–6.95(1H,m), 7.21–7.54(4H,m), 7.62(1H,d), 7.75–7.82(1H,m).

WORKING EXAMPLE 49

2-Methoxymethyl-1-[2'-(1H-tetrazol-5-yl)biphenyl-4-yl]methyl]benzimidazole-7-carboxylic acid A solution of methyl 2-methoxymethyl-1-[[2'-(1H-tetrazol-5-yl)biphenyl-4-yl]methyl]benzimidazole-7carboxylate (0.2 g) in methanol (10 ml) and 1N-NaOH (1 5 ml) was heated at 80° C for 20 hours. The solution was concentrated to dryness to give a residue. The residue was dissolved in $H_2O$ and made acidic to give a crystalline product. Recrystallization from DMF-MeOH-$H_2O$ gave colorless prisms (0.16 g, 80%).

m.p. 272°–274° C.

| Elemental Analysis for $C_{24}H_{20}N_6O_3$ (Mw. 440.46): | | | |
|---|---|---|---|
| | C (%) | H (%) | N (%) |
| Calcd: | 65.45; | 4.58; | 19.08 |
| Found: | 65.32; | 4.47; | 18.95 |

$^1$H-NMR(200 MHz,DMSO-d$_6$) δ: 3.28(3H,s), 4.68(2H,s), 5.87(2H,s), 6.80(2H,d), 6.98(2H,d), 7.29(1H,t), 7.45–7.70(5H,m), 7.91(1H,dd).

The following compounds (Working Examples 50–54) were prepared by a method like that of Working Example 49.

WORKING EXAMPLE 50

2-Ethoxymethyl-1-[[2'-(1H-tetrazol-5-yl)biphenyl-4-yl]methyl]benzimidazole-7-carboxylic acid colorless powder (80%), m.p. 243°–245° C.

| Elemental Analysis for $C_{25}H_{22}N_6O_3.\frac{1}{2}H_2O$ (Mw. 463.50): | | | |
|---|---|---|---|
| | C (%) | H (%) | N (%) |
| Calcd: | 64.78; | 5.00; | 18.13 |
| Found: | 64.99; | 4.97; | 18.26 |

$^1$H-NMR(200 MHz,DMSO-d$_6$) δ: 1.01(3H,t), 3.48(2H,q), 4.72(2H,s), 5.89(2H,s), 6.81(2H,d), 6.99(2H,d), 7.29(1H,t), 7.44–7.70(5H,m), 7.91(1H,dd).

WORKING EXAMPLE 51

2-Methylthiomethyl-1-[[2'-(1H-tetrazol-5-yl)biphenyl-4-yl]methyl]benzimidazole-7-carboxylic acid colorless powder (82%), m.p. 270°–272° C.

| Elemental Analysis for $C_{24}H_{20}N_6O_2S.\frac{1}{2}H_2O$ (Mw. 465.54): | | | |
|---|---|---|---|
| | C (%) | H (%) | N (%) |
| Calcd: | 61.92; | 4.55; | 18.05 |
| Found: | 61.94; | 4.44; | 18.20 |

$^1$H-NMR(200 MHz,DMSO-d$_6$) δ: 2.09(3H,s), 3.98(2H,s), 5.89(2H,s), 6.80(2H,d), 7.00(2H,d), 7.27(1H,t), 7.45–7.69(5H,m), 7.87(1H,dd).

WORKING EXAMPLE 52

2-Hydroxymethyl-1-[[2'-(1H-tetrazol-5-yl)biphenyl-4-yl]methyl]benzimidazole-7-carboxylic acid colorless powder (65%), m.p. 292°–294° C.

| Elemental Analysis for $C_{23}H_{18}N_6O_3$.3/10 $H_2O$ (Mw. 431.84): | | | |
|---|---|---|---|
| | C (%) | H (%) | N (%) |
| Calcd: | 63.97; | 4.34; | 19.46 |
| Found: | 64.01; | 4.29; | 19.49 |

$^1$H-NMR(200 MHz,DMSO-$d_6$) δ: 4.72(2H,s), 5.92(2H,s), 6.83(2H,d), 6.98(2H,d), 7.27(1H,t), 7.45–7.68(5H,m), 7.88(1H,dd).

WORKING EXAMPLE 53

2-Ethylthiomethyl-1-[[2'-(1H-tetrazol-5-yl)biphenyl-4-yl]methyl]benzimidazole-7-carboxylic acid colorless crystals (76%), m.p. 157°–160° C.

| Elemental Analysis for $C_{25}H_{22}N_6O_2S$.9/10 $H_2O$: | | | |
|---|---|---|---|
| | C (%) | H (%) | N (%) |
| Calcd: | 61.69; | 4.93; | 17.26 |
| Found: | 61.75; | 4.91; | 17.26 |

$^1$H-NMR(200 MHz,DMSO-$d_6$) δ: 1.18(3H,t), 2.54(2H,q), 4.01(2H,s), 5.89(2H,s), 6.80(2H,d), 7.00(2H,d), 7.27(1H,t), 7.45–7.68(5H,m), 7.87(1H,dd).

WORKING EXAMPLE 54

2-Methylaminomethyl-1-[[2'-(1H-tetrazol-5-yl)biphenyl-4-yl]methyl]benzimidazole-7-carboxylic acid colorless powder (48%).

$^1$H-NMR(200 MHz,DMSO-$d_6$) δ: 2.66(3H,s), 4.42(2H,s) 5.84(2H,s), 6.79(2H,d), 7.00(2H,d), 7.27–7.68(6H,m), 7.87(1H,d).

The following compounds (Working Examples 55–58) were prepared by a method like that of Working Example 31.

WORKING EXAMPLE 55

Methyl 2-methylthiomethyl-1-[[2'-(1H-tetrazol-5-biphenyl-4-yl]methyl]benzimidazole-7-carboxylate colorless powder (54%), m.p. 186°–188° C.

| Elemental Analysis for $C_{25}H_{22}N_6O_2S.\frac{1}{2} H_2O$: | | | |
|---|---|---|---|
| | C (%) | H (%) | N (%) |
| Calcd: | 62.61; | 4.83; | 17.52 |
| Found: | 62.82; | 4.63; | 17.69 |

$^1$H-NMR(200 MHz,CDCl$_3$) δ: 2.03(3H,s), 3.70(3H,s), 3.36(2H,s), 5.63(2H,s), 6.64(2H,d), 6.94(2H,d), 7.18(1H,t), 7.30–7.40(2H,m), 7.57–7.66(3H,m), 8.02–8.07(1H,m).

WORKING EXAMPLE 56

Methyl 2-ethylthiomethyl-1-[[2'-(1H-tetrazol-5-biphenyl-4-yl]methyl]benzimidazole-7-carboxylate pale yellow powder (49%).

| Elemental Analysis for $C_{26}H_{24}N_6O_2S.\frac{1}{2} H_2O$: | | | |
|---|---|---|---|
| | C (%) | H (%) | N (%) |
| Calcd: | 63.27; | 5.11; | 17.03 |
| Found: | 63.42; | 4.87; | 16.92 |

$^1$H-NMR(200 MHz,CDCl$_3$) δ: 1.09(3H,t), 2.42(2H,q), 3.22(2H,s), 3.64(3H,s), 5.57(2H,s), 6.53(2H,d), 6.84(2H,d), 7.13(2H,d), 7.31–7.38(1H,m), 7.56–7.65(3H,m), 7.89–7.98(1H,m).

WORKING EXAMPLE 57

Methyl 2-hydroxymethyl-1-[[2'-(1H-tetrazol-5-yl)biphenyl-4-yl]methyl]benzimidazole-7-carboxylate colorless powder (30%).

$^1$H-NMR(200 MHz,CDCl$_3$) δ: 3.63(3H,s), 4.77(2H,s), 5.75(2H,s), 6.76(2H,d), 6.99(2H,d), 7.23(1H,t), 7.39–7.62(5H,m), 7.90(1H,dd).

WORKING EXAMPLE 58

Methyl 2-ethoxymethyl-1-[[2'-(1H-tetrazol-5-biphenyl-4-yl]methyl]benzimidazole-7-carboxylate colorless needles (61%), m.p. 214°–217° C.

| Elemental Analysis for $C_{26}H_{24}N_6O_3$.1/5 $H_2O$: | | | |
|---|---|---|---|
| | C (%) | H (%) | N (%) |
| Calcd: | 66.08; | 5.18; | 17.87 |
| Found: | 66.15; | 5.21; | 17.80 |

$^1$H-NMR(200 MHz,CDCl$_3$) δ: 1.14(3H,t), 3.44(2H,q), 3.68(3H,s), 4.13(2H,s), 5.63(2H,s), 6.61(2H,d), 6.89(2H,d), 7.16(1H,t), 7.19–7.39(2H,m), 7.57–7.64(3H,m), 7.97–8.02(1H,m).

WORKING EXAMPLE 59

Ethyl 2-chloromethyl-1-[[2'-(1H-tetrazol-5-yl)biphenyl-4-yl]methyl]benzimidazole-7-carboxylate To a solution of ethyl 2-hydroxymethyl-1-[[2'-(1H-tetrazol-5-yl)biphenyl-4-yl]methyl]benzimidazole-7carboxylate (0.2 g) in CH$_2$Cl$_2$ (3 ml) was added thionyl chloride (0.3 ml) dropwise and the mixture was refluxed for 3 hours. The reaction solution was poured into ice-water and the organic layer was washed with water, dried and evaporated to dryness to give a pale yellow amorphous powder (0.2 g, 96%).

$^1$H-NMR(200 MHz,CDCl$_3$) δ: 1.29(3H,t), 4.19(2H,q), 4.63(2H,s), 5.77(2H,s), 6.75(2H,d), 7.03(2H,d), 7.28(1H,t), 7.35–7.39(1H,m), 7.56–7.72(4H,m), 8.06–8.11(1H,m).

WORKING EXAMPLE 60

Ethyl 2-methylaminomethyl-1-[[2'-(1H-tetrazol-5-yl)biphenyl-4-yl]methyl]benzimidazole-7-carboxylate To a solution of ethyl 2-chloromethyl-1-[[2´-(1H-tetrazol-5-yl)biphenyl-4-yl]methyl]benzimidazole-7carboxylate (0.2 g) in acetonitrile (5 ml) was added a solution of 40% methylamine in methanol (0.33 g) and the mixture was heated at 60° C. for 77 hours. The reaction solution was cooled to give pale yellow prisms (0.12 g, 61%), m.p. 248°–250° C.

¹H-NMR(200 MHz,DMSO-d₆) δ: 1.14(3H,t), 2.62(3H,s), 4.16(2H,q), 4.39(2H,s), 5.71(2H,s), 6.73(2H,d), 7.03(2H,d), 7.27–7.46(4H,m), 7.54–7.63(2H,m), 7.94(1H,dd).

The following compounds (Working Examples 61–62) were prepared by a method like that of Working Example 1.

WORKING EXAMPLE 61

Ethyl 2-isobutyl-1-[[2'-(1H-tetrazol-5-yl)biphenyl-4-yl]methyl]benzimidazole-7-carboxylate colorless prism (71%).

¹H-NMR(90 MHz,CDCl₃) δ: 0.87(6H,d), 1.13(3H,t), 1.23(1H,t), 1.83–2.40(1H,m), 2.00(1H,s), 2.27(2H,d), 4.03(2H,q), 4.13(1H,q), 5.47(2H,s), 6.43(2H,d), 6.73(2H,d), 6.87–7.70(6H,m), 7.90–8.00(1H,m).

WORKING EXAMPLE 62

Ethyl 2-sec-butyl-1-[[2'-(1H-tetrazol-5-yl)biphenyl-4-yl]methyl]benzimidazole-7-carboxylate colorless prism (43%), m.p. 128°–130° C.

¹H-NMR(90 MHz,CDCl₃) δ: 0.87(3H,t), 1.00–1.17(6H,m), 1.23(1H,t), 1.50–1.90(2H,m), 2.03(1H,s), 2.63–3.03(1H,m), 4.00(2H,q), 4.13(1H,q), 5.57(1H,d), 5.77(1H,d), 6.50(2H,d), 6.77(2H,d).

IR(Nujol)cm⁻¹: 2720, 1730, 1450, 1280, 1265, 1200, 760, 765.

The following compounds (Working Examples 63–64) were prepared by a method like that of Working Example 49.

WORKING EXAMPLE 63

2-Isobutyl-1-[[2'-(1H-tetrazol-5-yl)biphenyl-4-yl]methyl]benzimidazole-7-carboxylic acid colorless powder (62%), m.p. 205°–207° C.(d).

| Elemental Analysis for C₂₆H₂₄N₆O₂·2/5 H₂O: | | |
|---|---|---|
| C (%) | H (%) | N (%) |
| Calcd: 67.93; | 5.44; | 18.23 |
| Found: 67.98; | 5.63; | 18.43 |

¹H-NMR(90 MHz,CDCl₃) δ: 1.57(6H,d), 3.40–3.83(1H,m), ° 20 6.00(2H,s), 6.90(2H,d), 7.13(2H,d), 7.43–7.83(5H,m), 7.97–8.12(2H,m).

IR(Nujol)cm⁻¹: 2460, 1690, 1410, 1290, 1245, 1200, 1120, 760.

WORKING EXAMPLE 64

2-sec-Butyl-1-[[2'-(1H-tetrazol-5-yl)biphenyl-4-yl]methyl]benzimidazole-7-carboxylic acid colorless prism (79%), m.p. 184°–186° C.

| Elemental Analysis for C₂₆H₂₄N₆O₂·½ EtOH: | | |
|---|---|---|
| C (%) | H (%) | N (%) |
| Calcd: 68.20; | 5.72; | 17.67 |
| Found: 67.96; | 5.71; | 17.46 |

¹H-NMR(90 MHz,DMSO-d₆) δ: 0.83(3H,t), 1.17(1H,t), 1.30(3H,d), 1.53–2.13(2H,m), 2.77–3.13(1H,m), 3.63(1H,q), 5.90(2H,s), 6.80(2H,d), 7.03(2H,d), 7.23(1H,t), 7.33–7.97(7H,m).

IR(Nujol)cm⁻¹: 2600, 1700, 1450, 1410, 1275, 1230, 1200, 1140, 750.

The following compounds (Working Examples 65–66) were prepared by a method like that of Working Example 19.

WORKING EXAMPLE 65

Methyl 2-(2-methoxyethyl)-1-[[2'-(1H-tetrazol-5-yl)biphenyl-4-yl]methyl]benzimidazole-7-carboxylate pale yellow powder (35%).

¹H-NMR(200 MHz,CDCl₃) δ: 2.60(2H,t), 3.61(2H,t), 3.19(3H,t), 3.63(3H,t), 5.60(2H,s), 6.56(2H,d), 6.85(2H,d), 7.07–7.12(2H,m), 7.30–7.35(1H,m), 7.51–7.65(3H,m), 7.96(1H,dd).

WORKING EXAMPLE 66

Methyl 2-(2-methylthioethyl)-1-[[2'-(1H-tetrazol-5-yl)biphenyl-4-yl]methyl]benzimidazole-7-carboxylate pale yellow powder (16%).

¹H-NMR(200 MHz,CDCl₃) δ: 2.09(3H,t), 3.63(3H,s), 2.72–2.96(4H,m), 5.65(2H,s), 6.60(2H,d), 6.87(2H,d), 7.06–7.20(2H,m), 7.29–7.34(1H,m), 7.54–7.63(3H,m), 7.99–8.05(1H,m).

WORKING EXAMPLE 67

Methyl 2-butyl-1-[[2'-(1-methyltetrazol-5-yl)biphenyl-4-yl]methyl]benzimidazole-7-carboxylate and methyl 2-butyl-1-[[2'-(2-methyltetrazole-5-yl)biphenyl-4-yl]methyl]benzimidazole-7-carboxylate A mixture of 2-butyl-1-[2'-(1H-tetrazol-5-yl)biphenyl-4-yl]methyl]benzimidazole-7-carboxylic acid (2.0 g), NaHCO₃ (1.1 g) and methyl iodide (1.5 g) in DMF (10 ml) was stirred at room temperature for 15 hours. The reaction mixture was diluted with water and then the mixture was extracted with ethyl acetate. The organic layer was washed with water, dried and concentrated to dryness. The resulting residue was purified by column chromatography on silica gel to give 1-methyl derivative (0.95 g, 45%) and 2-methyl derivative (0.36 g, 17%).

1-Methyl derivative (67a): m.p. 200°–201° C.

| Elemental Analysis for C₂₈H₂₈N₆O₂: | | |
|---|---|---|
| C (%) | H (%) | N (%) |
| Calcd: 69.98; | 5.87; | 17.49 |
| Found: 69.67; | 5.80; | 17.36 |

¹H-NMR(200 MHz,CDCl₃) δ: 0.97(3H,t), 1.39–1.58(2H,m), 1.81–1.97(2H,m), 2.91(2H,t), 3.16(3H,s), 3.74(3H,s), 5.72(2H,s), 6.77(2H,d), 7.00(2H,d), 7.25(1H,t), 7.48–7.69(5H,m), 7.95(1H,dd).

2-Methyl derivative (67b): pale yellow syrup.

¹H-NMR(200 MHz,CDCl₃) δ: 0.96(3H,t), 1.38–1.57(2H,m), 1.80–1.96(2H,m), 2.92(2H,t), 3.71(3H,s), 4.18(3H,s), 5.73(2H,s), 6.77(2H,d), 7.06(2H,d), 7.24(1H,t), 7.35–7.55(3H,m), 7.59(1H,dd), 7.80(1H,dd), 7.94(1H,dd).

IR(Neat)cm⁻¹: 1725, 1520, 1460, 1435, 1400, 1360, 1280, 1265, 1220, 1200, 1125, 760.

WORKING EXAMPLE 68

2-Butyl-1-[[2'-(1H-tetrazol-5-yl)biphenyl-4-yl]methyl]-7-formylaminobenzimidazole and 2-butyl-1-[[2'-(1H-tetrazol-5-yl)biphenyl-4-yl]methyl]-7-ethoxycarbonylaminobenzimidazole A mixture of 2-butyl-1-[[2'-(1H-tetrazol-5-yl)biphenyl-4-yl]methyl]benzimidazole-7-carboxylic acid (0.94 g), diphenylphosphoryl azide (0.61 g) and triethylamine (0.61 g) in DMF (6 ml) was stirred at room temperature for 7 hours and then the reaction mixture was concentrated to dryness to give a crystalline residue. The residue was chromatographed on silica gel column to give two colorless crystalline products (68a and 68b).

Formylamino derivative (68a): colorless crystals (0.26 g, 29%), m.p. 290°-292° C.(d).

| Elemental Analysis for $C_{26}H_{25}N_7O$: | | |
|---|---|---|
| C (%) | H (%) | N (%) |
| Calcd: 69.16; | 5.58; | 21.71 |
| Found: 69.29; | 5.51; | 21.94 |

$^1$H-NMR(200 MHz,CDCl$_3$) δ: 0.84(3H,t), 1.22-1.40(2H,m), 1.56-1.71(2H,m), 2.70(2H,t), 5.55(2H,s), 6.79(1H,d), 6.89(2H,d), 6.98-7.07(3H,m), 7.43(2H,d), 7.51-7.70(3H,m), 8.27(1H,s).
IR(KBr)cm$^{-1}$: 3340, 1630, 1530, 1510, 1420, 1400, 750, 730.

Ethoxycarbonylamino derivative (68b): colorless crystals (0.31 g, 31%), m.p. 190°-194° C.(d).

| Elemental Analysis for $C_{28}H_{29}N_7O_2 \cdot 0.1$ $H_2O$: | | |
|---|---|---|
| C (%) | H (%) | N (%) |
| Calcd: 67.62; | 5.92; | 19.71 |
| Found: 67.43; | 5.81; | 19.70 |

$^1$H-NMR(200 MHz,CDCl$_3$) δ: 0.87(3H,t), 1.18(3H,t), 1.25-1.39(3H,m), 1.56-1.71(2H,m), 2.50(2H,t), 3.99(2H,q), 5.37(2H,s), 6.07(1H,s), 6.66(2H,d) 6.90-7.05(5H,m), 7.34(1H,dd), 7.55-7.64(2H,m), 8.00(1H,dd).
IR(KBr)cm$^{-1}$: 1700, 1520, 1250, 750.

WORKING EXAMPLE 69

2-Butyl-1-[[2'-(1H-tetrazol-5-yl)biphenyl-4-yl]methyl]-7-(N,N-dimethylaminomethyl)benzimidazole This compound was prepared by a method like that of Working Example 44.

colorless crystals (56%), m.p. 178°-180° C.(d).

| Elemental Analysis for $C_{28}H_{31}N_7 \cdot 2HCl \cdot 2H_2O \cdot \frac{1}{4}$ AcOEt: | | |
|---|---|---|
| C (%) | H (%) | N (%) |
| Calcd: 58.25; | 6.68; | 15.85 |
| Found: 58.42; | 6.42; | 15.61 |

$^1$H-NMR(200 MHz,DMSO-d$_6$) δ: 0.91(3H,f), 1.33-1.51(2H,m), 1.71-1.86(2H,m), 2.50(6H,s), 3.17(2H,t), 4.32(2H,s), 5.92(2H,s), 7.07(2H,d), 7.14(2H,d), 7.49-7.72(5H,m), 7.80(1H,d), 7.92(1H,d).
IR(KBr)cm$^{-1}$: 3400, 1500, 1470, 1435, 1420, 750.

The following compounds (Working Examples 70-71) were prepared by a method like that of Working Example 44.

WORKING EXAMPLE 70

2-Butyl-1-[[2'-(1-methyltetrazol-5-yl)biphenyl-4-yl]methyl]benzimidazole-7-carboxylic acid colorless prism (78%), m.p. 213°-214° C.

| Elemental Analysis for $C_{27}H_{26}N_6O_2 \cdot \frac{1}{4}$ $H_2O$: | | |
|---|---|---|
| C (%) | H (%) | N (%) |
| Calcd: 68.19; | 5.72; | 17.67 |
| Found: 68.52; | 5.55; | 17.62 |

$^1$H-NMR(200 MHz,CDCl$_3$) δ: 0.95(3H,t), 1.38-1.57(2H,m), 1.80-1.95(2H,m), 2.99(2H,t), 3.18(3H,s), 5.82(2H,s), 6.80(2H,d), 6.97(2H,d), 7.27(1H,t), 7.48-7.68(4H,m), 7.80(1H,d), 7.98(1H,d).
IR(KBr)cm$^{-1}$: 1700, 1520, 1470, 1445, 1435, 1410, 1290, 1280, 1230, 1185, 1145, 1120, 1100, 820, 770, 760, 745, 730.

WORKING EXAMPLE 71

2-Butyl-1-[[2'-(2-methyltetrazol-5-yl)biphenyl-4-yl]methyl]benzimidazole-7-carboxylic acid colorless needles (71%), m.p. 226°-228° C.(d).

| Elemental Analysis for $C_{27}H_{26}N_6O_2 \cdot 0.7$ $H_2O$: | | |
|---|---|---|
| C (%) | H (%) | N (%) |
| Calcd: 67.68; | 5.76; | 17.54 |
| Found: 67.48; | 5.51; | 17.26 |

$^1$H-NMR(200 MHz,CDCl$_3$) δ: 0.94(3H,t), 1.38-1.56(2H,m), 1.79-1.94(2H,m), 3.07(2H,t), 4.22(3H,s), 5.84(2H,s), 6.81(2H,d), 7.06(2H,d), 7.25-7.55(4H,m), 7.74(1H,d), 7.81(1H,dd), 8.00(1H,d).
IR(KBr)cm$^{-1}$: 1700, 1510, 1450, 1430, 1410, 1360, 1290, 1240, 1190, 1150, 1120, 1100, 1060, 1035, 1000, 820, 760, 750, 740, 720.

WORKING EXAMPLE 72

2-Butyl-1-[[2'-(N-pivaloyloxymethyltetrazol-5-yl)biphenyl-4-yl]methyl]benzimidazole-7-carboxylic acid A mixture of 2-butyl-1-[[2'-(1H-tetrazol-5-yl)biphenyl-4-yl]methyl]benzimidazole-7-carboxylic acid (0.71 g), K$_2$CO$_3$ (0.21 g) and iodomethylpivalate (0.36 g) in DMF (2 ml) was stirred at room temperature for 17 hours. The reaction mixture was digested with water and made acidic (pH 3-4) with 1N-HCl. The mixture was extracted with ethyl acetate and the organic layer was washed with H$_2$O, dried and evaporated to dryness to give a residue. The residue was purified by column chromatography on silica gel to afford colorless powder (0.2 g, 23%), m.p. 188°-191° C.(d).

| Elemental Analysis for $C_{32}H_{34}N_6O_4 \cdot 0.6$ $H_2O$: | | |
|---|---|---|
| C (%) | H (%) | N (%) |
| Calcd: 66.56; | 6.14; | 14.55 |
| Found: 66.82; | 6.28; | 14.13 |

$^1$H-NMR(200 MHz,CDCl$_3$) δ: 0.94(3H,t), 0.96 and 1.18(9H,s), 1.36-1.55(2H,m), 1.77-1.93(2H,m), 2.90-2.97(2H,m), 5.39(1.5H,s), 5.81(2H,s), 6.36(0.5H,s), 6.76-6.83(2H,m), 6.96-7.03(2H,m), 7.20-7.29(1H,m), 7.38-7.97(6H,m).

IR(KBr)cm$^{-1}$: 1760, 1600, 1460, 1410, 1275, 1240, 1125, 1100, 760.

The following compounds (Working Examples 73-76) were prepared according to the procedure described in Working Example 36.

WORKING EXAMPLE 73

Pivaloyloxymethyl
2ethyl-1-[[2'-(1H-tetrazol-5-yl)biphenyl-4-yl]methyl]-benzimidazole-7-carboxylate

WORKING EXAMPLE 74

Pivaloyloxymethyl
2-propyl-1-[[2'-(1H-tetrazol-5-yl)biphenyl-4-yl]methyl]-benzimidazole-7-carboxylate

WORKING EXAMPLE 75

1-(Cyclohexyloxycarbonyloxy)ethyl
2-propyl-1-[[2'-(1H-tetrazol-5-yl)biphenyl-4-yl]methyl]-benzimidazole-7-carboxylate

WORKING EXAMPLE 76

1-(Cyclohexyloxycarbonyloxy)ethyl
2-ethyl-1-[[2'-(1H-tetrazol-5-yl)biphenyl-4-yl]methyl]-benzimidazole-7-carboxylate

Experimental Example 1

Inhibition of binding of angiotensin-II to angiotensin receptor
Method

An experiment of inhibition on the binding of angiotensin II (A-II) to A-II-receptor was conducted by modifying the method of Douglas et al. [Endocrinology, 102, 685-696 (1978)]. An A-II receptor was prepared from the membrane fraction of bovine adrenal cortex.

The compound of this invention ($10^{-6}$M or $10^{-5}$M) and $^{125}$I-A-II (1.85 kBq/50 μl) were added to the receptor membrane fraction, and the mixture was incubated for one hour at room temperature. The receptor-bound and free $^{125}$I-A-II were separated though a filter (Whatman GF/B filter), and the radioactivity of $^{125}$I-A-II bound to the receptor was measured.

Results

The results relating to the compounds of this invention are shown in Table 1.

Experimental Example 2

Inhibitory effect of the compound of this invention on pressor action of A-II
Method Jcl : SD rats (9 week old, male) were used. On the day prior to that of the experiment, these animals were applied with cannulation into the femoral artery and vein under anesthesia with pentobarbital Na. The animals were fasted but allowed free access to drinking water until the experiment was started. On the day of conducting the experiment, the artery cannula was connected with a blood-pressure transducer, and the average blood pressure was recorded by means of polygraph. Before administration of the drug, the pressor action due to intravenous administration of A-II (100 ng/kg) as the control was measured. The drugs were orally administered, and then, at each point of the measurement, A-II was administered intravenously, and the pressor action was similarly measured. By comparing the pressor action before and after administration of the drug, the percent inhibition by the drug on A-II-induced pressor action was evaluated.

Results

The results relating to the compounds of this invention are shown in Table 1.

TABLE 1

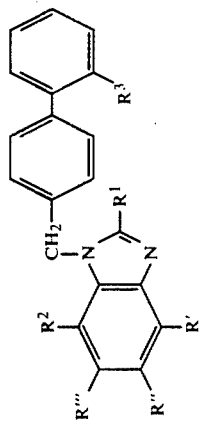

| No. | R¹ | R' | R'' | R''' | R² | R³ | Radioreceptor assay $1 \times 10^{-6}M$ | $1 \times 10^{-5}M$ | Pressor response to A II (p.o.) 3 mg/kg | 30 mg/kg |
|---|---|---|---|---|---|---|---|---|---|---|
| Working Example | | | | | | | | | | |
| 1 | Bu | H | H | H | COOH | Tet | 78 | 95 | +++*2 | +++ |
| 4 | Bu | H | H | H | COONa | Tet.Na | 71 | 91 | +++ | +++ |
| 7 | Pr | H | H | H | COOH | Tet | 79 | 95 | +++ | +++ |
| 9 | Bu | H | Me | H | COOMe | COOMe | 45 | 92 | +++*2 | NT |
| 10 | Bu | H | Me | H | COOH | Tet | 40 | 90 | +++ | +++ |
| 12 | Bu | H | Cl | H | COOMe | Tet | 65 | 91 | +++ | +++ |
| 14 | Bu | H | H | H | COOEt | Tet | 50 | 82 | ++ | +++ |
| 16 | Bu | H | H | H | CH₂OH | Tet | 67 | 90 | NT*1 | NT |
| 17 | Bu | H | H | H | CH₂COOEt | Tet | 75 | 93 | +*2 | NT |
| 19 | Bu | H | H | H | CH₂OMe | Tet | 60 | 90 | + | +++ |
| 27 | Et | H | H | H | COOH | Tet | 91 | 96 | ++ | +++ |
| 28 | iPr | H | H | H | COOH | Tet | 88 | 98 | + | NT |
| 29 | Bu | H | H | H | COOK | Tet.K | 60 | 87 | +++ | +++ |
| 31 | Pr | H | H | H | COOMe | Tet | 78 | 92 | +++ | +++ |
| 34 | Bu | H | H | H | COOMe | Tet | 66 | 90 | +++ | +++ |
| 36 | Bu | H | H | H | —COOCH₂OC^tBu | Tet | 86 | 95 | +++ | +++ |
| 37 | Bu | H | H | H | —COOCHOCO—cyclohexyl, Me | Tet | 65 | 94 | +++ | +++ |
| 39 | Bu | H | H | H | —COOCH₂— (dioxolone with Me) | Tet | 83 | 97 | +++ | +++ |
| 49 | —CH₂OMe | H | H | H | COOH | Tet | 35 | 73 | +++ | +++ |
| 51 | —CH₂SMe | H | H | H | COOH | Tet | 45 | 76 | +++ | +++ |
| Reference Example | | | | | | | | | | |
| 17 | Bu | H | H | H | H | Tet | 52 | 87 | —*2 | — |

TABLE 1-continued

| No. | R¹ | R' | R'' | R''' | R² | R³ | Radioreceptor assay $1 \times 10^{-6}$M | $1 \times 10^{-5}$M | Pressor response to A II (p.o.) 3 mg/kg | 30 mg/kg |
|---|---|---|---|---|---|---|---|---|---|---|
| 19 | Bu | H | H | OMe | H | Tet | 47 | 88 | — | NT |
| 21 | Bu | H | H | Cl | H | Tet | 22 | 79 | — | — |
| 26 | Bu | COOMe | H | H | H | COOH | 48 | 87 | | NT |
| 29 | Bu | CONH₂ | H | H | H | Tet | 6 | 61 | — | — |
| 30 | Bu | H | COOH | H | H | Tet | 1 | 40 | — | — |
| 44 | Bu | H | H | COOMe | H | Tet | 13 | 66 | — | NT |
| 49 | Bu | H | H | COOH | H | Tet | 77 | 94 | — | — |
| 50 | Bu | H | H | H | H | Tet | 7 | 53 | — | — |

*¹NT = not tested
*² +++ ≧70% > ++ ≧50% > + ≧30% > —

What is claimed is:
1. A compound of the formula:

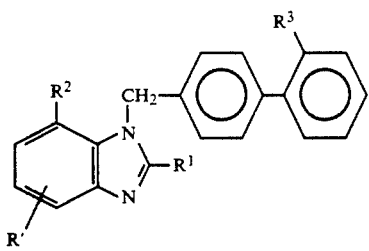

wherein $R^1$ is propyl or butyl;
$R^2$ is carboxyl, methoxycarbonyl, pivaloyloxymethoxycarbonyl, or 1-(cyclohexyloxycarbonyloxy)ethoxycarbonyl;
$R^3$ is tetrazolyl; and
$R'$ is hydrogen; or
a pharmaceutically acceptable salt thereof.

2. A compound according to claim 1, which is 2-butyl-1-[[2'-(1H-tetrazol-5-yl)biphenyl-4-yl] methyl]-benzimidazole-7-carboxylic acid.

3. A compound according to claim 1, which is pivaloyloxymethyl 2-butyl-1-[[2'-(1H-tetrazol-5-yl)biphenyl-4-yl]methyl]benzimidazole-7carboxylate.

4. A compound according to claim 1, which is 1-(cyclohexyloxycarbonyloxy)ethyl 2-butyl-1-[[2'-(1H-tetrazol-5-yl)biphenyl-4-yl]methyl]benzimidazole-7-carboxylate.

5. A compound according to claim 1, which is methyl 2-butyl-1-[[2'-1H-tetrazol-5-yl)biphenyl-4-yl]methyl]-benzimidazole-7-carboxylate.

6. A compound according to claim 1, which is 2-propyl-1-[[2'-(1H-tetrazol-5-yl)biphenyl-4-yl]methyl]benzimidazole-7carboxylic acid.

7. A pharmaceutical composition suitable for antagonizing angiotensin II which comprises (a) as the active ingredient, an amount effective to antagonize angiotensin II of a compound according to claim 1 or a pharmaceutically acceptable salt thereof and (b) a pharmaceutically acceptable carrier, excipient or diluent therefore.

8. A method for antagonizing angiotensin II in a mammal, which comprises administering to said mammal an effective amount of a compound according to claim 1 or a pharmaceutically acceptable salt thereof.

* * * * *